United States Patent
Felber et al.

(10) Patent No.: US 9,790,261 B2
(45) Date of Patent: Oct. 17, 2017

(54) CODON OPTIMIZED IL-15 AND IL-15R-ALPHA GENES FOR EXPRESSION IN MAMMALIAN CELLS

(71) Applicant: The United States of America as Represented by the Secretary of the Department of Health and Human Services, Washington, DC (US)

(72) Inventors: Barbara K. Felber, Rockville, MD (US); George N. Pavlakis, Rockville, MD (US)

(73) Assignee: THE UNITED STATES OF AMERICA, AS REPRESENTED BY THE SECRETARY, DEPARTMENT OF HEALTH AND HUMAN SERVICES, Rockville, MD (US)

( * ) Notice: Subject to any disclaimer, the term of this patent is extended or adjusted under 35 U.S.C. 154(b) by 0 days.

(21) Appl. No.: 14/739,796

(22) Filed: Jun. 15, 2015

(65) Prior Publication Data
US 2016/0102128 A1    Apr. 14, 2016

Related U.S. Application Data

(62) Division of application No. 12/160,263, filed as application No. PCT/US2007/000774 on Jan. 12, 2007, now Pat. No. 9,303,080.

(60) Provisional application No. 60/812,566, filed on Jun. 9, 2006, provisional application No. 60/758,819, filed on Jan. 13, 2006.

(51) Int. Cl.
*C07K 14/54* (2006.01)
*C07K 14/715* (2006.01)
*C07K 14/535* (2006.01)

(52) U.S. Cl.
CPC ........ *C07K 14/5443* (2013.01); *C07K 14/535* (2013.01); *C07K 14/7155* (2013.01); *C07K 2319/02* (2013.01)

(58) Field of Classification Search
CPC ............ C07K 14/5443; C07K 14/7155; C07K 2319/02
See application file for complete search history.

(56) References Cited

U.S. PATENT DOCUMENTS

| | | | |
|---|---|---|---|
| 5,552,303 A | 9/1996 | Grabstein et al. |
| 5,574,138 A | 11/1996 | Grabstein et al. |
| 5,965,726 A | 10/1999 | Pavlakis |
| 5,972,596 A | 10/1999 | Pavlakis et al. |
| 6,001,973 A | 12/1999 | Strom et al. |
| 6,063,911 A | 5/2000 | Vournakis et al. |
| 6,174,666 B1 | 1/2001 | Pavlakis |
| 6,291,664 B1 | 9/2001 | Pavlakis |
| 6,414,132 B1 | 7/2002 | Pavlakis |
| 6,451,308 B1 | 9/2002 | Strom et al. |
| 6,548,065 B1 | 4/2003 | Anderson et al. |
| 6,764,836 B2 | 7/2004 | Anderson et al. |
| 6,787,132 B1 | 9/2004 | Gabizon et al. |
| 6,794,498 B2 | 9/2004 | Pavlakis |
| 6,864,245 B2 | 3/2005 | Vournakis et al. |
| 6,998,476 B2 | 2/2006 | Strom et al. |
| 7,067,132 B2 | 6/2006 | Grabstein et al. |
| 7,112,436 B1 | 9/2006 | Rose-John |
| 7,258,853 B2 | 8/2007 | Strom et al. |
| 7,435,596 B2 | 10/2008 | Campana et al. |
| 7,638,604 B2 | 12/2009 | Li et al. |
| 7,858,081 B2 | 12/2010 | Bernard et al. |
| 8,124,084 B2 | 2/2012 | Lefrancois et al. |
| 8,163,879 B2 | 4/2012 | Wong et al. |
| 8,224,578 B2 | 7/2012 | Raab et al. |
| 8,492,118 B2 | 7/2013 | Wong et al. |
| 8,507,222 B2 | 8/2013 | Wong et al. |
| 8,859,275 B2 | 10/2014 | Notka et al. |
| 8,940,288 B2 | 1/2015 | Lefrancois et al. |
| 2002/0022030 A1 | 2/2002 | Marrack et al. |
| 2002/0114781 A1 | 8/2002 | Strom et al. |
| 2002/0127201 A1 | 9/2002 | Boussiotis et al. |
| 2002/0128436 A1 | 9/2002 | Strom et al. |
| 2002/0182178 A1 | 12/2002 | Grooten et al. |
| 2003/0105295 A1 | 6/2003 | Strom et al. |

(Continued)

FOREIGN PATENT DOCUMENTS

| | | |
|---|---|---|
| CA | 2625694 A1 | 4/2007 |
| EP | 1777294 A1 | 4/2007 |

(Continued)

OTHER PUBLICATIONS

Alberts et al, Molecular Biology of the Cell, Third Edition, Garland Publishing, New York, NY, 1994.*
Anderson, D.,et al., "Functional characterization of the human interleukin-15 receptor alpha chain and close linkage of IL15RA and IL2RA genes," 1995, *J. Biol. Chem.* vol. 270(50), pp. 29862-29869.
Database EMBL-EBI Accession No. BC074726, Jul. 8, 2004 "*Homo sapiens* interleukin 15 receptor, alpha, transcript variant 1, mRNA (cDNA clone MGC:103798 Image:30915179), complete cds." (2 pages).
Database EMBL-EBI Accession No. U31628, Dec. 23, 1995 (last version Nov. 14, 2006) "Human interleukin-15 receptor alpha chain precursor (IL15RA) mRNA, complete cds." (2 pages).

(Continued)

*Primary Examiner* — Kevin Hill
(74) *Attorney, Agent, or Firm* — Jean M. Lockyer; Kilpatrick Townsend & Stockton LLP

(57) ABSTRACT

The present invention provides for nucleic acids improved for the expression of interleukin-15 (IL-15) in mammalian cells. The invention further provides for methods of expressing IL-15 in mammalian cells by transfecting the cell with a nucleic acid sequence encoding an improved IL-15 sequence.
The present invention further provides expression vectors, and IL-15 and IL-15 receptor alpha combinations (nucleic acid and protein) that increase IL-15 stability and potency in vitro and in vivo. The present methods are useful for the increased bioavailability and biological effects of IL-15 after DNA, RNA or protein administration in a subject (e.g. a mammal, a human).

26 Claims, 60 Drawing Sheets

(56) References Cited

U.S. PATENT DOCUMENTS

| | | |
|---|---|---|
| 2003/0138441 A1 | 7/2003 | Bollen et al. |
| 2003/0236255 A1 | 12/2003 | Waer et al. |
| 2004/0087015 A1 | 5/2004 | Vournakis et al. |
| 2004/0170604 A1 | 9/2004 | Ekida et al. |
| 2004/0209241 A1 | 10/2004 | Hermanson et al. |
| 2004/0253587 A1 | 12/2004 | Grabstein et al. |
| 2005/0032167 A1 | 2/2005 | Anderson et al. |
| 2005/0042220 A1 | 2/2005 | Li et al. |
| 2005/0202005 A1 | 9/2005 | Winchester et al. |
| 2006/0057102 A1 | 3/2006 | Zheng et al. |
| 2006/0057680 A1 | 3/2006 | Zheng et al. |
| 2006/0093605 A1 | 5/2006 | Campana et al. |
| 2006/0104945 A1 | 5/2006 | Choi |
| 2006/0147419 A1 | 7/2006 | Perera et al. |
| 2006/0165668 A1 | 7/2006 | Liu et al. |
| 2006/0257361 A1 | 11/2006 | Watanabe et al. |
| 2006/0263857 A1* | 11/2006 | Lefrancois ......... C07K 14/5443 435/69.52 |
| 2007/0110714 A1 | 5/2007 | Hayashi |
| 2007/0134718 A1 | 6/2007 | Grooten et al. |
| 2007/0141557 A1 | 6/2007 | Raab et al. |
| 2007/0160578 A1 | 7/2007 | Waldmann et al. |
| 2007/0190031 A1* | 8/2007 | Sidhu ..................... A61K 39/21 424/93.2 |
| 2008/0255039 A1 | 10/2008 | Bernard et al. |
| 2009/0017000 A1 | 1/2009 | Cai et al. |
| 2009/0082299 A1 | 3/2009 | Felber et al. |
| 2009/0238791 A1 | 9/2009 | Jacques et al. |
| 2011/0081311 A1 | 4/2011 | Pavlakis et al. |
| 2011/0158938 A1 | 6/2011 | Bernard et al. |
| 2012/0230946 A1 | 9/2012 | Wong et al. |
| 2014/0134128 A1 | 5/2014 | Wong et al. |

FOREIGN PATENT DOCUMENTS

| | | | |
|---|---|---|---|
| EP | | 1776460 B2 | 12/2009 |
| WO | | 95/27722 A1 | 10/1995 |
| WO | | 95/30695 A1 | 11/1995 |
| WO | | 96/37223 A1 | 11/1996 |
| WO | | 97/41232 A1 | 11/1997 |
| WO | | 98/36768 A1 | 8/1998 |
| WO | | 00/02582 A2 | 1/2000 |
| WO | | 00/36918 A1 | 6/2000 |
| WO | | 00/62805 A1 | 10/2000 |
| WO | | 01/80889 A1 | 11/2001 |
| WO | | 02/22805 A2 | 3/2002 |
| WO | | 03/048323 A2 | 6/2003 |
| WO | | 2004/059556 A2 | 7/2004 |
| WO | | 2004/059556 A3 | 7/2004 |
| WO | | 2005/085282 A1 | 9/2005 |
| WO | | 2005/087947 A2 | 9/2005 |
| WO | WO 2005/080585 | * | 9/2005 |
| WO | WO 2005/118874 | * | 12/2005 |
| WO | | 2006/020849 A2 | 2/2006 |
| WO | | 2007/001677 A2 | 1/2007 |
| WO | | 2007/046006 A2 | 4/2007 |
| WO | | 2007/084342 A2 | 7/2007 |
| WO | | 2007/095643 A2 | 8/2007 |
| WO | | 2008/089144 A2 | 7/2008 |
| WO | | 2008/143794 A1 | 11/2008 |
| WO | | 2009/002562 A2 | 12/2008 |
| WO | | 2011/020047 A1 | 2/2011 |
| WO | | 2012/040323 A2 | 3/2012 |
| WO | | 2012/175222 A1 | 12/2012 |

OTHER PUBLICATIONS

Database Geneseq Accession No. ADE34596, Jan. 29, 2004 (revised Jun. 11, 2007) "Interleukin 15 receptor alpha gene #SEQ ID 80." (2 pages).

Database Geneseq Accession No. AED08344, Dec. 1, 2005 "Nucleotide sequence of Human interleukin 15 receptor alpha," Sequence 11 from WO 2005/087947A2 (2 pages).

Hsu, C. et al., "Primary human T lymphocytes engineered with a codon-optimized IL-15 gene resistant cytokine withdrawal-induced apoptosis and persist long-term in the absence of exogenous cytokine," 2005, *J. Immunol.*, vol. 175(11), pp. 7226-7234.

Mortier, E., et al., "Natural, proteolytic release of a soluble form of human IL-15 receptor α-chain that behaves as a specific, high affinity IL-15 antagonist," 2004, *J. Immunol.*, vol. 173(3), pp. 1681-1688.

Mortier, E., et al., "Soluble Interleukin-15 receptor a (IL-15Rα)-sushi as a selective and potent agonist of IL-15 action through IL-15Rβ/γ," 2006, *J. Biol. Chem.* vol. 281(3), pp. 1612-1619.

Rubinstein, M., et al., "Converting IL-15 to a superagonist by binding to soluble IL-15Rα," 2006, *Proc. Natl. Acad. Sci.*, vol. 103(24), pp. 9166-9171.

Ruchatz, H., et al., "Soluble IL-15 receptor α-chain administration prevents murine collagen-induced arthritis: A role for IL-15 in development of antigen-induced immunopathology," 1998, *J. Immunol.* vol. 160, pp. 5654-5660.

Smith, X., et al., "Selective blockade of IL-15 by soluble IL-15 receptor α-chain enhances cardiac allograft survival," 2000, *J. Immunol.*, vol. 165(6), pp. 3444-3450.

Strausberg, R., et al., "Generation and initial analysis of more than 15,000 full-length human and mouse cDNA sequences," 2002, *PNAS*, vol. 99(26), pp. 16899-16903.

Dean, Gregg A., et al., "Cloning and expression of feline interleukin 15," *Cytokine* 29 (2005) 77-83.

Dubois et al, "IL-15Rα Recycles and Presents IL-15 in trans to Neighboring Cells," *Immunity*, vol. 17, Nov. 2002, 537-547.

Giron-Michel, et al., "Membrane-Bound and Soluble IL-15/1L-15Rα Complexes Display Differential Signalling and Functions on Human Hematopoietic Progenitors," *Blood* Oct. 1, 2005, vol. 106, No. 7, 2302-2310.

Oh, et al., "IL-15/IL-15Rα-Mediated Avidity Maturation of Memory CD8+ T Cells," *PNAS*, Oct. 19, 2004, vol. 101, No. 42, 15154-15159.

Overwijk, et al., Functions of γC cytokines in immune homeostasis: Current and potential clinical applications, *Clin Immunol* (2009) 132:153-165.

Sandau, et al., "IL-15 is Required for Sustained Lymphopenia-Driven Proliferation and Accumulation of CD8 T Cells," *J Immunol* (2007) 179:120-125.

Stoklasek et al., "Combined IL-15/IL-15Rα Immunotherapy Maximizes IL-15 Activity In Vivo," *The Journal of Immunology*, 2006, 177: 6072-6080.

Williams, et al., "T Cell Immune Reconstitution Following Lymphodepletion," *Semin Immunol* (2007) 19(5):318-330.

Alpdogan et al., 2005, "IL-7 and IL-15: therapeutic cytokines for Immunodeficiency", Trends Immunol; 26:56-64.

Alpdogan et al., 2005, "Interleukin-15 enhances immune reconstitution after allogenic bone marrow transplantation.", Blood; 105:865-873.

Altman, et al., 1996, "Phenotypic analysis of antigen-specific T lymphocytes", Science; 274:94-96.

Armitage et al., 1995, "IL-15 has stimulatory activity for the induction of B cell proliferation and differentiation", J. Immunol; 154:483-490.

Ausubel et al., 1993, Current Protocols in Molecular Biology, John Wiley & Sons, pp. 2.10.1-2.10.16.

Baccala, 2005, "Tumor immunity via homeostatic T cell proliferation: mechanistic aspects and clinical perspectives", Springer Semin Immunopathol published online.

Badoual et al., 2008, "The soluble alpha chain of interleukin-15 receptor: a proinflammatory molecule associated with tumor progression in head and neck cancer," Cancer Res; 68(10):3907-3914.

Bamford et al., 1994, "The interleukin (IL)-2 receptor-beta chain is shared by IL-2 and a cytokine, provisionally designated ii-t, that stimulates Tcell proliferation and the induction of lymphokine-activated killer-cells", Proceedings of the National Academy of Sciences USA; 91:4940-4944.

Bamford et al., 1996, "Interleukin (IL)15/IL-T production by the adult T-cell leukemia cell line HuT-102 is associated with a human T-celilymphotrophic virus type I region /IL-15 fusion message that

(56) References Cited

OTHER PUBLICATIONS lacks many upstream AUGs that normally attenuates IL-15 mRNA translation", Proc. Natl. Acad. Sci. USA; 93:2897-2902.
Bamford et al., 1998, "The 5' untranslated region, signal peptide, and the coding sequence of the carboxyl terminus of IL-15 participate in its multifaceted translational control", Journal of Immunology; 160:4418-4426.
Barzegar et al., 1998, "IL-15 is produced by a subset of human melanomas, and is involved in the regulation of markers of melanoma progression through juxtacrine loops", Oncogene; 16(19):2503-2512.
Becker et al., 2002, "Interleukin 15 is required for proliferative renewal of virus-specific memory CD8 T cells", J Exp Med; 195:1541-1548.
Berard et al., 2003, "IL-15 promotes the survival of naive and memory phenotype CD8(+) T cells", Journal of Immunology; 170:5018-5026.
Bergamaschi et al., 2008, "Intracellular Interaction of Interleukin-15 with Its Receptor α during Production Leads to Mutual Stabilization and Increased Bioactivity", J. Biol. Chem.; 283(7):4189-4199.
Bergamaschi et al., 2012, "Circulating IL-15 exists as heterodimeric complex with soluble IL-15Rα in human and mouse serum", Blood; 120(1): e1-e8.
Berger et al., 2009, "Safety and immunologic effects of IL-15 administration in nonhuman primates," Blood; 114:2417-2426.
Bernard et al., 2004, "Identification of an interleukin-15α receptor-binding site on human interleukin-15," J Biol Chem; 279:24313-24322.
Bindon et al., 1983, "Clearance rates and systemic effects of intravenously administered interleukin 2 (IL-2) containing preparations in human subjects," Br. J. Cancer, 47:123-133.
Brocker, 1997, "Survival of mature CD4 T lymphocytes is dependent on major histocompatibility complex class II-expressina dendritic cells", J Exp Med; 186:1223-1232.
Budagian et al., 2004, "Reverse signaling throlJgh membrane-bound interleukin-15", J Biol Chem; 279:42192-42201.
Burkett et al, 2004, "Coordinate expression and trans presentation of interleukin (IL)-15Ralpha and IL-15 supports natural killer cell and memory CD8+ T cell homeostasis", J Exp Med; 200:825-834.
Burkett et al., 2003, "IL-15R alpha expression on CD8+ T cells is dispensable for T cell Memory", Proc Natl Acad Sci USA; 100:4724-4729.
Burton et al., 1994, "A lymphokine, provisionally designated interleukin-t and produced by a human adult T-cell leukemia line, stimulates T-cell proliferation and the induction of lymphokine-activated killer-cells", Proc Natl Acad Sci USA; 91:4935-4939.
Carson et al., 1994, "Interleukin (IL) 15 is a novel cytokine that activates human natural killer cells via components of the IL-2 receptor", J Exp Med; 180:1395-1403.
Castelli et al., 2004, "Mature dendritic cells can enhance CD8+ cell noncytotoxic anti-HIV responses: the role of IL-15", Blood; 103:2699-2704.
Chapoval et al., 1998, "Combination chemotherapy and IL-15 administration induce permanent tumor regression in a mouse lung tumor model: NK and T cell-mediated effects antagonized by B cells", J Immunol; 161:6977-6984.
Cheever, 2008, "Twelve immunotherapy drugs that could cure cancers", Immunol Rev.; 222:357-368.
Chehimi et al., 1997, "IL-15 enhances immune functions during HIV infection", Journal of Immunology; 158(12):5978-5987.
Chertova et al., 2013, "Characterization and favorable in vivo properties of heterodimeric soluble IL-15•IL-15Rα cytokine compared to IL-15 monomer", J. Biol. Chem.; 288(25):18093-18103.
Chitnis et al., 2003, "Determinants of HIV-Specific CD8 T-cell responses in HIV-infected pediatric patients and enhancement of HIV-gagspecific responses with exogenous IL-15", Clin Immunol; 107:36-45.
Cho et al., 2000, "Homeostasis-stimulated proliferation drives naive T cells to differentiate directly into memory T cells", J Exp Med; 192:549-556.
Cooper et al., 2002, "In vivo evidence for a dependence on interleukin 15 for survival of natural killer cells", Blood; 100:3633-3638.
Cui et al., 2014, "Characterization of the IL-15 niche in primary and secondary lymphoid organs in vivo", Proc. Natl. Acad. Sci. USA; 111(5):1915-1920.
Davis et al., 1991, "Reduction of Immunogenicity and Extension of Circulating Half-life of Peptides and Proteins," Peptide and Protein Drug Delivery, Marcel Deker Inc., New York, pp. 831-864.
De Jong et al., 1996, "Interaction of IL-15 with the shared IL-2 receptor beta and gamma c subunits. The IL-15/beta/gamma c receptor-ligand complex is less stable than the IL-2/beta/gamma c receptor-ligand complex", J Immunol; 156:1339-1348.
Dubois et al., 1999, "Natural splicing of exon 2 of human interleukin-15 receptor α-chain mRNA results in a shortened form with a distinct pattern of expression," J Biol Chem; 274:26978-26984.
Dubois et al., 2008, "Preassociation of IL-15 with IL-15R alpha-IgG1-Fc enhances its activity on proliferation of NK and CD8+/CD44$^{high}$ T cells and its antitumor action", J Immunol.;180(4):2099-2106.
Dudley et al., 2005, "Adoptive cell transfer therapy following nonmyeloablative but lymphodepleting chemotherapy for the treatment of patients with refractory metastatic melanoma", J Clin Oncol; 23:2346-2357.
Dummer et al., 2002, "T cell homeostatic proliferation elicits effective antitumor autoimmunity", J Clin Invest; 110:185-192.
Dunne et al., 2001, "Selective expansion and partial activation of human NK cells and NK receptor-positive T cells by IL-2 and IL-15", J Immunol; 167-3129-3138.
Epardaud et al., 2008, "Interleukin-15/interleukin-15Rα complexes promote destruction of established tumors by reviving tumor-resident CD8+ T cells," Cancer Res; 68:2972-2983.
European Search Report of EP application No. 13195495.0-1402, dated Mar. 28, 2014.
European Search Report of EP application No. 13195499.2-1402, dated Mar. 27, 2014.
Fehniger et al., 2001, "Interleukin 15: biology and relevance to human disease," Blood; 97:14-32.
Ferrari-Lacraz et al., 2004, "Targeting IL-15 receptor-bearing cells with an antagonist mutant IL-15/Fc protein prevents disease development and progression in murine collagen-induced arthritis", J Immunol; 173:5818-5826.
Fewkes et al., 2010, "Novel gamma-chain cytokines as candidate immune modulators in immune therapies for cancer," J Cancer; 16:392-398.
Fischer et al., 1997, "A bioactive designer cytokine for human hematopoietic progenitor cell expansion", Nat Biotechnol; 15(2):142-145.
Forcina et al., 2004, "Interleukin-15 modulates interferon-gamma and betachemokine production in patients with HIV infection: implications for immune-based therapy", Cytokine; 25:283-290.
Giri et al., 1994, "Utilization of the beta and gamma chains of the IL-2 receptor by the novel cytokine IL-15", EMBO J; 13:2822-2830.
Giri et al., 1995, "Identification and cloning of a novel IL-15 binding protein that is structurally related to the alpha chain of the IL-2 receptor", EMBO J; 15:3654-3633.
Giri et al., 1995, "IL-15, a novel T cell growth factor that shares activities and receptor components with IL-2", J Leukocyte Biol; 57:763-766.
Goldrath et al., 2002, "Cytokine requirements for acute and basal homeostatic proliferation of naive and memory CD8+ T cells", J Exp Med; 195:1515-1522.
Goldrath et al., 2000, "Low-affinity ligands for the TCR drive proliferation of mature CD8+ Tcells in lymphopenic hosts", Immunity; 11:183-190.
Grabstein et al., 2004, "Cloning of a T cell growth factor that interacts with the beta chain of the interleukin-2 receptor", Science; 264:965-968.

(56) References Cited

OTHER PUBLICATIONS

International Preliminary Report on Patentablility of International application No. PCT/US2008/008084, dated Jan. 5, 2010.
International Search Report of International application No. PCT/US2006/19403, dated May 11, 2007.
International Search Report of International application No. PCT/US2008/008084, dated Dec. 30, 2008.
International Search Report on International application No. PCT/US2013/066424, dated May 8, 2014.
Jalah et al., 2007, "Efficient systemic expression of bioactive IL-15 in mice upon delivery of optimized DNA expression plasmids", DNA and Cell Biology; 26(12):827-840.
Jensen et al., 2012, "Structural analysis of N- and O-glycans released from glycoproteins", Nature Protocols, 7(7):1299-1310.
Johnston et al., 1995, "Tyrosine phosphorylation and activation of STAT5, STAT3, and Janus kinases by interleukins 2 and 15", Proc Natl Acad Sci U S A. 92(19):8705-8709.
Judge et al., 2002, "Interleukin 15 controls both proliferation and survival of a subset of memory-phenotype CD8(+) T Cells", J Exp Med; 196:935-946.
Jung et al., 2002, "In vivo depletion of CD11c(+) dendritic cells abrogates priming of CD8(+) T cells by exogenous cell-associated antiqens", Immunity; 17:211-220.
Kassiotis et al., 2002, "Impairment of immunological memory in the absence of MHC despite survival of memory T cells", Nat Immunol; 3:244-250.
Kennedy et al., 2000, "Reversible defects in natural killer and memory CD8 T cell lineages in Interleukin-15-deficient mice", J Exp Med; 191:771-780.
Khan et al., 1996, "IL-15 augments CD8+ T cell-mediated immunity against Toxoplasma gondii infection in mice", J Immunol; 157(5):2103-2108.
Khan et al., 2002, "Treatment with soluble interleukin-15Rα exacerbates intracellular parasitic infection by blocking the development of memory CD8+ T cell response," J Exp Med; 195(11):1463-1470.
Kieper et al., 2000, "Homeostatic expansion and phenotypic conversion of naive T cells in response to self peptide/MHC ligands", PNAS; 96:13306-13311.
Kim et al., 1998, "Generation of mucosal cytotoxic T cells against soluble protein by tissue specific environmental and costimulatory signals", Proc Natl Acad Sci USA; 95:10814-10819.
Kishimoto, 2010, "IL-6: from its discovery to clinical applications", International Immunology; 22(5):347-352.
Klebanoff et al., 2004, "IL-15 enhances the in vivo antitumor activity of tumorreactive CD8+ T cells", Proc Natl Acad Sci USA; 101:1969-1974.
Kobayashi et al., 2000, "Differences in biodistribution, pharmacokinetics, and tumor targeting between interleukins 2 and 15", Cancer Research; 60:3577-3583.
Kobayashi et al., 2005, "Role of trans-cellular IL-15 presentation in the activation of NK cell-mediated killing, which leads to enhanced tumor immunosurveillance", Blood; 105(2): 721-727.
Koka et al., 2003, "Interleukin (IL)-15R[alpha]-deficient natural killer cells survive in normal but not IL-15R[alpha]-deficient mice", J Exp Med; 197:977-984.
Krause et al., 1996, "Genomic structure and chromosomal localization of the human interleukin 15 gene (IL-15)", Cytokine. 8(9):667-674.
Ku et al., 2000, "Control of homeostasis of CD8+ memory T cells by opposing cytokines", Science; 288:675-678.
Kutzler et al., 2005, "Coimmunization with an optimized IL-15 plasmid results in enhanced function and longevity of CD8 T cells that are partially independent of CD4 T cell help," J Immunol; 175:112-123.
Lodolce et al., 1998, "IL-15 receptor maintains lymphoid homeostasis by supporting lymphocyte homing and proliferation", Immunity; 9:669-676.
Lodolce et al., 2001, "T cell independent interleukin 15R alpha signals are required for bystander proliferation", J Exp Med; 194:1187-1194.
Lum et al., 2004, "Differential Effects of Interleukin-7 and Interleukin-15 on NK Cell Anti-Human Immunodeficiency Virus Activity", J Viral; 78:6033-6042.
Lyons et al., 1994, "Determination of lymphocyte division by flow cytometry", J Immunol Methods. 2;171(1):131-137.
Maeurer et al., 2000, "Interleukin-7 or interleukin-15 enhances survival of mycobacterium tuberculosis-infected mice", Infect Immun; 68:2962-2970.
Masopust et al., 2001, "Direct analysis of the dynamics of the intestinal mucosa CD8 T cell response to systemic virus infection", J Immunol; 166:2348-2356.
Mastroianni et al., 2000, "Interleukin-15 enhances neutrophil functional activity in patients with human immunodeficiency virus infection", Blood; 96:1979-1984.
Matsumoto et al., 2003, "On-column refolding and characterization of soluble human interleukin-15 receptor alpha-chain produced in *Escherichia coli*", Protein Expr Purif; 31(1):64-71.
Mlecnik et al., 2014, "Functional network pipeline reveals genetic determinants associated with in situ lymphocyte proliferation and survival of cancer patients", Sci Transl Med.; 6(228):228ra37.
Mueller et al., 2003, "IL-15 enhances survival and function of HIV-specific CD8+ T cells", Blood; 101(3):1024-1029.
Murali-Krishna et al., 1999, "Persistence of memory CD8 T cells in MHC class I-deficient mice", Science; 286:1377-1381.
Nasioulas et al., 1994, "Elements distinct from human immunodeficiency virus type 1 splice sites are responsible for the Rev dependence of env mRNA", J Virol, 68(5):2986-2993.
Nguyen et al., 2000, "TNF receptor 1 (TNFR1) and CD95 are not required for T cell deletion after virus infection but contribute to peptide-induced deletion under limited conditions", Eur J Immunol; 30:683-688.
Nishimura et al., 2005, "A novel autoregulatory mechanism for transcriptional activation of the IL-15 gene by a nonsecretable isoform of IL-15 generated by alternative splicing", FASEB J; 19:19-28.
Notice of Allowance and Fees Due of U.S. Appl. No. 11/435,497, dated Oct. 19, 2011.
Notice of Allowance and Fees Due of U.S. Appl. No. 13/368,605, dated Sep. 11, 2014.
Oehen et al., 1998, "Differentiation of naive CTL to effector and memory CTL: correlation of effector function with phenotype and cell division", J Immunol; 161;5338-5346.
Office Action of U.S. Appl. No. 11/435,497, dated Feb. 25, 2009.
Office Action of U.S. Appl. No. 11/435,497, dated Jan. 13, 2011.
Office Action of U.S. appl. No. 11/435,497, dated Jun. 27, 2008.
Office Action of U.S. Appl. No. 11/435,497, dated Jun. 27, 2011.
Office Action of U.S. Appl. No. 11/435,497, dated Jun. 7, 2010.
Office Action of U.S. Appl. No. 11/435,497, dated Oct. 30, 2009.
Office Action of U.S. Appl. No. 13/368,605, dated Apr. 9, 2014.
Oh et al., 2003, "Coadministration of HIVvaccine vectors with vaccinia viruses expressing IL-15 but not IL-2 induces long-lasting cellular immunity", PNAS; 100:3392-3397.
Ohteki et al., 2001, "Critical role of IL-15-IL-15R for antigen-presenting cell functions in the innate immune response", Nat Immunol; 2:1138-1143.
Park et al., 2004, "Follicular dendritic cells produce IL-15 that enhances germinal center B cell proliferation in membrane-bound form", J Immunol; 173:6676-6683.
Pereno et al., 2000, "IL-15/IL-15Ralpha intracellular trafficking in human melanoma cells and signal transduction through the IL-15Ralpha", Oncogene. 19(45):5153-5162.
Pettit et al., 1997, "Structure-function studies of interleukin 15 using site-specific mutagenesis, polyethylene glycol conjugation, and homology modeling", J Biol Chem; 272(4):2312-2318.
Pflanz et al., 1999, "A fusion protein of interleukin-11 and soluble interleukin-11 receptor acts as a superagonist on cells expressing gp130", FESB Lett; 450:117-122.
Porter et al., 2005, "T-cell reconstitution and expansion after hematopoietic stem cell transplantation: T it up!", Bone Marrow Transplant; 35:935-942.
Prlic et al., 2003, "In vivo survival and homeostatic proliferation of natural killer cells", J Exp Med; 197:967-976.

(56) References Cited

OTHER PUBLICATIONS

Roychowdhury et al., 2004, "Failed adoptive immunotherapy with tumorspecific T cells: reversal with low-dose interleukin 15 but not low-dose interleukin 2", Cancer Res; 64:8062-8067.
Rubinstein et al., 2002, "Systemic administration of IL-15 augments the antigen-specific primary CD8+ T Cell response following vaccination with peptide-pulsed dendritic cells", J Immunol; 169:4928-4935.
Ruckert et al., 2003, "Dendritic cell-derived IL-15 controls the induction of CD8 T cell immune responses", Eur J Immunol; 33:3493-3503.
Sandau et al., 2004, "Transpresentation of IL-15 by bone marrow-derived cells necessitates expression of IL-15 and IL-15R by the same cells", J Immunol; 173(11):6537-6541.
Sato et al., 2007, "The IL-15/IL-15 Rα on cell surfaces enables sustained IL-15 activity and contributes to the long survival of CD8 memory T cells", Proc Natl Acad Sci USA; 104(2):588-593.
Scheller et al., 2006, "Interleukin-6 and its receptor: from bench to bedside", Med Microbiol Immunol; 195:173-183.
Schluns et al., 2000, "Interleukin-7 mediates the homeostasis of naive and memory CD8 T cells in vivo", Nat Immunol; 1:426-432.
Schluns et al., 2002, "Cutting edge: requirement for IL-15 in the generation of primary and memory antigen specific CD8 T cells", J Immunol; 168:4827-4831.
Schluns et al., 2004, "Distinct cell types control lymphoid subset development by means of IL-15 and IL-15 receptor alpha expression", Proc Natl Acad Sci USA; 101:5616-5621.
Schluns et al., 2004, "Trans-regulation of memory CD8 T cell proliferation by IL-15Ra+ bone marrow-derived cells", Blood; 103(3):988-994.
Schluns et al., 2005, "The roles of interleukin-15 receptor α: Trans-presentation, receptor component, or both?" Int J Biochem Cell Biol; 37:1567-1571.
Schneider et al., 1997, Inactivation of the human immunodeficiency virus type 1 inhibitory elements allows Rev-independent expression of Gag and Gag/protease and particle formation, J Virol, 71(7):4892-4903.
Schwartz et al., 1992, "Mutational inactivation of an inhibitory sequence in human immunodeficiency virus type 1 results in Rev-independent gag expression", J Virol, 66(12):7176-7182.
Southern and Berg, 1982, "Transformation of mammalian cells to antibiotic resistance with a bacterial gene under control of the SV40 early region promoter", J Mol Appl Genet, 1:327-341.
Supplementary European Search Report of EP application No. 06784439.9-2401, dated Apr. 22, 2009.
Tagaya et al., 1997, "Generation of secretable and nonsecretable interleukin 15 isoforms through alternate usage of signal problems", Proc Natl Acad Sci USA, 94:14444-14449.
Tan et al., 2000, "Interleukin (IL)-15 and IL-7 jointly regulate homeostatic proliferation of memory phenotype CD8+ cells but are not required for memory phenotype CD4+ cells", J Exp Med; 195:1523-1532.

Tsunobuchi et al., 2000, "A protective role of interleukin-15 in a mouse model for systemic infection with herpes simplex virus," Virology, 275:57-66.
Umemura et al., 2001, "Overexpression of IL-15 in vivo enhances protection against *Mycobacterium bovis* bacillus Calmette-Guerin infection via augmentation of NK and T cytotoxic 1 responses", J Immunol; 167:946-956.
Van Belle et al., 2005, "IL-15 and IL-15Rα in CD4+ T cell immunity," Arch Immunol Ther Exp; 53(2):115-126.
Villinger et al., 2004, "IL-15 is superior to IL-2 in the generation of long-lived antigen specific memory CD4 and CD8 T cells in rhesus macaques", Vaccine; 22:3510-3521.
Waldmann et al., 1999, "The multifaceted regulation of interleukin-15 expression and the role of this cytokine in NK cell differentiation and host response to intracellular pathogens," Annu Rev Immunol., vol. 17:19-49.
Waldmann et al., 2001, "Contrasting roles of IL-2 and IL-15 in the life and death of lymphocytes: implications for immunotherapy," Immunity, vol. 14:105-110.
Waldmann, T.A., 2006, "The biology of interleukin-2 and interleukin-15: implications for cancer therapy and vaccine design," Nat Rev Immunol., vol. 6:595-601.
Wang et al., 1987, "The interleukin 2 receptor", Journal of Experimental Medicine; 166:1055-1069.
Warren et al., 1996, "Analysis of the costimulatory role of IL-2 and IL-15 in initiating proliferation of resting (CD56dim) human NK cells", J Immunol; 156:3254-3259.
Wei et al., 2001, "The Sushi domain of soluble IL-15 receptor α is essential for binding IL-15 and inhibiting inflammatory and allogenic responses in vitro and in vivo," J Immunol., vol. 167:277-282.
Written Opinion of International application No. PCT/US2006/19403, dated May 11, 2007.
Written Opinion of International application No. PCT/US2008/008084, dated Dec. 30, 2008.
Written Opinion on International application No. PCT/US2013/066424, dated May 8, 2014.
Wrzesinski et al., 2005, "Less is more: lymphodepletion followed by hematopoietic stem cell transplant augments adoptive T-cell-based antitumor immunotherapy", Curr Opin Immunol; 17:195-201.
Wysocka et al., 2004, "Enhancement of the host immune responses in cutaneous T-cell lymphoma by CpG oligodeoxynucleotides and IL-15", Blood; 104:4142-4149.
Zammit et al., 2005, "Dendritic cells maximize the memory CD8 T cell response to infection", Immunity. 22(5):561-70.
Zeng et al., 2005, "Synergy of IL-21 and IL-15 in regulating CD8+ T cell expansion and Function", J Exp Med; 201:139-148.
Shanmugham et al., 2006, "IL-15 an immunoregulatory and anti-cancer cytokine. Recent advances", Journal of Experimental Cancer Research, 25(4):529-536.

\* cited by examiner

```
                                    signal peptide                    propeptide
h-IL15  :   1  MRISKPHLRSISIQCYLCLLLNSHFLTEAGIHVFILGCFSAGLPKTEANWVNVISDLKKI   60
rh-IL15 :   1  MRISKPHLRSVSIQCYLCLLLNSHFLTEAGIHVFILGCFSAGLPKTEANWVNVISDLKKI   60
               *******:********************************************** h-IL15  :  61  EDLIQSMHIDATLYTESDVHPSCKVTAMKCFLLELQVISLESGDASIHDTVENLIILANN  120
rh-IL15 :  61  EDLIQSMHIDATLYTEDDVHPSCKVTAMKCFLLELQVIHHEGDDPIHDTVENLIILANN  120
               **************.******************:* .. ********* h-IL15  : 121  SLSSNGNVTESGCKECEELEEKNIKEFLQSFVHIVQMFINTS  162
rh-IL15 : 121  FLSSNGNTTESGCKECEELEEKNIKEFLQSFVHIVQMFINTS  162
               .******.*********************************
```

|  | tPA signal peptide | tPA propeptide | Mature Human IL15 |
|---|---|---|---|
| tPA2: | ..F V S P S | Q E I H A R F R R G A R A | N W V N V I S D |
| tPA5: | ..F V S P S | Q E I H A R F R R G · R A | N W V N V I S D |
| tPA6: | ..F V S P S | Q E I H A R F R R G A R · | N W V N V I S D |
| tPA7: | ..F V S P S | Q E I H A R F R R G · R · | N W V N V I S D |

Furin cleavage

Human IL-15 receptor alpha OPT
ATGGCCCCGAGGCGGGCGCGAGGCTGCCGGACCCTCGGTCTCCCGGCGCTGCTA
CTGCTCCTGCTGCTCCGGCCGCCGGCGACGCGGGGCATCACGTGCCCGCCCCCA
TGTCCGTGGAGCACGCAGACATCTGGGTCAAGAGCTACAGCTTGTACTCCCGGG
AGCGGTACATCTGCAACTCGGGTTTCAAGCGGAAGGCCGGCACGTCCAGCCTGA
CGGAGTGCGTGTTGAACAAGGCCACGAATGTCGCCCACTGGACGACCCCCTCGC
TCAAGTGCATCCGCGACCCGGCCCTGGTTCACCAGCGGCCCGCGCCACCCTCCAC
CGTAACGACGGCGGGGGTGACCCCGCAGCCGGAGAGCCTCTCCCCGTCGGGAAA
GGAGCCCGCCGCGTCGTCGCCCAGCTCGAACAACACGGCGGCCACAACTGCAGC
GATCGTCCCGGGCTCCCAGCTGATGCCGTCGAAGTCGCCGTCCACGGGAACCAC
GGAGATCAGCAGTCATGAGTCCTCCCACGGCACCCCCTCGCAAACGACGGCCAA
GAACTGGGAACTCACGGCGTCCGCCTCCCACCAGCCGCCGGGGGTGTATCCGCA
AGGCCACAGCGACACCACGGTGGCGATCTCCACGTCCACGGTCCTGCTGTGTGG
GCTGAGCGCGGTGTCGCTCCTGGCGTGCTACCTCAAGTCGAGGCAGACTCCCCCG
CTGGCCAGCGTTGAGATGGAGGCCATGGAGGCTCTGCCGGTGACGTGGGGGACC
AGCAGCAGGGATGAGGACTTGGAGAACTGCTCGCACCACCTATAATGA MAPRRARGCRTLGLPALLLLLLRPPATRGITCPPPMSVEH
ADIWVKSYSLYSRERYICNSGFKRKAGTSSLTECVLNKATN
VAHWTTPSLKCIRDPALVHQRPAPPSTVTTAGVTPQPESLS
PSGKEPAASSPSSNNTAATTAAIVGSQLMPSKSPSTGTTE
ISSHESSHGTPSQTTAKNWELTASASHQPPGVYPQGHSDTT
VAISTSTVLLCGLSAVSLLACYLKSRQTPPLASVEMEAMEAL
PVTWGTSSRDEDLENCSHHL**

```
  1 ATG GCC CCG AGG CGG GCG CGA GGC TGC CGG ACC CTC GGT CTC CCG GCG CTG CTA CTG
  1▶ M   A   P   R   R   A   R   G   C   R   T   L   G   L   P   A   L   L   L

58 CTC CTG CTG CTC CGG CCG CCG GCG ACG CGG GGC ATC ACG TGC CCG CCC CCC ATG TCC
 20▶ L   L   L   L   R   P   P   A   T   R   G   I   T   C   P   P   P   M   S

115 GTG GAG CAC GCA GAC ATC TGG GTC AAG AGC TAC AGC TTG TAC TCC CGG GAG CGG TAC
 39▶ V   E   H   A   D   I   W   V   K   S   Y   S   L   Y   S   R   E   R   Y

172 ATC TGC AAC TCG GGT TTC AAG CGG AAG GCC GGC ACG TCC AGC CTG ACG GAG TGC GTG
 58▶ I   C   N   S   G   F   K   R   K   A   G   T   S   S   L   T   E   C   V

229 TTG AAC AAG GCC ACG AAT GTC GCC CAC TGG ACG ACC CCC TCG CTC AAG TGC ATC CGC
 77▶ L   N   K   A   T   N   V   A   H   W   T   T   P   S   L   K   C   I   R

286 GAC CCG GCC CTG GTT CAC CAG CGG CCC GCG CCA CCC TCC ACC GTA ACG ACG GCG GGG
 96▶ D   P   A   L   V   H   Q   R   P   A   P   P   S   T   V   T   T   A   G

343 GTG ACC CCG CAG CCG GAG AGC CTC TCC CCG TCG GGA AAG GAG CCC GCC GCG TCG TCG
115▶ V   T   P   Q   P   E   S   L   S   P   S   G   K   E   P   A   A   S   S

400 CCC AGC TCG AAC AAC ACG GCG GCC ACA ACT GCA GCG ATC GTC CCG GGC TCC CAG CTG
134▶ P   S   S   N   N   T   A   A   T   T   A   A   I   V   P   G   S   Q   L

457 ATG CCG TCG AAG TCG CCG TCC ACG GGA ACC ACG GAG ATC AGC AGT CAT GAG TCC TCC
153▶ M   P   S   K   S   P   S   T   G   T   T   E   I   S   S   H   E   S   S

514 CAC GGC ACC CCC TCG CAA ACG ACG GCC AAG AAC TGG GAA CTC ACG GCG TCC GCC TCC
172▶ H   G   T   P   S   Q   T   T   A   K   N   W   E   L   T   A   S   A   S

571 CAC CAG CCG CCG GGG GTG TAT CCG CAA GGC CAC AGC GAC ACC ACG GTG GCG ATC TCC
191▶ H   Q   P   P   G   V   Y   P   Q   G   H   S   D   T   T   V   A   I   S

628 ACG TCC ACG GTC CTG CTG TGT GGG CTG AGC GCG GTG TCG CTC CTG GCG TGC TAC CTC
210▶ T   S   T   V   L   L   C   G   L   S   A   V   S   L   L   A   C   Y   L

685 AAG TCG AGG CAG ACT CCC CCG CTG GCC AGC GTT GAG ATG GAG GCC ATG GAG GCT CTG
229▶ K   S   R   Q   T   P   P   L   A   S   V   E   M   E   A   M   E   A   L

742 CCG GTG ACG TGG GGG ACC AGC AGC AGG GAT GAG GAC TTG GAG AAC TGC TCG CAC CAC
248▶ P   V   T   W   G   T   S   S   R   D   E   D   L   E   N   C   S   H   H

799 CTA TAA TGA
267▶ L   *   *
    ──────────▶
```

Human soluble IL-15 receptor alpha OPT
ATGGCCCCGAGGCGGGCGCGAGGCTGCCGGACCCTCGGTCTCCCGGCGCTGCTA
CTGCTCCTGCTGCTCCGGCCGCCGGCGACGCGGGGCATCACGTGCCCGCCCCCA
TGTCCGTGGAGCACGCAGACATCTGGGTCAAGAGCTACAGCTTGTACTCCCGGG
AGCGGTACATCTGCAACTCGGGTTTCAAGCGGAAGGCCGGCACGTCCAGCCTGA
CGGAGTGCGTGTTGAACAAGGCCACGAATGTCGCCCACTGGACGACCCCCTCGC
TCAAGTGCATCCGCGACCCGGCCCTGGTTCACCAGCGGCCCGCGCCACCCTCCAC
CGTAACGACGGCGGGGGTGACCCCGCAGCCGGAGAGCCTCTCCCCGTCGGGAAA
GGAGCCCGCCGCGTCGTCGCCCAGCTCGAACAACACGGCGGCCACAACTGCAGC
GATCGTCCCGGGCTCCCAGCTGATGCCGTCGAAGTCGCCGTCCACGGGAACCAC
GGAGATCAGCAGTCATGAGTCCTCCCACGGCACCCCCTCGCAAACGACGGCCAA
GAACTGGGAACTCACGGCGTCCGCCTCCCACCAGCCGCCGGGGGTGTATCCGCA
AGGCCACAGCGACACCACGTAATGA

```
M  A  P  R  R  A  R  G  C  R  T  L  G  L  F  A  L  L  L  L  L  R  P  P  A  T
R  G  I  T  C  P  P  P  M  S  V  E  H  A  D  I  W  V  K  S  Y  S  L  Y  S  R  E  R
Y  I  C  N  S  G  F  K  R  K  A  G  T  S  S  L  T  E  C  V  L  N  K  A  T  N  V  A
H  W  T  T  P  S  L  K  C  I  R  D  P  A  L  V  H  Q  R  P  A  P  P  S  T  V  T  T
A  G  V  T  P  Q  P  E  S  L  S  P  S  G  K  E  P  A  A  S  S  P  S  S  N  N  T  A
A  T  T  A  A  I  V  P  G  S  Q  L  M  P  S  K  S  P  S  T  G  T  T  E  I  S  S  H
E  S  S  H  G  T  P  S  Q  T  T  A  K  N  W  E  L  T  A  S  A  S  H  Q  P  P  G  V
Y  P  Q  G  H  S  D  T  T  *  *
```

Effects on NK and T cells (liver)

Effector T cells in the spleen

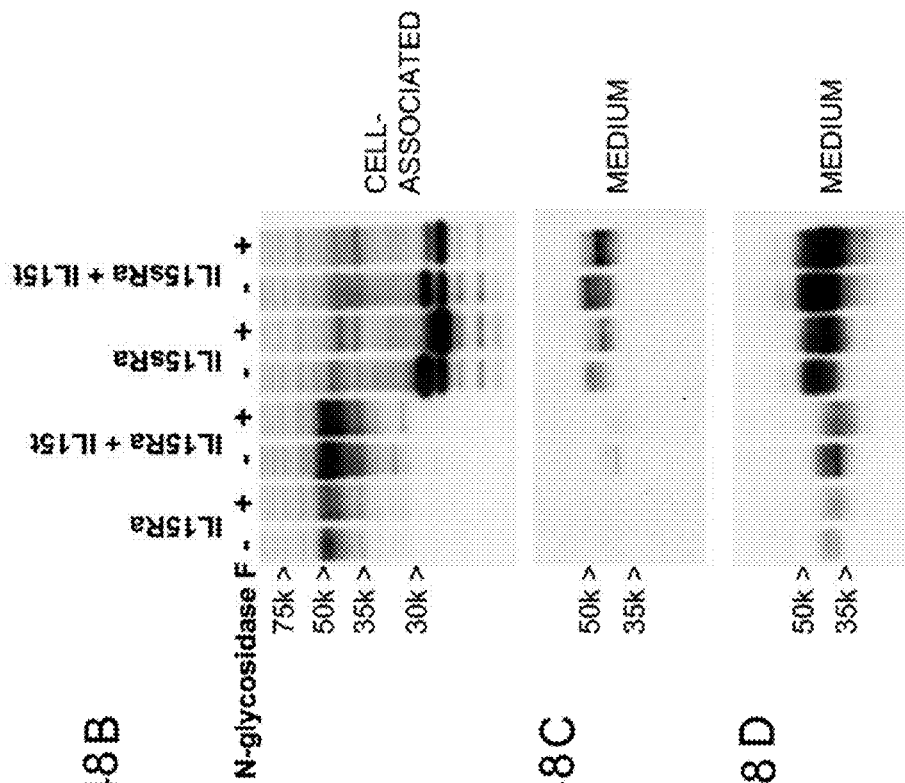
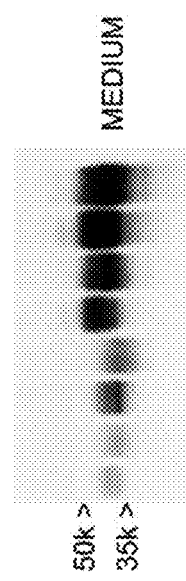
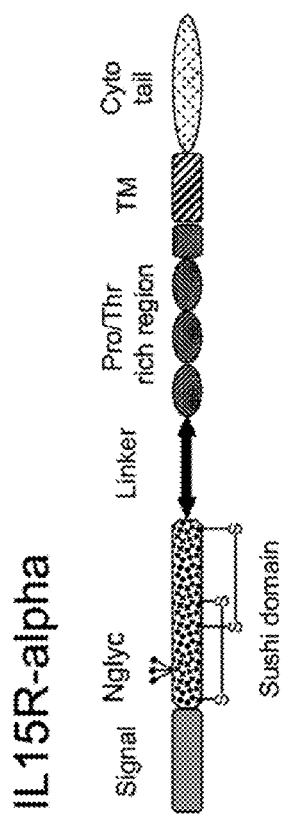
Figure 48A
Figure 48B
Figure 48C
Figure 48D

SEQUENCE LISTING

```
<160> NUMBER OF SEQ ID NOS: 53

<210> SEQ ID NO 1
<211> LENGTH: 489
<212> TYPE: DNA
<213> ORGANISM: Artificial Sequence
<220> FEATURE:
<223> OTHER INFORMATION: Description of Artificial Sequence:synthetic
      human wild-type interleukin-15 (IL-15) nucleic acid sequence

<400> SEQUENCE: 1
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtctggag atgcaagtat tcatgataca gtagaaaatc tgatcatcct agcaaacaac     360
agtttgtctt ctaatgggaa tgtaacagaa tctggatgca agaatgtgat ggaactggag     420
gaaaaaaata ttaaagaatt tttgcagagt tttgtacata ttgtccaaat gttcatcaac     480
acttcttga                                                              489

<210> SEQ ID NO 2
<211> LENGTH: 162
<212> TYPE: PRT
<213> ORGANISM: Homo sapiens
<220> FEATURE:
<223> OTHER INFORMATION: human wild-type interleukin-15 (IL-15)

<400> SEQUENCE: 2

Met Arg Ile Ser Lys Pro His Leu Arg Ser Ile Ser Ile Gln Cys Tyr
  1               5                  10                  15

Leu Cys Leu Leu Leu Asn Ser His Phe Leu Thr Glu Ala Gly Ile His
                 20                  25                  30

Val Phe Ile Leu Gly Cys Phe Ser Ala Gly Leu Pro Lys Thr Glu Ala
             35                  40                  45

Asn Trp Val Asn Val Ile Ser Asp Leu Lys Lys Ile Glu Asp Leu Ile
         50                  55                  60

Gln Ser Met His Ile Asp Ala Thr Leu Tyr Thr Glu Ser Asp Val His
     65                  70                  75                  80

Pro Ser Cys Lys Val Thr Ala Met Lys Cys Phe Leu Leu Glu Leu Gln
                 85                  90                  95
```

```
Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 3
<211> LENGTH: 489
<212> TYPE: DNA
<213> ORGANISM: Artificial Sequence
<220> FEATURE:
<223> OTHER INFORMATION: Description of Artificial Sequence:synthetic
      human improved IL-15 (opt1)

<400> SEQUENCE: 3
atgcggatct cgaagccgca cctgcggtcg atatcgatcc agtgctacct gtgcctgctc      60
ctgaactcgc acttcctcac ggaggccggt atacacgtct tcatcctggg ctgcttctcg     120 gcgggctgc cgaagacgga ggcgaactgg gtgaacgtga tctcggacct gaagaagatc      180
gaggacctca tccagtcgat gcacatcgac gcgacgctgt acacggagtc ggacgtccac     240
ccgtcgtgca aggtcacggc gatgaagtgc ttcctcctgg agctccaagt catctcgctc     300
gagtcggggg acgcgtcgat ccacgacacg gtggagaacc tgatcatcct ggcgaacaac     360
tcgctgtcgt cgaacgggaa cgtcacggag tcgggctgca aggagtgcga ggagctggag     420
gagaagaaca tcaaggagtt cctgcagtcg ttcgtgcaca tcgtccagat gttcatcaac     480
acgtcgtga                                                              489

<210> SEQ ID NO 4
<211> LENGTH: 489
<212> TYPE: DNA
<213> ORGANISM: Artificial Sequence
<220> FEATURE:
<223> OTHER INFORMATION: Description of Artificial Sequence:synthetic
      human improved IL-15 (opt2)

<400> SEQUENCE: 4
atgaggatca gcaagcccca cctgaggagc atcagcatcc agtgctacct gtgcctgctg      60
ctgaacagcc acttcctgac cgaggccggt atacacgtgt tcatcctggg ctgctttagc     120
gccggactgc ccaagaccga ggccaattgg gtgaacgtga tcagcgacct gaagaagatc     180
gaggacctca tccagagcat gcacatcgac gccaccctgt acaccgagag cgatgtgcac     240
cccagctgta aggtgaccgc catgaagtgc tttctgctgg agctgcaagt gatcagcctg     300
gagagcggcg acgccagcat ccacgacacc gtggagaacc tgatcatcct ggccaacaac     360
agcctgagca gcaacggcaa tgtgaccgag agcggctgta aggagtgtga ggagctggag     420
gagaagaaca tcaaggagtt tctgcagagc ttcgtgcaca tcgtgcagat gttcatcaac     480
accagctga                                                              489

<210> SEQ ID NO 5
<211> LENGTH: 108
<212> TYPE: DNA
<213> ORGANISM: Artificial Sequence
<220> FEATURE:
```

```
<223> OTHER INFORMATION: Description of Artificial Sequence:tissue
      plasminogen activator (tPA) signal and propeptide
      tPA2
<220> FEATURE:
<221> NAME/KEY: sig_peptide
<222> LOCATION: (1)..(69)
<223> OTHER INFORMATION: tPA signal
<220> FEATURE:
<221> NAME/KEY: misc_feature
<222> LOCATION: (70)..(108)
<223> OTHER INFORMATION: tPA2 propeptide

<400> SEQUENCE: 5
atggatgcaa tgaagagagg gctctgctgt gtgctgctgc tgtgtggagc agtcttcgtt      60
tcgcccagcc aggaaatcca tgcccgattc agaagaggag ccagagcg                 108

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence:synthetic
      tissue plasminogen activator (tPA) signal and propeptide
      tPA2
<220> FEATURE:
<221> NAME/KEY: SIGNAL
<222> LOCATION: (1)..(23)
<223> OTHER INFORMATION: tPA signal peptide
<220> FEATURE:
<221> NAME/KEY: PROPEP
<222> LOCATION: (24)..(35)
<223> OTHER INFORMATION: tPA2 propeptide
<220> FEATURE:
<221> NAME/KEY: MISC_FEATURE
<222> LOCATION: (36)..(36)
<223> OTHER INFORMATION: amino acid linker between tPA signal
      peptide/tPA2 propeptide and IL-15

<400> SEQUENCE: 6

Met Asp Ala Met Lys Arg Gly Leu Cys Cys Val Leu Leu Leu Cys Gly
  1               5                  10                  15

Ala Val Phe Val Ser Pro Ser Gln Glu Ile His Ala Arg Phe Arg Arg
             20                  25                  30

Gly Ala Arg Ala
         35

<210> SEQ ID NO 7
<211> LENGTH: 102
<212> TYPE: DNA
<213> ORGANISM: Artificial Sequence
<220> FEATURE:
<223> OTHER INFORMATION: Description of Artificial Sequence:synthetic
      tissue plasminogen activator (tPA) signal and propeptide tPA5
<220> FEATURE:
<221> NAME/KEY: sig_peptide
<222> LOCATION: (1)..(69)
<223> OTHER INFORMATION: tPA signal
<220> FEATURE:
<221> NAME/KEY: misc_feature
<222> LOCATION: (70)..(102)
<223> OTHER INFORMATION: tPA5 propeptide

<400> SEQUENCE: 7
atggatgcaa tgaagagagg gctctgctgt gtgctgctgc tgtgtggagc agtcttcgtt      60
tcgcccagcc aggaaatcca tgcccgattc agaagaggag cg                       102

<210> SEQ ID NO 8
<211> LENGTH: 34
<212> TYPE: PRT
```

<213> ORGANISM: Artificial Sequence
<220> FEATURE:
<223> OTHER INFORMATION: Description of Artificial Sequence:synthetic
      tissue plasminogen activator (tPA) signal and propeptide
      tPA5
<220> FEATURE:
<221> NAME/KEY: SIGNAL
<222> LOCATION: (1)..(23)
<223> OTHER INFORMATION: tPA signal peptide
<220> FEATURE:
<221> NAME/KEY: PROPEP
<222> LOCATION: (24)..(34)
<223> OTHER INFORMATION: tPA5 propeptide

<400> SEQUENCE: 8

Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
            20                  25                  30

Gly Ala

<210> SEQ ID NO 9
<211> LENGTH: 453
<212> TYPE: DNA
<213> ORGANISM: Artificial Sequence
<220> FEATURE:
<223> OTHER INFORMATION: Description of Artificial Sequence:synthetic
      tPA2 + human improved IL-15(opt1)

<400> SEQUENCE: 9
atggatgcaa tgaagagagg gctctgctgt gtgctgctgc tgtgtggagc agtcttcgtt    60
tcgcccagcc aggaaatcca tgcccgattc agaagaggag ccagagcgaa ctgggtgaac   120
gtgatctcgg acctgaagaa gatcgaggac ctcatccagt cgatgcacat cgacgcgacg   180
ctgtacacgg agtcggacgt ccacccgtcg tgcaaggtca cggcgatgaa gtgcttcctc   240
ctggagctcc aagtcatctc gctcgagtcg ggggacgcgt cgatccacga cacggtggag   300
aacctgatca tcctggcgaa caactcgctg tcgtcgaacg ggaacgtcac ggagtcgggc   360
tgcaaggagt gcgaggagct ggaggagaag aacatcaagg agttcctgca gtcgttcgtg   420
cacatcgtcc agatgttcat caacacgtcg tga                               453

<210> SEQ ID NO 10
<211> LENGTH: 150
<212> TYPE: PRT
<213> ORGANISM: Artificial Sequence
<220> FEATURE:
<223> OTHER INFORMATION: Description of Artificial Sequence:synthetic
      tPA2 + human improved IL-15(opt1)

<400> SEQUENCE: 10

Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
            20                  25                  30

Gly Ala Arg Ala Asn Trp Val Asn Val Ile Ser Asp Leu Lys Lys Ile
        35                  40                  45

Glu Asp Leu Ile Gln Ser Met His Ile Asp Ala Thr Leu Tyr Thr Glu
 50                  55                  60

Ser Asp Val His Pro Ser Cys Lys Val Thr Ala Met Lys Cys Phe Leu
 65                  70                  75                  80

Leu Glu Leu Gln Val Ile Ser Leu Glu Ser Gly Asp Ala Ser Ile His
                85                  90                  95

Asp Thr Val Glu Asn Leu Ile Ile Leu Ala Asn Asn Ser Leu Ser Ser
            100                 105                 110

Asn Gly Asn Val Thr Glu Ser Gly Cys Lys Glu Cys Glu Glu Leu Glu
        115                 120                 125

Glu Lys Asn Ile Lys Glu Phe Leu Gln Ser Phe Val His Ile Val Gln
130                 135                 140

Met Phe Ile Asn Thr Ser
145                 150

<210> SEQ ID NO 11
<211> LENGTH: 447
<212> TYPE: DNA
<213> ORGANISM: Artificial Sequence
<220> FEATURE:
<223> OTHER INFORMATION: Description of Artificial Sequence:synthetic
      tPA5 + human improved IL-15(opt1)

<400> SEQUENCE: 11
atggatgcaa tgaagagagg gctctgctgt gtgctgctgc tgtgtggagc agtcttcgtt        60
tcgcccagcc aggaaatcca tgcccgattc agaagaggag cgaactgggt gaacgtgatc       120
tcggacctga agaagatcga ggacctcatc cagtcgatgc acatcgacgc gacgctgtac       180
acggagtcgg acgtccaccc gtcgtgcaag gtcacggcga tgaagtgctt cctcctggag       240
ctccaagtca tctcgctcga gtcggggggac gcgtcgatcc acgacacggt ggagaacctg      300
atcatcctgg cgaacaactc gctgtcgtcg aacgggaacg tcacggagtc gggctgcaag       360
gagtgcgagg agctggagga agaaaacatc aaggagttcc tgcagtcgtt cgtgcacatc       420
gtccagatgt tcatcaacac gtcgtga                                            447

<210> SEQ ID NO 12
<211> LENGTH: 148
<212> TYPE: PRT
<213> ORGANISM: Artificial Sequence
<220> FEATURE:
<223> OTHER INFORMATION: Description of Artificial Sequence:tPA5 + human
      improved IL-15(opt1)

<400> SEQUENCE: 12

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Asn Trp Val Asn Val Ile Ser Asp Leu Lys Lys Ile Glu Asp
        35                  40                  45

Leu Ile Gln Ser Met His Ile Asp Ala Thr Leu Tyr Thr Glu Ser Asp
    50                  55                  60

Val His Pro Ser Cys Lys Val Thr Ala Met Lys Cys Phe Leu Leu Glu
65                  70                  75                  80

Leu Gln Val Ile Ser Leu Glu Ser Gly Asp Ala Ser Ile His Asp Thr
                85                  90                  95

Val Glu Asn Leu Ile Ile Leu Ala Asn Asn Ser Leu Ser Ser Asn Gly
            100                 105                 110

Asn Val Thr Glu Ser Gly Cys Lys Glu Cys Glu Glu Leu Glu Glu Lys
        115                 120                 125

Asn Ile Lys Glu Phe Leu Gln Ser Phe Val His Ile Val Gln Met Phe
    130                 135                 140

Ile Asn Thr Ser

<210> SEQ ID NO 13
<211> LENGTH: 4533
<212> TYPE: DNA
<213> ORGANISM: Artificial Sequence
<220> FEATURE:
<223> OTHER INFORMATION: Description of Artificial Sequence:synthetic plasmid expression vector CMV human improved IL-15(opt1) (CMVhuIL-15(opt1)
<220> FEATURE:
<221> NAME/KEY: CDS
<222> LOCATION: (769)..(1257)
<223> OTHER INFORMATION: human interleukin-15 (IL-15)

<400> SEQUENCE: 13

```
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg ggaggtctat ataagcagag   660
ctcgtttagt gaaccgtcag atcgcctgga cgccatcc acgctgtttt gacctccata   720
gaagacaccg gaccgatcc agcctccgcg ggcgcgcgtc gacaagaaat gcggatctcg   780
aagccgcacc tgcggtcgat atcgatccag tgctacctgt gcctgctcct gaactcgcac   840
ttcctcacgg aggccggtat acacgtcttc atcctgggct gcttctcggc ggggctgccg   900
aagacggagc gaactggggt gaacgtgatc tcggacctga gaagatcga ggacctcatc   960
cagtcgatgc acatcgacgc gacgctgtac acggagtcgg acgtccaccc gtcgtgcaag  1020
gtcacggcga tgaagtgctt cctcctggag ctccaagtca tctcgctcga gtcggggac  1080
gcgtcgatcc acgacacggt ggagaacctg atcatcctgg cgaacaactc gctgtcgtcg  1140
aacgggaacg tcacggagtc gggctgcaag gagtgcgagg agctggagga gaagaacatc  1200
aaggagttcc tgcagtcgtt cgtgcacatc gtccagatgt tcatcaacac gtcgtgaggg  1260
cccggcgcgc cgaattcgcg gatatcggtt aacggatcca gatctgctgt gccttctagt  1320
tgccagccat ctgttgtttg cccctccccc gtgccttcct tgaccctgga aggtgccact  1380
cccactgtcc tttcctaata aaatgaggaa attgcatcgc attgtctgag taggtgtcat  1440
tctattctgg ggggtgggt gggcagcac agcaaggggg aggattggga agacaatagc  1500
aggcatgctg gggatgcggt gggctctatg ggtacccagg tgctgaagaa ttgacccggt  1560
tcctcctggg ccagaaagaa gcaggcacat ccccttctct gtgacacacc ctgtccacgc  1620
ccctggttct tagttccagc cccactcata ggacactcat agctcaggag gctccgcct  1680
tcaatcccac ccgctaaagt acttggagcg gtctctccct ccctcatcag cccaccaaac  1740
caaacctagc ctccaagagt gggaagaaat taaagcaaga taggctatta agtgcagagg  1800
gagagaaaat gcctccaaca tgtgaggaag taatgagaga aatcatagaa tttcttccgc  1860
```

```
ttcctcgctc actgactcgc tgcgctcggt cgttcggctg cggcgagcgg tatcagctca    1920
ctcaaaggcg gtaatacggt tatccacaga atcaggggat aacgcaggaa agaacatgtg    1980
agcaaaaggc cagcaaaagg ccaggaaccg taaaaaggcc gcgttgctgg cgttttttcca   2040 taggctccgc ccccctgacg agcatcacaa aaatcgacgc tcaagtcaga ggtggcgaaa    2100
cccgacagga ctataaagat accaggcgtt tccccctgga agctccctcg tgcgctctcc    2160
tgttccgacc ctgccgctta ccggatacct gtccgccttt ctcccttcgg gaagcgtggc    2220
gctttctcaa tgctcacgct gtaggtatct cagttcggtg taggtcgttc gctccaagct    2280
gggctgtgtg cacgaacccc ccgttcagcc cgaccgctgc gccttatccg gtaactatcg    2340
tcttgagtcc aacccggtaa gacacgactt atcgccactg gcagcagcca ctggtaacag    2400
gattagcaga gcgaggtatg taggcggtgc tacagagttc ttgaagtggt ggcctaacta    2460
cggctacact agaaggacag tatttggtat ctgcgctctg ctgaagccag ttaccttcgg    2520
aaaaagagtt ggtagctctt gatccggcaa acaaaccacc gctggtagcg gtggtttttt    2580
tgtttgcaag cagcagatta cgcgcagaaa aaaaggatct caagaagatc ctttgatctt    2640
ttctacgggg tctgacgctc agtggaacga aaactcacgt taagggattt tggtcatgag    2700
attatcaaaa aggatcttca cctagatcct tttaaattaa aaatgaagtt ttaaatcaat    2760
ctaaagtata tatgagtaaa cttggtctga cagttaccaa tgcttaatca gtgaggcacc    2820
tatctcagcg atctgtctat ttcgttcatc catagttgcc tgactccggg ggggggggc    2880 gctgaggtct gcctcgtgaa gaaggtgttg ctgactcata ccaggcctga atcgccccat    2940
catccagcca gaaagtgagg gagccacggt tgatgagagc tttgttgtag gtggaccagt    3000
tggtgatttt gaacttttgc tttgccacgg aacggtctgc gttgtcggga agatgcgtga    3060
tctgatcctt caactcagca aaagttcgat ttattcaaca aagccgccgt cccgtcaagt    3120
cagcgtaatg ctctgccagt gttacaacca attaaccaat tctgattaga aaaactcatc    3180
gagcatcaaa tgaaactgca atttattcat atcaggatta tcaataccat attttgaaa     3240 aagccgtttc tgtaatgaag gagaaaactc accgaggcag ttccatagga tggcaagatc    3300
ctggtatcgg tctgcgattc cgactcgtcc aacatcaata caacctatta atttcccctc    3360
gtcaaaaata aggttatcaa gtgagaaatc accatgagtg acgactgaat ccggtgagaa    3420
tggcaaaagc ttatgcattt ctttccagac ttgttcaaca ggccagccat tacgctcgtc    3480
atcaaaatca ctcgcatcaa ccaaaccgtt attcattcgt gattgcgcct gagcgagacg    3540
aaatacgcga tcgctgttaa aaggacaatt acaaacagga tcgaatgca accggcgcag     3600 gaacactgcc agcgcatcaa caatattttc acctgaatca ggatattctt ctaatacctg    3660
gaatgctgtt ttcccgggga tcgcagtggt gagtaaccat gcatcatcag gagtacggat    3720
aaaatgcttg atggtcggaa gaggcataaa ttccgtcagc cagtttagtc tgaccatctc    3780
atctgtaaca tcattggcaa cgctacctt gccatgtttc agaaacaact ctggcgcatc      3840
gggcttccca tacaatcgat agattgtcgc acctgattgc ccgacattat cgcgagccca    3900 tttatacccca tataaatcag catccatgtt ggaatttaat cgcggcctcg agcaagacgt    3960
ttcccgttga atatggctca taacacccct tgtattactg tttatgtaag cagacagttt    4020
tattgttcat gatgatatat ttttatcttg tgcaatgtaa catcagagat tttgagacac    4080
aacgtggctt tcccccccccc cccattattg aagcatttat cagggttatt gtctcatgag    4140
cggatacata tttgaatgta tttagaaaaa taaacaaata ggggttccgc gcacatttcc    4200
```

```
ccgaaaagtg ccacctgacg tctaagaaac cattattatc atgacattaa cctataaaaa    4260
taggcgtatc acgaggccct ttcgtctcgc gcgtttcggt gatgacggtg aaaacctctg    4320
acacatgcag ctcccggaga cggtcacagc ttgtctgtaa gcggatgccg ggagcagaca    4380
agcccgtcag ggcgcgtcag cgggtgttgg cgggtgtcgg ggctggctta actatgcggc    4440
atcagagcag attgtactga gagtgcacca tatgcggtgt gaaataccgc acagatgcgt    4500
aaggagaaaa taccgcatca gattggctat tgg                                 4533

<210> SEQ ID NO 14
<211> LENGTH: 489
<212> TYPE: DNA
<213> ORGANISM: Macaca mulatta
<220> FEATURE:
<223> OTHER INFORMATION: rhesus macaque wild-type interleukin-15 (IL-15)
      nucleic acid sequence

<400> SEQUENCE: 14
atgagaattt cgaaaccaca tttgagaagt gtttccatcc agtgctactt gtgtttactt      60
ctaaacagtc attttctaac tgaagctggc attcatgtct catttttggg ctgtttcagt     120
gcagggctcc ctaaaacaga agccaactgg gtgaatgtaa taagtgattt gaaaaaaatt     180
gaagatctta ttcaatctat gcatattgat gctactttat atacagaaag tgatgttcac     240
cccagttgca aggtaacagc aatgaagtgc tttctcttgg agttgcaagt tatttcacat     300
gagtccggag atacagatat tcatgataca gtagaaaatc ttatcatcct agcaaacaac     360
atcttgtctt ctaatgggaa tataacagaa tctggatgca agaatgtgaa ggaactagag     420
gaaaaaaata ttaaagaatt tttgcagagt tttgtacata ttgtccaaat gttcatcaac     480
acttcttga                                                              489

<210> SEQ ID NO 15
<211> LENGTH: 162
<212> TYPE: PRT
<213> ORGANISM: Macaca mulatta
<220> FEATURE:
<223> OTHER INFORMATION: rhesus macaque wild-type interleukin-15 (IL-15)

<400> SEQUENCE: 15

Met Arg Ile Ser Lys Pro His Leu Arg Ser Val Ser Ile Gln Cys Tyr
  1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser His Glu Ser Gly Asp Thr Asp Ile His Asp Thr Val Glu
            100                 105                 110

Asn Leu Ile Ile Leu Ala Asn Asn Ile Leu Ser Ser Asn Gly Asn Ile
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
```

Thr Ser
        145                 150                 155                 160

<210> SEQ ID NO 16
<211> LENGTH: 489
<212> TYPE: DNA
<213> ORGANISM: Artificial Sequence
<220> FEATURE:
<223> OTHER INFORMATION: Description of Artificial Sequence:synthetic
      rhesus improved IL-15 (opt)

<400> SEQUENCE: 16

```
atgcggatct cgaagccgca cctgcggtcg gtctcgatcc agtgctacct gtgcctgctc    60
ctgaactcgc acttcctcac ggaggccggt atacacgtct tcatcctggg ctgcttctcg   120
gcggggctgc cgaagacgga ggcgaactgg gtgaacgtga tctcggacct gaagaagatc   180
gaggacctca tccagtcgat gcacatcgac gcgacgctgt acacggagtc ggacgtccac   240
ccgtcgtgca aggtcacggc gatgaagtgc ttcctcctgg agctccaagt catctcgcac   300
gagtcggggg acacggacat ccacgacacg gtggagaacc tgatcatcct ggcgaacaac   360
atcctgtcgt cgaacgggaa catcacggag tcgggctgca aggagtgcga ggagctggag   420
gagaagaaca tcaaggagtt cctgcagtcg ttcgtgcaca tcgtccagat gttcatcaac   480
acgtcgtga                                                            489
```

<210> SEQ ID NO 17
<211> LENGTH: 453
<212> TYPE: DNA
<213> ORGANISM: Artificial Sequence
<220> FEATURE:
<223> OTHER INFORMATION: Description of Artificial Sequence:synthetic
      tPA2 + rhesus improved IL-15

<400> SEQUENCE: 17

```
atggatgcaa tgaagagagg gctctgctgt gtgctgctgc tgtgtggagc agtcttcgtt    60
tcgcccagcc aggaaatcca tgcccgattc agaagaggag ccagagcgaa ctgggtgaac   120
gtgatctcgg acctgaagaa gatcgaggac ctcatccagt cgatgcacat cgacgcgacg   180
ctgtacacgg agtcggacgt ccacccgtcg tgcaaggtca cggcgatgaa gtgcttcctc   240
ctggagctcc aagtcatctc gcacgagtcg ggggacacgg acatccacga cacggtggag   300
aacctgatca tcctggcgaa caacatcctg tcgtcgaacg ggaacatcac ggagtcgggc   360
tgcaaggagt gcgaggagct ggaggagaag aacatcaagg agttcctgca gtcgttcgtg   420
cacatcgtcc agatgttcat caacacgtcg tga                                 453
```

<210> SEQ ID NO 18
<211> LENGTH: 150
<212> TYPE: PRT
<213> ORGANISM: Artificial Sequence
<220> FEATURE:
<223> OTHER INFORMATION: Description of Artificial Sequence:synthetic
      tPA2 + rhesus improved IL-15

<400> SEQUENCE: 18

Met Asp Ala Met Lys Arg Gly Leu Cys Cys Val Leu Leu Leu Cys Gly
  1               5                  10                  15

Ala Val Phe Val Ser Pro Ser Gln Glu Ile His Ala Arg Phe Arg Arg
                20                  25                  30

Gly Ala Arg Ala Asn Trp Val Asn Val Ile Ser Asp Leu Lys Lys Ile
            35                  40                  45

```
Glu Asp Leu Ile Gln Ser Met His Ile Asp Ala Thr Leu Tyr Thr Glu
        50                  55                  60

Ser Asp Val His Pro Ser Cys Lys Val Thr Ala Met Lys Cys Phe Leu
 65                  70                  75                  80

Leu Glu Leu Gln Val Ile Ser His Glu Ser Gly Asp Thr Asp Ile His
                 85                  90                  95

Asp Thr Val Glu Asn Leu Ile Ile Leu Ala Asn Asn Ile Leu Ser Ser
            100                 105                 110

Asn Gly Asn Ile Thr Glu Ser Gly Cys Lys Glu Cys Glu Glu Leu Glu
        115                 120                 125

Glu Lys Asn Ile Lys Glu Phe Leu Gln Ser Phe Val His Ile Val Gln
        130                 135                 140

Met Phe Ile Asn Thr Ser
145                 150

<210> SEQ ID NO 19
<211> LENGTH: 447
<212> TYPE: DNA
<213> ORGANISM: Artificial Sequence
<220> FEATURE:
<223> OTHER INFORMATION: Description of Artificial Sequence:synthetic
      tPA5 + rhesus improved IL-15

<400> SEQUENCE: 19
atggatgcaa tgaagagagg gctctgctgt gtgctgctgc tgtgtggagc agtcttcgtt      60
tcgcccagcc aggaaatcca tgcccgattc agaagaggag cgaactgggt gaacgtgatc    120
tcggacctga agaagatcga ggacctcatc cagtcgatgc acatcgacgc gacgctgtac    180
acggagtcgg acgtccaccc gtcgtgcaag gtcacggcga tgaagtgctt cctcctggag    240
ctccaagtca tctcgcacga gtcggggac acggacatcc acgacacggt ggagaacctg    300
atcatcctgg cgaacaacat cctgtcgtcg aacgggaaca tcacggagtc gggctgcaag    360
gagtgcgagg agctggagga agagaacatc aaggagttcc tgcagtcgtt cgtgcacatc    420
gtccagatgt tcatcaacac gtcgtga                                        447

<210> SEQ ID NO 20
<211> LENGTH: 148
<212> TYPE: PRT
<213> ORGANISM: Artificial Sequence
<220> FEATURE:
<223> OTHER INFORMATION: Description of Artificial Sequence:tPA5 +
      rhesus improved IL-15

<400> SEQUENCE: 20

Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
                20                  25                  30

Gly Ala Asn Trp Val Asn Val Ile Ser Asp Leu Lys Lys Ile Glu Asp
            35                  40                  45

Leu Ile Gln Ser Met His Ile Asp Ala Thr Leu Tyr Thr Glu Ser Asp
 50                  55                  60

Val His Pro Ser Cys Lys Val Thr Ala Met Lys Cys Phe Leu Leu Glu
 65                  70                  75                  80

Leu Gln Val Ile Ser His Glu Ser Gly Asp Thr Asp Ile His Asp Thr
                85                  90                  95

Val Glu Asn Leu Ile Ile Leu Ala Asn Asn Ile Leu Ser Ser Asn Gly
```

```
                    100              105              110
Asn Ile Thr Glu Ser Gly Cys Lys Glu Cys Glu Glu Leu Glu Glu Lys
            115              120              125
Asn Ile Lys Glu Phe Leu Gln Ser Phe Val His Ile Val Gln Met Phe
        130              135              140
Ile Asn Thr Ser
145

<210> SEQ ID NO 21
<211> LENGTH: 4521
<212> TYPE: DNA
<213> ORGANISM: Artificial Sequence
<220> FEATURE:
<223> OTHER INFORMATION: Description of Artificial Sequence:synthetic
      plasmid expression vector CMV rhesus improved IL-15
      (CMVrhIL-15opt)
<220> FEATURE:
<221> NAME/KEY: CDS
<222> LOCATION: (769)..(1257)
<223> OTHER INFORMATION: rhesus interleukin-15 (IL-15)

<400> SEQUENCE: 21
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
acggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg ggaggtctat ataagcagag     660
ctcgtttagt gaaccgtcag atcgcctgga cgccatcc acgctgtttt gacctccata     720
gaagacaccg ggaccgatcc agcctccgcg gcgcgcgtc gacaagaaat gcggatctcg     780
aagccgcacc tgcggtcggt ctcgatccag tgctacctgt gcctgctcct gaactcgcac     840
ttcctcacgg aggccggtat acacgtcttc atcctgggct gcttctcggc ggggctgccg     900
aagacggagc gaactgggt gaacgtgatc tcggacctga agaagatcga ggacctcatc     960
cagtcgatgc acatcgacgc gacgctgtac acggagtcgg acgtccaccc gtcgtgcaag    1020
gtcacggcga tgaagtgctt cctcctggag ctccaagtca tctcgcacga gtcggggac    1080
acggacatcc acgacacggt ggagaacctg atcatcctgg cgaacaacat cctgtcgtcg    1140
aacgggaaca tcacggagtc gggctgcaag gagtgcgagg agctggagga gaagaacatc    1200
aaggagttcc tgcagtcgtt cgtgcacatc gtccagatgt tcatcaacac gtcgtgaggg    1260
cccatgcggc gcgtaggaa ttcgatccag atctgctgtg ccttctagtt gccagccatc    1320
tgttgtttgc ccctccccg tgccttcctt gaccctggaa ggtgccactc ccactgtcct    1380
ttcctaataa aatgaggaaa ttgcatcgca ttgtctgagt aggtgtcatt ctattctggg    1440
gggtggggtg gggcaggaca gcaagggga ggattggaa gacaaatagca ggcatgctgg    1500
ggatgcggtg ggctctatgg gtacccaggt gctgaagaat tgacccggtt cctcctgggc    1560
```

```
cagaaagaag caggcacatc cccttctctg tgacacaccc tgtccacgcc cctggttctt    1620
agttccagcc ccactcatag gacactcata gctcaggagg gctccgcctt caatcccacc    1680
cgctaaagta cttggagcgg tctctccctc cctcatcagc ccaccaaacc aaacctagcc    1740
tccaagagtg ggaagaaatt aaagcaagat aggctattaa gtgcagaggg agagaaaatg    1800
cctccaacat gtgaggaagt aatgagagaa atcatagaat ttcttccgct tcctcgctca    1860
ctgactcgct gcgctcggtc gttcggctgc ggcgagcggt atcagctcac tcaaaggcgg    1920
taatacggtt atccacagaa tcaggggata acgcaggaaa gaacatgtga gcaaaaggcc    1980
agcaaaaggc caggaaccgt aaaaaggccg cgttgctggc gttttccat aggctccgcc     2040 cccctgacga gcatcacaaa aatcgacgct caagtcagag gtggcgaaac ccgacaggac    2100
tataaagata ccaggcgttt ccccctggaa gctccctcgt gcgctctcct gttccgaccc    2160
tgccgcttac cggatacctg tccgcctttc tcccttcggg aagcgtggcg ctttctcaat    2220
gctcacgctg taggtatctc agttcggtgt aggtcgttcg ctccaagctg ggctgtgtgc    2280
acgaaccccc cgttcagccc gaccgctgcg ccttatccgg taactatcgt cttgagtcca    2340
acccggtaag acacgactta tcgccactgg cagcagccac tggtaacagg attagcagag    2400
cgaggtatgt aggcggtgct acagagttct tgaagtggtg gcctaactac ggctacacta    2460
gaaggacagt atttggtatc tgcgctctgc tgaagccagt taccttcgga aaaagagttg    2520
gtagctcttg atccggcaaa caaaccaccg ctggtagcgg tggtttttt gtttgcaagc     2580 agcagattac gcgcagaaaa aaaggatctc aagaagatcc tttgatcttt tctacggggt    2640
ctgacgctca gtggaacgaa aactcacgtt aagggatttt ggtcatgaga ttatcaaaaa    2700
ggatcttcac ctagatcctt ttaaattaaa aatgaagttt taaatcaatc taaagtatat    2760
atgagtaaac ttggtctgac agttaccaat gcttaatcag tgaggcacct atctcagcga    2820
tctgtctatt tcgttcatcc atagttgcct gactcggggg ggggggcgc tgaggtctgc      2880 ctcgtgaaga aggtgttgct gactcatacc aggcctgaat cgccccatca tccagccaga    2940
aagtgaggga gccacggttg atgagagctt tgttgtaggt ggaccagttg gtgattttga    3000
acttttgctt tgccacggaa cggtctgcgt tgtcggaag atgcgtgatc tgatccttca     3060
actcagcaaa agttcgattt attcaacaaa gccgccgtcc cgtcaagtca gcgtaatgct    3120
ctgccagtgt tacaaccaat taaccaattc tgattagaaa aactcatcga gcatcaaatg    3180
aaactgcaat ttattcatat caggattatc aataccatat ttttgaaaaa gccgtttctg    3240
taatgaagga gaaaactcac cgaggcagtt ccataggatg caagatcct ggtatcggtc     3300 tgcgattccg actcgtccaa catcaataca acctattaat ttcccctcgt caaaaataag    3360
gttatcaagt gagaaatcac catgagtgac gactgaatcc ggtgagaatg gcaaaagctt    3420
atgcatttct ttccagactt gttcaacagg ccagccatta cgctcgtcat caaaatcact    3480
cgcatcaacc aaaccgttat tcattcgtga ttgcgcctga gcgagacgaa atacgcgatc    3540
gctgttaaaa ggacaattac aaacaggaat cgaatgcaac cggcgcagga acactgccag    3600
cgcatcaaca atattttcac ctgaatcagg atattcttct aatacctgga atgctgtttt    3660 cccgggatc gcagtggtga gtaaccatgc atcatcagga gtacggataa aatgcttgat     3720
ggtcggaaga ggcataaatt ccgtcagcca gtttagtctg accatctcat ctgtaacatc    3780
attggcaacg ctacctttgc catgtttcag aaacaactct ggcgcatcgg gcttcccata    3840
caatcgatag attgtcgcac ctgattgccc gacattatcg cgagcccatt tatacccata    3900
taaatcagca tccatgttgg aatttaatcg cggcctcgag caagacgttt cccgttgaat    3960
```

```
atggctcata acaccccttg tattactgtt tatgtaagca gacagtttta ttgttcatga    4020
tgatatattt ttatcttgtg caatgtaaca tcagagattt tgagacacaa cgtggctttc    4080 ccccccccc cattattgaa gcatttatca gggttattgt ctcatgagcg gatacatatt     4140
tgaatgtatt tagaaaaata aacaaatagg ggttccgcgc acatttcccc gaaaagtgcc    4200
acctgacgtc taagaaacca ttattatcat gacattaacc tataaaaata ggcgtatcac    4260
gaggcccttt cgtctcgcgc gtttcggtga tgacggtgaa aacctctgac acatgcagct    4320
cccggagacg gtcacagctt gtctgtaagc ggatgccggg agcagacaag cccgtcaggg    4380
cgcgtcagcg ggtgttggcg ggtgtcgggg ctggcttaac tatgcggcat cagagcagat    4440
tgtactgaga gtgcaccata tgcggtgtga ataccgcac agatgcgtaa ggagaaaata    4500
ccgcatcaga ttggctattg g                                             4521

<210> SEQ ID NO 22
<211> LENGTH: 226
<212> TYPE: DNA
<213> ORGANISM: Artificial Sequence
<220> FEATURE:
<223> OTHER INFORMATION: Description of Artificial Sequence:synthetic
      RNA transport element (RTE) RTEm26

<400> SEQUENCE: 22
ccgtggggtg cgaggctaag cactgcacag aggatagctt gctgttggca tcctgtggaa     60
ggcacgtctg attgcatgaa ggttcagtgt cctagttccc ttcccccagg aaaaacgaca    120
cgggagctgg ccaagacctc tctgggtgat gagcctaagg gatggttttg tgtagggccc    180
ctatgcttgg cggctgggga tcagacctct accttcaccc atgagg                   226

<210> SEQ ID NO 23
<211> LENGTH: 427
<212> TYPE: DNA
<213> ORGANISM: Artificial Sequence
<220> FEATURE:
<223> OTHER INFORMATION: Description of Artificial Sequence:synthetic
      RNA transport element (RTE)-constitutive transport element (CTE)
      combination element RTEm26CTE

<400> SEQUENCE: 23
ccgtggggtg cgaggctaag cactgcacag aggatagctt gctgttggca tcctgtggaa     60
ggcacgtctg attgcatgaa ggttcagtgt cctagttccc ttcccccagg aaaaacgaca    120
cgggagctgg ccaagacctc tctgggtgat gagcctaagg gatggttttg tgtagggccc    180
ctatgcttgg cggctgggga tcagacctct accttcaccc atgaggtatc gataccgcgg    240
ggatcctcta gagtagacca cctcccctgc gagctaagct ggacagccaa tgacgggtaa    300
gagagtgaca ttttttcacta acctaagaca ggagggccgt cagagctact gcctaatcca    360
aagacgggta aaagtgataa aaatgtatca ctccaaccta agacaggcgc agcttccgag    420
ggatttg                                                             427

<210> SEQ ID NO 24
<211> LENGTH: 105
<212> TYPE: DNA
<213> ORGANISM: Artificial Sequence
<220> FEATURE:
<223> OTHER INFORMATION: Description of Artificial Sequence:tissue
      plasminogen activator (tPA) signal and propeptide
      tPA6
<220> FEATURE:
<221> NAME/KEY: sig_peptide
```

```
<222> LOCATION: (1)..(69)
<223> OTHER INFORMATION: tPA signal
<220> FEATURE:
<221> NAME/KEY: misc_feature
<222> LOCATION: (70)..(105)
<223> OTHER INFORMATION: tPA6 propeptide

<400> SEQUENCE: 24
atggatgcaa tgaagagagg gctctgctgt gtgctgctgc tgtgtggagc agtcttcgtt      60
tcgcccagcc aggaaatcca tgcccgattc agaagaggag ccaga                    105

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence:synthetic
      tissue plasminogen activator (tPA) signal and propeptide tPA6
<220> FEATURE:
<221> NAME/KEY: SIGNAL
<222> LOCATION: (1)..(23)
<223> OTHER INFORMATION: tPA signal peptide
<220> FEATURE:
<221> NAME/KEY: PROPEP
<222> LOCATION: (24)..(35)
<223> OTHER INFORMATION: tPA6 propeptide

<400> SEQUENCE: 25

Met Asp Ala Met Lys Arg Gly Leu Cys Cys Val Leu Leu Leu Cys Gly
  1               5                  10                  15

Ala Val Phe Val Ser Pro Ser Gln Glu Ile His Ala Arg Phe Arg Arg
             20                  25                  30

Gly Ala Arg
         35

<210> SEQ ID NO 26
<211> LENGTH: 99
<212> TYPE: DNA
<213> ORGANISM: Artificial Sequence
<220> FEATURE:
<223> OTHER INFORMATION: Description of Artificial Sequence:synthetic
      tissue plasminogen activator (tPA) signal and propeptide
      tPA7
<220> FEATURE:
<221> NAME/KEY: sig_peptide
<222> LOCATION: (1)..(69)
<223> OTHER INFORMATION: tPA signal
<220> FEATURE:
<221> NAME/KEY: misc_feature
<222> LOCATION: (70)..(99)
<223> OTHER INFORMATION: tPA7 propeptide

<400> SEQUENCE: 26
atggatgcaa tgaagagagg gctctgctgt gtgctgctgc tgtgtggagc agtcttcgtt      60
tcgcccagcc aggaaatcca tgcccgattc agaagagga                            99

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence:synthetic
      tissue plasminogen activator (tPA) signal and propeptide
      tPA7
<220> FEATURE:
<221> NAME/KEY: SIGNAL
<222> LOCATION: (1)..(23)
<223> OTHER INFORMATION: tPA signal peptide
<220> FEATURE:
```

```
<221> NAME/KEY: PROPEP
<222> LOCATION: (24)..(33)
<223> OTHER INFORMATION: tPA7 propeptide

<400> SEQUENCE: 27
```

Met Asp Ala Met Lys Arg Gly Leu Cys Cys Val Leu Leu Cys Gly
 1               5                  10                  15

Ala Val Phe Val Ser Pro Ser Gln Glu Ile His Ala Arg Phe Arg Arg
            20                  25                  30

Gly

```
<210> SEQ ID NO 28
<211> LENGTH: 450
<212> TYPE: DNA
<213> ORGANISM: Artificial Sequence
<220> FEATURE:
<223> OTHER INFORMATION: Description of Artificial Sequence:synthetic
      tPA6 + human improved IL-15(opt1)

<400> SEQUENCE: 28
```
atggatgcaa tgaagagagg gctctgctgt gtgctgctgc tgtgtggagc agtcttcgtt      60
tcgcccagcc aggaaatcca tgcccgattc agaagaggag ccagaaactg ggtgaacgtg     120
atctcggacc tgaagaagat cgaggacctc atccagtcga tgcacatcga cgcgacgctg     180
tacacggagt cggacgtcca cccgtcgtgc aaggtcacgg cgatgaagtg cttcctcctg     240
gagctccaag tcatctcgct cgagtcgggg gacgcgtcga tccacgacac ggtggagaac     300
ctgatcatcc tggcgaacaa ctcgctgtcg tcgaacggga acgtcacgga gtcgggctgc     360
aaggagtgcg aggagctgga ggagaagaac atcaaggagt tcctgcagtc gttcgtgcac     420
atcgtccaga tgttcatcaa cacgtcgtga                                     450

```
<210> SEQ ID NO 29
<211> LENGTH: 149
<212> TYPE: PRT
<213> ORGANISM: Artificial Sequence
<220> FEATURE:
<223> OTHER INFORMATION: Description of Artificial Sequence:synthetic
      tPA6 + human improved IL-15(opt1)

<400> SEQUENCE: 29
```

Met Asp Ala Met Lys Arg Gly Leu Cys Cys Val Leu Leu Cys Gly
 1               5                  10                  15

Ala Val Phe Val Ser Pro Ser Gln Glu Ile His Ala Arg Phe Arg Arg
            20                  25                  30

Gly Ala Arg Asn Trp Val Asn Val Ile Ser Asp Leu Lys Lys Ile Glu
                35                  40                  45

Asp Leu Ile Gln Ser Met His Ile Asp Ala Thr Leu Tyr Thr Glu Ser
     50                  55                  60

Asp Val His Pro Ser Cys Lys Val Thr Ala Met Lys Cys Phe Leu Leu
 65                  70                  75                  80

Glu Leu Gln Val Ile Ser Leu Glu Ser Gly Asp Ala Ser Ile His Asp
                85                  90                  95

Thr Val Glu Asn Leu Ile Ile Leu Ala Asn Asn Ser Leu Ser Ser Asn
            100                 105                 110

Gly Asn Val Thr Glu Ser Gly Cys Lys Glu Cys Glu Glu Leu Glu Glu
        115                 120                 125

Lys Asn Ile Lys Glu Phe Leu Gln Ser Phe Val His Ile Val Gln Met
    130                 135                 140

Phe Ile Asn Thr Ser
145

<210> SEQ ID NO 30
<211> LENGTH: 444
<212> TYPE: DNA
<213> ORGANISM: Artificial Sequence
<220> FEATURE:
<223> OTHER INFORMATION: Description of Artificial Sequence:synthetic
      tPA7 + human improved IL-15(opt1)

<400> SEQUENCE: 30

```
atggatgcaa tgaagagagg gctctgctgt gtgctgctgc tgtgtggagc agtcttcgtt        60
tcgcccagcc aggaaatcca tgcccgattc agaagaggaa actgggtgaa cgtgatctcg       120
gacctgaaga gatcgagga cctcatccag tcgatgcaca tcgacgcgac gctgtacacg        180
gagtcggacg tccacccgtc gtgcaaggtc acggcgatga agtgcttcct cctggagctc      240
caagtcatct cgctcgagtc gggggacgcg tcgatccacg acacggtgga gaacctgatc      300
atcctggcga caactcgct gtcgtcgaac gggaacgtca cggagtcggg ctgcaaggag        360
tgcgaggagc tggaggagaa gaacatcaag gagttcctgc agtcgttcgt gcacatcgtc      420
cagatgttca tcaacacgtc gtga                                              444
```

<210> SEQ ID NO 31
<211> LENGTH: 147
<212> TYPE: PRT
<213> ORGANISM: Artificial Sequence
<220> FEATURE:
<223> OTHER INFORMATION: Description of Artificial Sequence:synthetic
      tPA7 + human improved IL-15(opt1)

<400> SEQUENCE: 31

Met Asp Ala Met Lys Arg Gly Leu Cys Cys Val Leu Leu Leu Cys Gly
1               5                  10                  15

Ala Val Phe Val Ser Pro Ser Gln Glu Ile His Ala Arg Phe Arg Arg
            20                  25                  30

Gly Asn Trp Val Asn Val Ile Ser Asp Leu Lys Lys Ile Glu Asp Leu
        35                  40                  45

Ile Gln Ser Met His Ile Asp Ala Thr Leu Tyr Thr Glu Ser Asp Val
    50                  55                  60

His Pro Ser Cys Lys Val Thr Ala Met Lys Cys Phe Leu Leu Glu Leu
65                  70                  75                  80

Gln Val Ile Ser Leu Glu Ser Gly Asp Ala Ser Ile His Asp Thr Val
                85                  90                  95

Glu Asn Leu Ile Ile Leu Ala Asn Asn Ser Leu Ser Ser Asn Gly Asn
            100                 105                 110

Val Thr Glu Ser Gly Cys Lys Glu Cys Glu Glu Leu Glu Glu Lys Asn
        115                 120                 125

Ile Lys Glu Phe Leu Gln Ser Phe Val His Ile Val Gln Met Phe Ile
    130                 135                 140

Asn Thr Ser
145

<210> SEQ ID NO 32
<211> LENGTH: 450
<212> TYPE: DNA
<213> ORGANISM: Artificial Sequence
<220> FEATURE:
<223> OTHER INFORMATION: Description of Artificial Sequence:synthetic
      tPA6 + rhesus improved IL-15

<400> SEQUENCE: 32

```
atggatgcaa tgaagagagg gctctgctgt gtgctgctgc tgtgtggagc agtcttcgtt    60
tcgcccagcc aggaaatcca tgcccgattc agaagaggag ccagaaactg ggtgaacgtg   120
atctcggacc tgaagaagat cgaggacctc atccagtcga tgcacatcga cgcgacgctg   180
tacacggagt cggacgtcca cccgtcgtgc aaggtcacgg cgatgaagtg cttcctcctg   240
gagctccaag tcatctcgca cgagtcgggg gacacggaca tccacgacac ggtggagaac   300
ctgatcatcc tggcgaacaa catcctgtcg tcgaacggga acatcacgga gtcgggctgc   360
aaggagtgcg aggagctgga ggagaagaac atcaaggagt tcctgcagtc gttcgtgcac   420
atcgtccaga tgttcatcaa cacgtcgtga                                    450
```

<210> SEQ ID NO 33
<211> LENGTH: 149
<212> TYPE: PRT
<213> ORGANISM: Artificial Sequence
<220> FEATURE:
<223> OTHER INFORMATION: Description of Artificial Sequence:tPA6 + rhesus improved IL-15

<400> SEQUENCE: 33

```
Met Asp Ala Met Lys Arg Gly Leu Cys Cys Val Leu Leu Cys Gly
  1               5                  10                  15

Ala Val Phe Val Ser Pro Ser Gln Glu Ile His Ala Arg Phe Arg Arg
             20                  25                  30

Gly Ala Arg Asn Trp Val Asn Val Ile Ser Asp Leu Lys Lys Ile Glu
         35                  40                  45

Asp Leu Ile Gln Ser Met His Ile Asp Ala Thr Leu Tyr Thr Glu Ser
     50                  55                  60

Asp Val His Pro Ser Cys Lys Val Thr Ala Met Lys Cys Phe Leu Leu
 65                  70                  75                  80

Glu Leu Gln Val Ile Ser His Glu Ser Gly Asp Thr Asp Ile His Asp
                 85                  90                  95

Thr Val Glu Asn Leu Ile Ile Leu Ala Asn Asn Ile Leu Ser Ser Asn
            100                 105                 110

Gly Asn Ile Thr Glu Ser Gly Cys Lys Glu Cys Glu Glu Leu Glu Glu
        115                 120                 125

Lys Asn Ile Lys Glu Phe Leu Gln Ser Phe Val His Ile Val Gln Met
    130                 135                 140

Phe Ile Asn Thr Ser
145
```

<210> SEQ ID NO 34
<211> LENGTH: 444
<212> TYPE: DNA
<213> ORGANISM: Artificial Sequence
<220> FEATURE:
<223> OTHER INFORMATION: Description of Artificial Sequence:synthetic tPA7 + rhesus improved IL-15

<400> SEQUENCE: 34

```
atggatgcaa tgaagagagg gctctgctgt gtgctgctgc tgtgtggagc agtcttcgtt    60
tcgcccagcc aggaaatcca tgcccgattc agaagaggaa actgggtgaa cgtgatctcg   120
gacctgaaga gatcgagga cctcatccag tcgatgcaca tcgacgcgac gctgtacacg   180
gagtcggacg tccacccgtc gtgcaaggtc acggcgatga agtgcttcct cctggagctc   240
```

```
caagtcatct cgcacgagtc gggggacacg gacatccacg acacggtgga gaacctgatc      300
atcctggcga acaacatcct gtcgtcgaac gggaacatca cggagtcggg ctgcaaggag      360
tgcgaggagc tggaggagaa gaacatcaag gagttcctgc agtcgttcgt gcacatcgtc      420
cagatgttca tcaacacgtc gtga                                              444
```

<210> SEQ ID NO 35
<211> LENGTH: 147
<212> TYPE: PRT
<213> ORGANISM: Artificial Sequence
<220> FEATURE:
<223> OTHER INFORMATION: Description of Artificial Sequence:synthetic
      tPA7 + rhesus improved IL-15

<400> SEQUENCE: 35

```
Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
            20                  25                  30

Gly Asn Trp Val Asn Val Ile Ser Asp Leu Lys Lys Ile Glu Asp Leu
        35                  40                  45

Ile Gln Ser Met His Ile Asp Ala Thr Leu Tyr Thr Glu Ser Asp Val
    50                  55                  60

His Pro Ser Cys Lys Val Thr Ala Met Lys Cys Phe Leu Leu Glu Leu
65                  70                  75                  80

Gln Val Ile Ser His Glu Ser Gly Asp Thr Asp Ile His Asp Thr Val
                85                  90                  95

Glu Asn Leu Ile Ile Leu Ala Asn Asn Ile Leu Ser Ser Asn Gly Asn
            100                 105                 110

Ile Thr Glu Ser Gly Cys Lys Glu Cys Glu Glu Leu Glu Glu Lys Asn
        115                 120                 125

Ile Lys Glu Phe Leu Gln Ser Phe Val His Ile Val Gln Met Phe Ile
    130                 135                 140

Asn Thr Ser
145
```

<210> SEQ ID NO 36
<211> LENGTH: 52
<212> TYPE: PRT
<213> ORGANISM: Artificial Sequence
<220> FEATURE:
<223> OTHER INFORMATION: Description of Artificial Sequence:synthetic
      IL15opt signal peptide-propeptide-huIL-15 junction

<400> SEQUENCE: 36

```
Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn
    50
```

<210> SEQ ID NO 37
<211> LENGTH: 40
<212> TYPE: PRT
<213> ORGANISM: Artificial Sequence
<220> FEATURE:
<223> OTHER INFORMATION: Description of Artificial Sequence:IL15opt-tPA2 signal peptide-propeptide-huIL-15 junction

<400> SEQUENCE: 37

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Asn Trp Val Asn
        35                  40

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:synthetic
      IL15opt-tPA2 N-terminal sequence after furin cleavage

<400> SEQUENCE: 38

Gly Ala Arg Ala Asn Trp Val Asn
1               5

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence:synthetic
      IL15opt-tPA5 signal peptide-altered tPA propeptide-huIL-15
      junction

<400> SEQUENCE: 39

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Asn Trp
        35

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence:synthetic
      IL15opt-tPA5 N-terminal sequence after furin cleavage

<400> SEQUENCE: 40

Gly Ala Asn Trp Val Asn
1               5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:synthetic
      IL15opt-tPA2 4 extra amino acids at the N-terminus after furin
      cleavage

<400> SEQUENCE: 41

Gly Ala Arg Ala
1

<210> SEQ ID NO 42

<211> LENGTH: 271
<212> TYPE: PRT
<213> ORGANISM: Artificial Sequence
<220> FEATURE:
<223> OTHER INFORMATION: Description of Artificial Sequence:synthetic
plasmid expression vector CMV human improved IL-15(opt1)
(CMVhuIL-15(opt1) kanamycin resistance marker

<400> SEQUENCE: 42

```
Met Ser His Ile Gln Arg Glu Thr Ser Cys Ser Arg Pro Arg Leu Asn
 1               5                  10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270
```

<210> SEQ ID NO 43
<211> LENGTH: 26
<212> TYPE: PRT
<213> ORGANISM: Artificial Sequence
<220> FEATURE:
<223> OTHER INFORMATION: Description of Artificial Sequence:synthetic
IL15opt-tPA2 signal peptide-propeptide-huIL-15 junction

<400> SEQUENCE: 43

```
Phe Val Ser Pro Ser Gln Glu Ile His Ala Arg Phe Arg Arg Gly Ala
 1               5                  10                  15

Arg Ala Asn Trp Val Asn Val Ile Ser Asp
            20                  25
```

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence:synthetic
      IL15opt-tPA5 signal peptide-propeptide-huIL-15 junction

<400> SEQUENCE: 44

Phe Val Ser Pro Ser Gln Glu Ile His Ala Arg Phe Arg Arg Gly Ala
 1               5                  10                  15

Asn Trp Val Asn Val Ile Ser Asp
            20

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence:synthetic
      IL15opt-tPA6 signal peptide-propeptide-huIL-15 junction

<400> SEQUENCE: 45

Phe Val Ser Pro Ser Gln Glu Ile His Ala Arg Phe Arg Arg Gly Ala
 1               5                  10                  15

Arg Asn Trp Val Asn Val Ile Ser Asp
            20                  25

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence:synthetic
      IL15opt-tPA7 signal peptide-propeptide-huIL-15 junction

<400> SEQUENCE: 46

Phe Val Ser Pro Ser Gln Glu Ile His Ala Arg Phe Arg Arg Gly Asn
1                5                  10                  15

Trp Val Asn Val Ile Ser Asp
         20

<210> SEQ ID NO 47
<211> LENGTH: 807
<212> TYPE: DNA
<213> ORGANISM: Artificial Sequence
<220> FEATURE:
<223> OTHER INFORMATION: Description of Artificial Sequence:synthetic
      improved human interleukin 15 (IL-15) receptor alpha (IL15Ra),
      transcript variant 1 (OPT)

<400> SEQUENCE: 47
atggccccga ggcgggcgcg aggctgccgg accctcggtc tccggcgcgct gctactgctc      60 ctgctgctcc ggccgccggc gacgcggggc atcacgtgcc cgcccccat gtccgtggag      120 cacgcagaca tctgggtcaa gagctacagc ttgtactccc gggagcggta catctgcaac      180
tcgggtttca gcggaaggc cggcacgtcc agcctgacgg agtgcgtgtt gaacaaggcc      240
acgaatgtcg cccactggac gaccccctcg ctcaagtgca tccgcgaccc ggccctggtt      300
caccagcggc ccgcgccacc ctccaccgta acgacggcgg gggtgacccc gcagccggag      360
agcctctccc cgtcgggaaa ggagcccgcc gcgtcgtcgc ccagctcgaa caacacggcg      420
gccacaactg cagcgatcgt cccggggctcc cagctgatgc cgtcgaagtc gccgtccacg      480
ggaaccacgg agatcagcag tcatgagtcc tcccacggca cccctcgca acgacggcc      540

```
aagaactggg aactcacggc gtccgcctcc caccagccgc cggggggtgta tccgcaaggc    600 cacagcgaca ccacggtggc gatctccacg tccacggtcc tgctgtgtgg gctgagcgcg    660
gtgtcgctcc tggcgtgcta cctcaagtcg aggcagactc ccccgctggc cagcgttgag    720
atggaggcca tggaggctct gccggtgacg tgggggacca gcagcaggga tgaggacttg    780
gagaactgct cgcaccacct ataatga                                       807
```

```
<210> SEQ ID NO 48
<211> LENGTH: 267
<212> TYPE: PRT
<213> ORGANISM: Artificial Sequence
<220> FEATURE:
<223> OTHER INFORMATION: Description of Artificial Sequence:synthetic
      improved human interleukin 15 (IL-15) receptor alpha (IL15Ra),
      transcript variant 1 (OPT)

<400> SEQUENCE: 48
```

```
Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

```
<210> SEQ ID NO 49
<211> LENGTH: 621
<212> TYPE: DNA
<213> ORGANISM: Artificial Sequence
```

<220> FEATURE:
<223> OTHER INFORMATION: Description of Artificial Sequence:synthetic
improved human soluble interleukin 15 (IL-15) receptor alpha
(IL-15sRa) (OPT)

<400> SEQUENCE: 49

```
atggccccga ggcgggcgcg aggctgccgg accctcggtc tcccggcgct gctactgctc      60
ctgctgctcc ggccgccggc gacgcgggc atcacgtgcc cgcccccat gtccgtggag       120
cacgcagaca tctgggtcaa gagctacagc ttgtactccc gggagcggta catctgcaac     180
tcgggtttca gcggaaggc cggcacgtcc agcctgacgg agtgcgtgtt gaacaaggcc      240
acgaatgtcg cccactggac gacccctcg ctcaagtgca tccgcgaccc ggccctggtt      300
caccagcggc ccgcgccacc ctccaccgta acgacggcgg gggtgacccc gcagccggag    360
agcctctccc cgtcgggaaa ggagcccgcc gcgtcgtcgc ccagctcgaa caacacggcg    420
gccacaactg cagcgatcgt cccgggctcc cagctgatgc cgtcgaagtc gccgtccacg    480
ggaaccacgg agatcagcag tcatgagtcc tcccacggca ccccctcgca acgacggcc     540
aagaactggg aactcacggc gtccgcctcc accagccgc cggggggtgta tccgcaaggc    600
cacagcgaca ccacgtaatg a                                               621
```

<210> SEQ ID NO 50
<211> LENGTH: 205
<212> TYPE: PRT
<213> ORGANISM: Artificial Sequence
<220> FEATURE:
<223> OTHER INFORMATION: Description of Artificial Sequence:synthetic
improved human soluble interleukin 15 (IL-15) receptor alpha
(IL-15sRa) (OPT)

<400> SEQUENCE: 50

```
Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205
```

<210> SEQ ID NO 51
<211> LENGTH: 5958
<212> TYPE: DNA
<213> ORGANISM: Artificial Sequence
<220> FEATURE:
<223> OTHER INFORMATION: Description of Artificial Sequence:synthetic dual expression plasmid human IL15Ra+IL15
<220> FEATURE:
<221> NAME/KEY: CDS
<222> LOCATION: (781)..(1587)
<223> OTHER INFORMATION: IL15Ra (from improved human interleukin 15 (IL-15) receptor alpha (IL15Ra), transcript variant 1 (OPT))
<220> FEATURE:
<221> NAME/KEY: CDS
<222> LOCATION: (4695)..(5183)
<223> OTHER INFORMATION: CDS Complement IL-15 (from human improved IL-15 (opt1))

<400> SEQUENCE: 51

```
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg ggaggtctat ataagcagag   660
ctcgtttagt gaaccgtcag atcgcctgga cgccatcc acgctgtttt gacctccata   720
gaagacaccg ggaccgatcc agcctccgcg gccgcgcgtc gaggaattcg ctagcaagaa   780
atggccccga gcgggcgcg aggctgccgg accctcggtc tcccggcgct gctactgctc   840
ctgctgctcc ggccgccggc gacgcgggc atcacgtgcc cgcccccat gtccgtggag   900
cacgcagaca tctgggtcaa gagctacagc ttgtactccc gggagcggta catctgcaac   960
tcgggttca gcggaaggc cggcacgtcc agcctgacgg agtgcgtgtt gaacaaggcc  1020
acgaatgtcg cccactggac gacccccctcg ctcaagtgca tccgcgaccc ggccctggtt  1080
caccagcggc ccgcgccacc ctccaccgta acgacggcgg gggtgacccc gcagccggag  1140
agcctctccc cgtcgggaaa ggagcccgcc gcgtcgtcgc ccagctcgaa caacacggcg  1200
gccacaactg cagcgatcgt cccgggctcc cagctgatgc cgtcgaagtc gccgtccacg  1260
ggaaccacgg agatcagcag tcatgagtcc tcccacggca ccccctcgca acgacggcc  1320
aagaactggg aactcacggc gtccgcctcc caccagccgc cggggggta tccgcaaggc  1380
cacagcgaca ccacggtggc gatctccacg tccacggtcc tgctgtgtgg gctgagcgcg  1440
gtgtcgctcc tggcgtgcta cctcaagtcg aggcagactc cccgctggc cagcgttgag  1500
atggaggcca tggaggctct gccggtgacg tgggggacca gcagcaggga tgaggacttg  1560
gagaactgct cgcaccacct ataatgagaa ttcacgcgtg gatctgatat cggatctgct  1620
gtgccttcta gttgccagcc atctgttgtt tgcccctccc ccgtgccttc cttgaccctg  1680
gaaggtgcca ctcccactgt cctttcctaa taaaatgagg aaattgcatc gcattgtctg  1740
```

```
agtaggtgtc attctattct gggggtgggg gtggggcagg acagcaaggg ggaggattgg    1800
gaagacaata gcaggcatgc tggggatgcg gtgggctcta tgggtaccca ggtgctgaag    1860
aattgacccg gttcctcctg ggccagaaag aagcaggcac atccccttct ctgtgacaca    1920
ccctgtccac gcccctggtt cttagttcca gccccactca taggacactc atagctcagg    1980
agggctccgc cttcaatccc acccgctaaa gtacttggag cggtctctcc ctccctcatc    2040
agcccaccaa accaaaccta gcctccaaga gtgggaagaa attaaagcaa gataggctat    2100
taagtgcaga gggagagaaa atgcctccaa catgtgagga agtaatgaga gaaatcatag    2160
aatttcttcc gcttcctcgc tcactgactc gctgcgctcg gtcgttcggc tgcggcgagc    2220
ggtatcagct cactcaaagg cggtaatacg gttatccaca gaatcagggg ataacgcagg    2280
aaagaacatg tgagcaaaag gccagcaaaa ggccaggaac cgtaaaaagg ccgcgttgct    2340
ggcgtttttc cataggctcc gcccccctga cgagcatcac aaaaatcgac gctcaagtca    2400
gaggtggcga aacccgacag gactataaag ataccaggcg tttccccctg gaagctccct    2460
cgtgcgctct cctgttccga ccctgccgct taccggatac ctgtccgcct ttctcccttc    2520
gggaagcgtg gcgctttctc aatgctcacg ctgtaggtat ctcagttcgg tgtaggtcgt    2580
tcgctccaag ctgggctgtg tgcacgaacc ccccgttcag cccgaccgct gcgccttatc    2640
cggtaactat cgtcttgagt ccaacccggt aagacacgac ttatcgccac tggcagcagc    2700
cactggtaac aggattagca gagcgaggta tgtaggcggt gctacagagt tcttgaagtg    2760
gtggcctaac tacggctaca ctagaaggac agtatttggt atctgcgctc tgctgaagcc    2820
agttaccttc ggaaaaagag ttggtagctc ttgatccggc aaacaaacca ccgctggtag    2880
cggtggtttt tttgtttgca agcagcagat tacgcgcaga aaaaaaggat ctcaagaaga    2940
tcctttgatc ttttctacgg ggtctgacgc tcagtggaac gaaaactcac gttaagggat    3000
tttggtcatg agattatcaa aaaggatctt cacctagatc cttttaaatt aaaaatgaag    3060
ttttaaatca atctaaagta tatatgagta aacttggtct gacagttacc aatgcttaat    3120
cagtgaggca cctatctcag cgatctgtct atttcgttca tccatagttg cctgactcgg    3180 ggggggggg cgctgaggtc tgcctcgtga agaaggtgtt gctgactcat accaggcctg    3240
aatcgcccca tcatccagcc agaaagtgag ggagccacgg ttgatgagag ctttgttgta    3300
ggtggaccag ttggtgattt tgaacttttg ctttgccacg gaacggtctg cgttgtcggg    3360
aagatgcgtg atctgatcct tcaactcagc aaaagttcga tttattcaac aaagccgccg    3420
tcccgtcaag tcagcgtaat gctctgccag tgttacaacc aattaaccaa ttctgattag    3480
aaaaactcat cgagcatcaa atgaaactgc aatttattca tatcaggatt atcaatacca    3540
tatttttgaa aaagccgttt ctgtaatgaa ggagaaaact caccgaggca gttccatagg    3600
atggcaagat cctggtatcg gtctgcgatt ccgactcgtc caacatcaat acaacctatt    3660
aatttcccct cgtcaaaaat aaggttatca agtgagaaat caccatgagt gacgactgaa    3720
tccggtgaga atggcaaaag cttatgcatt tctttccaga cttgttcaac aggccagcca    3780
ttacgctcgt catcaaaatc actcgcatca accaaaccgt tattcattcg tgattgcgcc    3840
tgagcgagac gaaatacgcg atcgctgtta aaggacaat tacaaacagg aatcgaatgc    3900
aaccggcgca ggaacactgc cagcgcatca acaatatttt cacctgaatc aggatattct    3960
tctaatacct ggaatgctgt tttcccgggg atcgcagtgg tgagtaacca tgcatcatca    4020
ggagtacgga taaaatgctt gatggtcgga agaggcataa attccgtcag ccagtttagt    4080
```

| | |
|---|---|
| ctgaccatct catctgtaac atcattggca acgctacctt tgccatgttt cagaaacaac | 4140 |
| tctggcgcat cgggcttccc atacaatcga tagattgtcg cacctgattg cccgacatta | 4200 |
| tcgcgagccc atttataccc atataaatca gcatccatgt tggaatttaa tcgcggcctc | 4260 |
| gagcaagacg tttcccgttg aatatggctc ataacacccc ttgtattact gtttatgtaa | 4320 |
| gcagacagtt ttattgttca tgatgatata tttttatctt gtgcaatgta acatcagaga | 4380 |
| ttttgagaca caacgtggat catccagaca tgataagata cattgatgag tttggacaaa | 4440 |
| ccacaactag aatgcagtga aaaaaatgct ttatttgtga aatttgtgat gctattgctt | 4500 |
| tatttgtaac cattataagc tgcaataaac aagttaacaa caacaattgc attcatttta | 4560 |
| tgtttcaggt tcaggggag gtgtgggagg tttttaaag caagtaaaac ctctacaaat | 4620 |
| gtggtatggc tgattatgat cgtcgaggat ctggatccgt taaccgtatat ccgcgaattc | 4680 |
| ggcgcgccgg gccctcacga cgtgttgatg aacatctgga cgatgtgcac gaacgactgc | 4740 |
| aggaactcct tgatgttctt ctcctccagc tcctcgcact ccttgcagcc cgactccgtg | 4800 |
| acgttcccgt tcgacgacag cgagttgttc gccaggatga tcaggttctc caccgtgtcg | 4860 |
| tggatcgacg cgtcccccga ctcgagcgag atgacttgga gctccaggag aagcacttc | 4920 |
| atcgccgtga ccttgcacga cgggtggacg tccgactccg tgtacagcgt cgcgtcgatg | 4980 |
| tgcatcgact ggatgaggtc ctcgatcttc ttcaggtccg agatcacgtt cacccagttc | 5040 |
| gcctccgtct tcggcagccc cgccgagaag cagcccagga tgaagacgtg tataccggcc | 5100 |
| tccgtgagga agtgcgagtt caggagcagg cacaggtagc actggatcga tatcgaccgc | 5160 |
| aggtgcggct tcgagatccg catttcttgt cgacactcga cagatccaaa cgctcctccg | 5220 |
| acgtccccag gcagaatggc ggttccctaa acgagcattg cttatataga cctcccatta | 5280 |
| ggcacgccta ccgcccattt acgtcaatgg aacgcccatt tgcgtcattg ccctccca | 5340 |
| ttgacgtcaa tggggatgta cttggcagcc atcgcgggcc atttaccgcc attgacgtca | 5400 |
| atgggagtac tgccaatgta ccctggcgta cttccaatag taatgtactt gccaagttac | 5460 |
| tattaataga tattgatgta ctgccaagtg gccatttac cgtcattgac gtcaataggg | 5520 |
| ggcgtgagaa cggatatgaa tgggcaatga gccatcccat tgacgtcaat ggtgggtggt | 5580 |
| cctattgacg tcaatgggca ttgagccagg cgggccattt accgtaattg acgtcaatgg | 5640 |
| gggaggcgcc atatacgtca ataggaccgc ccatatgacg tcaataggaa agaccatgag | 5700 |
| gcccttttcgt ctcgcgcgtt tcggtgatga cggtgaaaac ctctgacaca tgcagctccc | 5760 |
| ggagacggtc acagcttgtc tgtaagcgga tgccgggagc agacaagccc gtcagggcgc | 5820 |
| gtcagcgggt gttggcgggt gtcggggctg gcttaactat gcggcatcag agcagattgt | 5880 |
| actgagagtg caccatatgc ggtgtgaaat accgcacaga tgcgtaagga gaaaataccg | 5940 |
| catcagattg gctattgg | 5958 |

<210> SEQ ID NO 52
<211> LENGTH: 5918
<212> TYPE: DNA
<213> ORGANISM: Artificial Sequence
<220> FEATURE:
<223> OTHER INFORMATION: Description of Artificial Sequence:synthetic
      dual expression plasmid human IL15Ra+IL15tPA6
<220> FEATURE:
<221> NAME/KEY: CDS
<222> LOCATION: (781)..(1587)
<223> OTHER INFORMATION: IL15Ra (from improved human interleukin 15
      (IL-15) receptor alpha (IL15Ra), transcript variant 1 (OPT))
<220> FEATURE:
<221> NAME/KEY: CDS
<222> LOCATION: (4695)..(5183)
<223> OTHER INFORMATION: CDS Complement IL15tPA6 (from tPA6 + human improved IL-15(opt1))

<400> SEQUENCE: 52

```
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg gaggtctat ataagcagag    660
ctcgtttagt gaaccgtcag atcgcctgga cgccatcc acgctgtttt gacctccata    720
gaagacaccg gaccgatcc agcctccgcg ggcgcgcgtc gaggaattcg ctagcaagaa    780
atggccccga ggcgggcgcg aggctgccgg accctcggtc tcccggcgct gctactgctc   840
ctgctgctcc ggccgccggc gacgcgggc atcacgtgcc cgcccccat gtccgtggag     900
cacgcagaca tctgggtcaa gagctacagc ttgtactccc gggagcggta catctgcaac   960
tcgggtttca gcggaaggc cggcacgtcc agcctgacgg agtgcgtgtt gaacaaggcc   1020
acgaatgtcg cccactggac gacccctcg ctcaagtgca tccgcgaccc ggccctggtt   1080
caccagcggc ccgcgccacc ctccaccgta acgacggcgg gggtgacccc gcagccggag   1140
agcctctccc cgtcgggaaa ggagcccgcc gcgtcgtcgc ccagctcgaa caacacggcg   1200
gccacaactg cagcgatcgt cccgggctcc cagctgatgc cgtcgaagtc gccgtccacg   1260
ggaaccacgg agatcagcag tcatgagtcc tcccacggca ccccctcgca acgacggcc   1320
aagaactggg aactcacggc gtccgcctcc caccagccgc cggggggtgta tccgcaaggc   1380
cacagcgaca ccacggtggc gatctccacg tccacggtcc tgctgtgtgg gctgagcgcg   1440
gtgtcgctcc tggcgtgcta cctcaagtcg aggcagactc ccccgctggc cagcgttgag   1500
atggaggcca tggaggctct gccggtgacg tgggggacca gcagcaggga tgaggacttg   1560
gagaactgct cgcaccacct ataatgagaa ttcacgcgtg gatctgatat cggatctgct   1620
gtgccttcta gttgccagcc atctgttgtt tgccctcc ccgtgccttc cttgaccctg    1680
gaaggtgcca ctcccactgt cctttcctaa taaaatgagg aaattgcatc gcattgtctg   1740
agtaggtgtc attctattct ggggggtggg gtggggcagg acagcaaggg ggaggattgg   1800
gaagacaata gcaggcatgc tggggatgcg gtgggctcta tgggtaccca ggtgctgaag   1860
aattgacccg gttcctcctg ggccagaaag aagcaggcac atccccttct ctgtgacaca   1920
ccctgtccac gccctggtt cttagttcca gccccactca taggacactc atagctcagg    1980
agggctccgc cttcaatccc acccgctaaa gtacttggag cggtctctcc ctccctcatc   2040
agcccaccaa accaaaccta gcctccaaga gtgggaagaa attaaagcaa gataggctat   2100
taagtgcaga gggagagaaa atgcctccaa catgtgagga agtaatgaga gaaatcatag   2160
aatttcttcc gcttcctcgc tcactgactc gctgcgctcg gtcgttcggc tgcggcgagc   2220
```

```
ggtatcagct cactcaaagg cggtaatacg gttatccaca gaatcagggg ataacgcagg      2280
aaagaacatg tgagcaaaag gccagcaaaa ggccaggaac cgtaaaaagg ccgcgttgct      2340 ggcgttttc cataggctcc gcccccctga cgagcatcac aaaaatcgac gctcaagtca       2400
gaggtggcga aacccgacag gactataaag ataccaggcg tttccccctg gaagctccct      2460
cgtgcgctct cctgttccga ccctgccgct taccggatac ctgtccgcct ttctcccttc      2520
gggaagcgtg cgctttctc aatgctcacg ctgtaggtat ctcagttcgg tgtaggtcgt       2580
tcgctccaag ctgggctgtg tgcacgaacc ccccgttcag cccgaccgct gcgccttatc      2640
cggtaactat cgtcttgagt ccaacccggt aagacacgac ttatcgccac tggcagcagc     2700
cactggtaac aggattagca gagcgaggta tgtaggcggt gctacagagt tcttgaagtg      2760
gtggcctaac tacggctaca ctagaaggac agtatttggt atctgcgctc tgctgaagcc     2820
agttaccttc ggaaaaagag ttggtagctc ttgatccggc aaacaaacca ccgctggtag     2880
cggtggtttt tttgtttgca agcagcagat tacgcgcaga aaaaaggat ctcaagaaga      2940 tcctttgatc ttttctacgg ggtctgacgc tcagtggaac gaaaactcac gttaagggat     3000
tttggtcatg agattatcaa aaaggatctt cacctagatc cttttaaatt aaaaatgaag     3060
ttttaaatca atctaaagta tatatgagta aacttggtct gacagttacc aatgcttaat    3120
cagtgaggca cctatctcag cgatctgtct atttcgttca tccatagttg cctgactcgg    3180 ggggggggg cgctgaggtc tgcctcgtga agaaggtgtt gctgactcat accaggcctg      3240
aatcgcccca tcatccagcc agaaagtgag ggagccacgg ttgatgagag ctttgttgta     3300
ggtggaccag ttggtgattt tgaacttttg ctttgccacg gaacggtctg cgttgtcggg    3360
aagatgcgtg atctgatcct tcaactcagc aaaagttcga tttattcaac aaagccgccg    3420
tcccgtcaag tcagcgtaat gctctgccag tgttacaacc aattaaccaa ttctgattag     3480
aaaaactcat cgagcatcaa atgaaactgc aatttattca tatcaggatt atcaatacca    3540
tatttttgaa aaagccgttt ctgtaatgaa ggagaaaact caccgaggca gttccatagg    3600
atggcaagat cctggtatcg gtctgcgatt ccgactcgtc caacatcaat acaacctatt     3660
aatttcccct cgtcaaaaat aaggttatca agtgagaaat caccatgagt gacgactgaa     3720
tccggtgaga atggcaaaag cttatgcatt tctttccaga cttgttcaac aggccagcca     3780
ttacgctcgt catcaaaatc actcgcatca accaaaccgt tattcattcg tgattgcgcc    3840
tgagcgagac gaaatacgcg atcgctgtta aaaggacaat tacaaacagg aatcgaatgc     3900
aaccggcgca ggaacactgc cagcgcatca acaatatttt cacctgaatc aggatattct     3960
tctaatacct ggaatgctgt tttcccgggg atcgcagtgg tgagtaacca tgcatcatca     4020
ggagtacgga taaaatgctt gatggtcgga gaggcataa attccgtcag ccagtttagt      4080
ctgaccatct catctgtaac atcattggca acgctacctt tgccatgttt cagaaacaac     4140
tctggcgcat cgggcttccc atacaatcga tagattgtcg cacctgattg cccgacatta     4200
tcgcgagccc atttataccc atataaatca gcatccatgt tggaatttaa tcgcggcctc     4260
gagcaagacg tttcccgttg aatatggctc ataacacccc ttgtattact gtttatgtaa     4320
gcagacagtt ttattgttca tgatgatata tttttatctt gtgcaatgta acatcagaga     4380
ttttgagaca acgtggat catccagaca tgataagata cattgatgag tttggacaaa      4440
ccacaactag aatgcagtga aaaaaatgct tatttgtga aatttgtgat gctattgctt     4500
tatttgtaac cattataagc tgcaataaac aagttaacaa caacaattgc attcatttta     4560
```

```
tgtttcaggt tcaggggag gtgtgggagg ttttttaaag caagtaaaac ctctacaaat     4620
gtggtatggc tgattatgat cgtcgaggat ctggatctgg atccgttaac cgatatccgc     4680
gaattcggcg cgccgggccc tcacgacgtg ttgatgaaca tctggacgat gtgcacgaac     4740
gactgcagga actccttgat gttcttctcc tccagctcct cgcactcctt gcagcccgac     4800
tccgtgacgt tcccgttcga cgacagcgag ttgttcgcca ggatgatcag gttctccacc     4860
gtgtcgtgga tcgacgcgtc ccccgactcg agcgagatga cttggagctc caggaggaag     4920
cacttcatcg ccgtgacctt gcacgacggg tggacgtccg actccgtgta cagcgtcgcg     4980
tcgatgtgca tcgactggat gaggtcctcg atcttcttca ggtccagat cacgttcacc     5040 cagtttctgg ctcctcttct gaatcgggca tggatttcct ggctgggcga aacgaagact     5100
gctccacaca gcagcagcac acagcagagc cctctcttca ttgcatccat ttcttgtcga     5160
cagatccaaa cgctcctccg acgtccccag gcagaatggc ggttccctaa cgagcattg      5220 cttatataga cctcccatta ggcacgccta ccgcccattt acgtcaatgg aacgcccatt     5280
tgcgtcattg cccctcccca ttgacgtcaa tgggatgta cttggcagcc atcgcgggcc      5340
atttaccgcc attgacgtca atggagtac tgccaatgta ccctgcgta cttccaatag       5400 taatgtactt gccaagttac tattaataga tattgatgta ctgccaagtg gccatttac      5460 cgtcattgac gtcaataggg ggcgtgagaa cggatatgaa tgggcaatga gccatcccat     5520
tgacgtcaat ggtgggtggt cctattgacg tcaatgggca ttgagccagg cgggccattt    5580
accgtaattg acgtcaatgg gggaggcgcc atatacgtca ataggaccgc ccatatgacg    5640
tcaataggaa agaccatgag gcccttcgt ctcgcgcgtt tcggtgatga cggtgaaaac      5700
ctctgacaca tgcagctccc ggagacggtc acagcttgtc tgtaagcgga tgccgggagc    5760
agacaagccc gtcagggcgc gtcagcgggt gttggcgggt gtcggggctg cttaactat     5820 gcggcatcag agcagattgt actgagagtg caccatatgc ggtgtgaaat accgcacaga    5880
tgcgtaagga gaaaataccg catcagattg gctattgg                             5918
```

<210> SEQ ID NO 53
<211> LENGTH: 5736
<212> TYPE: DNA
<213> ORGANISM: Artificial Sequence
<220> FEATURE:
<223> OTHER INFORMATION: Description of Artificial Sequence:synthetic dual expression plasmid human IL15sRa(soluble)+IL15tPA6
<220> FEATURE:
<221> NAME/KEY: CDS
<222> LOCATION: (781)..(1587)
<223> OTHER INFORMATION: IL15sRa(soluble) (from improved human soluble interleukin 15 (IL-15) receptor alpha (IL-15sRa) (OPT))
<220> FEATURE:
<221> NAME/KEY: CDS
<222> LOCATION: (4695)..(5183)
<223> OTHER INFORMATION: CDS Complement IL15tPA6 (from tPA6 + human improved IL-15(opt1))

<400> SEQUENCE: 53

```
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
```

```
acggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540 tcaatggag tttgttttgg caccaaaatc aacgggactt tccaaaatgt cgtaacaact      600 ccgcccatt gacgcaaatg gcggtaggc gtgtacggtg ggaggtctat ataagcagag      660
ctcgtttagt gaaccgtcag atcgcctgga gacgccatcc acgctgtttt gacctccata     720
gaagacaccg ggaccgatcc agcctccgcg ggcgcgcgtc gaggaattcg ctagcaagaa     780
atggccccga ggcgggcgcg aggctgccgg accctcggtc tcccggcgct gctactgctc      840
ctgctgctcc ggccgccggc gacgcggggc atcacgtgcc cgccccccat gtccgtggag     900
cacgcagaca tctgggtcaa gagctacagc ttgtactccc gggagcggta catctgcaac     960
tcgggtttca gcggaaggc cggcacgtcc agcctgacgg agtgcgtgtt gaacaaggcc      1020
acgaatgtcg cccactggac gacccccctcg ctcaagtgca tccgcgaccc ggccctggtt    1080
caccagcggc ccgcgccacc ctccaccgta acgacgcgg gggtgacccc gcagccggag     1140
agcctctccc cgtcgggaaa ggagcccgcc gcgtcgtcgc ccagctcgaa caacacggcg    1200
gccacaactg cagcgatcgt cccgggctcc cagctgatgc cgtcgaagtc gccgtccacg    1260
ggaaccacgg agatcagcag tcatgagtcc tcccacggca cccctcgca aacgacggcc     1320 aagaactggg aactcacggc gtccgcctcc caccagccgc cggggggtgta ccgcaaggc     1380 cacagcgaca ccacgtaatg agaattcgcg gatatcggtt aacggatcca gatctgctgt     1440
gccttctagt tgccagccat ctgttgtttg cccctcccc gtgccttcct tgaccctgga      1500
aggtgccact cccactgtcc tttcctaata aaatgaggaa attgcatcgc attgtctgag     1560
taggtgtcat tctattctgg ggggtgggt ggggcaggac agcaagggg aggattggga      1620 agacaatagc aggcatgctg gggatgcggt gggctctatg ggtacccagg tgctgaagaa    1680
ttgacccggt tcctcctggg ccagaaagaa gcaggcacat cccctctct gtgacacacc      1740 ctgtccacgc ccctggttct tagttccagc cccactcata ggacactcat agctcaggag    1800
ggctccgcct tcaatcccac ccgctaaagt acttggagcg gtctctccct ccctcatcag     1860
cccaccaaac caaacctagc ctccaagagt gggaagaaat taaagcaaga taggctatta    1920
agtgcagagg gagagaaaat gcctccaaca tgtgaggaag taatgagaga atcatagaa      1980 tttcttccgc ttcctcgctc actgactcgc tgcgctcggt cgttcggctg cggcgagcgg    2040
tatcagctca ctcaaaggcg gtaatacggt tatccacaga atcagggat aacgcaggaa      2100 agaacatgtg agcaaaaggc cagcaaaagg ccaggaaccg taaaaaaggcc gcgttgctgg   2160 cgtttttcca taggctccgc cccctgacg agcatcacaa aatcgacgc tcaagtcaga     2220 ggtggcgaaa cccgacagga ctataaagat accaggcgtt tcccctgga agctccctcg      2280 tgcgctctcc tgttccgacc ctgccgctta ccggatacct gtccgccttt ctcccttcgg    2340
gaagcgtggc gctttctcaa tgctcacgct gtaggtatct cagttcggtg taggtcgttc    2400
gctccaagct gggctgtgtg cacgaaccc ccgttcagcc cgaccgctgc gccttatccg    2460
gtaactatcg tcttgagtcc aacccggtaa gacacgactt atcgccactg gcagcagcca   2520
ctggtaacag gattagcaga gcgaggtatg taggcggtgc tacagagttc ttgaagtggt    2580
ggcctaacta cggctacact agaaggacag tatttggtat ctgcgctctg ctgaagccag    2640
ttaccttcgg aaaaagagtt ggtagctctt gatccggcaa acaaaccacc gctggtagcg   2700 gtggttttttt tgtttgcaag cagcagatta cgcgcagaaa aaaaggatct caagaagatc   2760
```

```
ctttgatctt ttctacgggg tctgacgctc agtggaacga aaactcacgt taagggattt    2820
tggtcatgag attatcaaaa aggatcttca cctagatcct tttaaattaa aaatgaagtt    2880
ttaaatcaat ctaaagtata tatgagtaaa cttggtctga cagttaccaa tgcttaatca    2940
gtgaggcacc tatctcagcg atctgtctat ttcgttcatc catagttgcc tgactcgggg    3000
ggggggggcg ctgaggtctg cctcgtgaag aaggtgttgc tgactcatac caggcctgaa    3060
tcgccccatc atccagccag aaagtgaggg agccacggtt gatgagagct tgttgtagg     3120
tggaccagtt ggtgattttg aacttttgct ttgccacgga acggtctgcg ttgtcgggaa    3180
gatgcgtgat ctgatccttc aactcagcaa aagttcgatt tattcaacaa agccgccgtc    3240
ccgtcaagtc agcgtaatgc tctgccagtg ttacaaccaa ttaaccaatt ctgattagaa    3300
aaactcatcg agcatcaaat gaaactgcaa tttattcata tcaggattat caataccata    3360
tttttgaaaa agccgtttct gtaatgaagg agaaaactca ccgaggcagt tccataggat    3420
ggcaagatcc tggtatcggt ctgcgattcc gactcgtcca acatcaatac aacctattaa    3480
tttcccctcg tcaaaaataa ggttatcaag tgagaaatca ccatgagtga cgactgaatc    3540
cggtgagaat ggcaaaagct tatgcatttc tttccagact tgttcaacag gccagccatt    3600
acgctcgtca tcaaaatcac tcgcatcaac caaaccgtta ttcattcgtg attgcgcctg    3660
agcgagacga aatacgcgat cgctgttaaa aggacaatta caaacaggaa tcgaatgcaa    3720
ccggcgcagg aacactgcca gcgcatcaac aatattttca cctgaatcag gatattcttc    3780
taatacctgg aatgctgttt tcccggggat cgcagtggtg agtaaccatg catcatcagg    3840
agtacggata aaatgcttga tggtcggaag aggcataaat tccgtcagcc agtttagtct    3900
gaccatctca tctgtaacat cattggcaac gctaccttg ccatgtttca gaaacaactc     3960
tggcgcatcg ggcttcccat acaatcgata gattgtcgca cctgattgcc cgacattatc    4020
gcgagcccat ttatacccat ataaatcagc atccatgttg gaatttaatc gcggcctcga    4080
gcaagacgtt tcccgttgaa tatggctcat aacacccctt gtattactgt ttatgtaagc    4140
agacagtttt attgttcatg atgatatatt tttatcttgt gcaatgtaac atcagagatt    4200
ttgagacaca acgtggatca tccagacatg ataagataca ttgatgagtt tggacaaacc    4260
acaactagaa tgcagtgaaa aaaatgcttt atttgtgaaa tttgtgatgc tattgcttta    4320
tttgtaacca ttataagctg caataaacaa gttaacaaca acaattgcat tcattttatg    4380
tttcaggttc aggggaggt gtgggaggtt ttttaaagca agtaaaacct ctacaaatgt      4440
ggtatgctg attatgatcg tcgaggatct ggatctggat ccgttaaccg atatccgcga     4500
attcggcgcg ccgggccctc acgacgtgtt gatgaacatc tggacgatgt gcacgaacga    4560
ctgcaggaac tccttgatgt tcttctcctc cagctcctcg cactccttgc agcccgactc    4620
cgtgacgttc ccgttcgacg acagcgagtt gttcgccagg atgatcaggt tctccaccgt    4680
gtcgtggatc gacgcgtccc ccgactcgag cgagatgact tggagctcca ggaggaagca    4740
cttcatcgcc gtgaccttgc acgacgggtg gacgtccgac tccgtgtaca gcgtcgcgtc    4800
gatgtgcatc gactggatga ggtcctcgat cttcttcagg tccgagatca cgttcaccca    4860
gtttctggct cctcttctga atcgggcatg gatttcctgg ctgggcgaaa cgaagactgc    4920
tccacacagc agcagcacac agcagagccc tctcttcatt gcatccattt cttgtcgaca    4980
gatccaaacg ctcctccgac gtccccaggc agaatggcgg ttccctaaac gagcattgct    5040
tatatagacc tcccattagg cacgcctacc gcccatttac gtcaatggaa cgcccatttg    5100
```

```
cgtcattgcc cctccccatt gacgtcaatg gggatgtact tggcagccat cgcgggccat    5160
ttaccgccat tgacgtcaat gggagtactg ccaatgtacc ctggcgtact tccaatagta    5220
atgtacttgc caagttacta ttaatagata ttgatgtact gccaagtggg ccatttaccg    5280
tcattgacgt caataggggg cgtgagaacg gatatgaatg ggcaatgagc catcccattg    5340
acgtcaatgg tgggtggtcc tattgacgtc aatgggcatt gagccaggcg ggccatttac    5400
cgtaattgac gtcaatgggg gaggcgccat atacgtcaat aggaccgccc atatgacgtc    5460
aataggaaag accatgaggc cctttcgtct cgcgcgtttc ggtgatgacg gtgaaaacct    5520
ctgacacatg cagctcccgg agacggtcac agcttgtctg taagcggatg ccgggagcag    5580
acaagcccgt cagggcgcgt cagcgggtgt tggcgggtgt cggggctggc ttaactatgc    5640
ggcatcagag cagattgtac tgagagtgca ccatatgcgg tgtgaaatac cgcacagatg    5700
cgtaaggaga aataccgca tcagattggc tattgg                              5736
```

CODON OPTIMIZED IL-15 AND IL-15R-ALPHA GENES FOR EXPRESSION IN MAMMALIAN CELLS

CROSS-REFERENCE TO RELATED PATENT APPLICATIONS

The present application is the divisional of U.S. patent application Ser. No. 12/160,263, filed Jul. 8, 2008, which is U.S. National Stage entry of International Application No. PCT/US07/00774, filed Jan. 12, 2007, which claims the benefit of U.S. Provisional Patent Application Nos. 60/812,566, filed on Jun. 9, 2006 and 60/758,819, filed on Jan. 13, 2006, the entire contents of each of which are hereby incorporated herein by reference for all purposes

REFERENCE TO SEQUENCE LISTING SUBMITTED AS TEXT FILE

This application includes a Sequence Listing as a text file named "77867-946361-SEQLIST.txt" created Jun. 11, 2015, and containing 80,299 bytes. The material contained in the text file is herein incorporated by reference.

FIELD OF THE INVENTION

The present invention relates to improved cytokine expression in mammalian cells by optimizing all steps of gene expression of the cytokine.

BACKGROUND OF THE INVENTION

Interleukin-15 (IL-15) is a pleiotropic cytokine important for both the innate and adaptive immune systems (Diab, et al., *Cytotherapy* (2005) 7:23-35). IL-15 promotes the activation of neutrophils and macrophages, and is essential to the development and function of dendritic cells (DC), natural killer (NK) cells, NK T cells, and CD8+ T cells (Id.). IL-15 acts on cells in both lymphoid and non-lymphoid compartments (Van Belle and Grooten, *Arch Immunol Ther Exp* (2005) 53:115).

Based on its many functions and relative safety in animal models, administration of IL-15 finds use in treating immunodeficiency, for the in vitro expansion of T cells and NK cells, and as an adjuvant for vaccines, including anti-HIV vaccines (Diab,et al., supra; Ahmad, et al., *Curr HIV Res* (2005) 3:261; Alpdogan and van den Brink, *Trends Immunol* (2005) 26:56). For example, administration of exogenous IL-15 has been found to drastically enhance the immune cell functions of human immunodeficiency virus (HIV)-infected Acquired Immune Deficiency Syndrome (AIDS) patients (Ahmad, et al., supra; see also, Pett and Kelleher, *Expert Rev Anti Infect Ther* (2003) 1:83; and Ansari, et al., *Immunol Res* (2004) 29:1). Administration of IL-15 for its effects on lymphopoiesis and the treatment of immunodeficiency disorders is also being explored (Alpdogan and van den Brink, supra).

Results from several investigators have suggested that the natural soluble form of IL-15 Receptor alpha is an antagonist of IL-15 (see, Mortier, et al., (2004) *J. Immunol.* 173, 1681-1688; Ruchatz, et al., (1998) *J. Immunol.* 160, 5654-566; and Smith, et al., (2000) J. Immunol. 165, 3444-3450). In contrast, the sushi domain of IL-15 Receptor alpha when fused to IL-15 via a flexible amino acid linker has been proposed as an agonist of IL-15 function in vitro (J Biol Chem. 2006 Jan. 20; 281(3):1612-9). Soluble interleukin-15 receptor alpha (IL-15R alpha)-sushi is a selective and potent agonist of IL-15 action through IL-15R beta/gamma (see, Mortier E, et al., *J Biol Chem.* 2006 281:1612).

To provide therapeutic IL-15, alone or in combination with a whole IL-15 receptor alpha or a soluble IL-15 receptor alpha, either for administration as a coding nucleic acid or as a protein, it is important to develop efficient expression vectors and efficiently expression coding nucleic acid sequences for this cytokine. The present invention addresses this need.

BRIEF SUMMARY OF THE INVENTION

The present invention provides nucleic acid sequences, expression vectors and mammalian cells for the high-level expression of interleukin-15 (IL-15), alone and combined with whole IL-15 Receptor alpha (IL15Ra) or the soluble form of IL15Ra (IL15sRa). The invention further provides methods for the high-level expression of interleukin-15 in mammalian cells, alone and combined with whole IL-15 Receptor alpha (IL15Ra) or the soluble form of IL15Ra (IL15sRa).

In a related aspect, the invention provides nucleic acid sequences, expression vectors and mammalian cells for the high-level expression of whole IL-15 Receptor alpha (IL15Ra) or the soluble form of IL15Ra (IL15sRa). The invention further provides methods for the high-level expression whole IL-15 Receptor alpha (IL15Ra) or the soluble form of IL15Ra (IL15sRa).

In one aspect, the invention provides nucleic acid sequences encoding an interleukin-15 (IL-15) protein having at least 90%, 91%, 92%, 93%, 94%, 95%, 96%, 97%, 98%, 99% sequence identity to a native mammalian IL-15 protein, wherein the nucleic acid sequence differs from a nucleic acid sequence encoding the native mammalian IL-15 by at least 50% of the changed nucleotide positions identified in FIG. 8. In some embodiments, the nucleic acid sequence differs from a nucleic acid sequence encoding the native mammalian IL-15 by at least 50% of the changed codon positions identified in FIG. 4 and/or in FIG. 6. In some embodiments, the changed nucleotides and codons are in the mature IL-15 sequence. The native mammalian IL-15 can be any mammalian IL-15, including human IL-15, a primate IL-15, a porcine IL-15, a murine IL-15, and the like.

In some embodiments, the nucleic acid sequence encoding the IL-15 differs from a nucleic acid sequence encoding the native IL-15 by at least about 55% (e.g., 59 nucleotides), 60% (e.g., 64 nucleotides), 65% (e.g., 70 nucleotides), 70% e.g., (75 nucleotides), 75% (e.g., 81 nucleotides), 80% (e.g., 86 nucleotides), 85% (e.g., 91 nucleotides), 90% (e.g., 97 nucleotides), 95% (e.g., 109 nucleotides) of the 115 changed nucleotide positions identified in FIG. 8 (shaded). In some embodiments, the nucleic acid sequence encoding the IL-15 differs from a nucleic acid sequence encoding the native IL-15 by at least about 55% (e.g., 66 codons), 60% (e.g., 73 codons), 65% (e.g., 78 codons), 70% e.g., (85 codons), 75% (e.g., 91 codons), 80% (e.g., 97 codons), 85% (e.g., 103 codons), 90% (e.g., 109 codons), 95% (e.g., 115 codons) of the 121 changed codon positions identified in FIG. 4 (shaded, boxed or underlined).

In some embodiments, the changed nucleotides and codons are in the mature IL-15 sequence. For example, the nucleic acid sequence encoding the improved IL-15 can differ from a nucleic acid sequence encoding the native IL-15 by at least about 65%, 70% , 75% , 80%, 85%, 90%, 95% of the 78 changed nucleotide positions in the mature IL-15 identified in FIG. 8 (shaded). In another embodiment, the nucleic acid sequence encoding the improved IL-15 can differ from a nucleic acid sequence encoding the native IL-15 by at least about 65%, 70%, 75%, 80%, 85%, 90%, 95% of the 84 changed codon positions in the mature IL-15 identified in FIG. 4 (shaded, boxed or underlined).

In some embodiments, the nucleic acid sequence differs from a nucleic acid sequence encoding the native IL-15 at nucleotide positions 6, 9, 15, 18, 21, 22, 27, 30, 33, 49, 54, 55, 57, 60, 63, 69, 72, 75, 78, 81, 84, 87, 90, 93, 96, 105, 106, 114, 120, 123, 129, 132, 135, 138, 141, 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486, wherein the nucleotide positions are as identified in FIG. 8.

In some embodiments, the nucleic acid sequence comprises a guanine (g) or a cytosine (c) nucleotide at nucleotide positions 6, 9, 15, 18, 21, 22, 27, 30, 33, 49, 54, 55, 57, 60, 63, 69, 72, 75, 78, 81, 84, 87, 96, 105, 106, 114, 120, 123, 129, 132, 135, 138, 141, 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486, wherein the nucleotide positions are as identified in FIG. 8.

The codons can differ in any way such that an identical or similar (i.e., conservatively substituted) amino acid is encoded. In some embodiments, the codons are changed to increase GC content. In some embodiments, the improved IL-15 nucleic acid sequences each comprise at least about 50%, 55%, 60%, 65%, 70%, 75% or more GC content (e.g., deoxyguanosine and deoxycytidine deoxyribonucleoside residues or guanosine and cytidine ribonucleoside residues) over the length of the sequence.

The nucleic acid encoding the IL-15 can share at least 90%, 91%, 92%, 93%, 94%, 95%, 96%, 97%, 98%, 99% sequence identity with a nucleic acid of SEQ ID NO:3, SEQ ID NO:4, and/or SEQ ID NO:16. In some embodiments, the nucleic acid sequence encoding the IL-15 differs from a nucleic acid sequence encoding the native IL-15 as identified in FIG. 8 (SEQ ID NO:3 or SEQ ID NO:4) or FIG. 16 (SEQ ID NO:16).

In some embodiments, the nucleic acid sequence encoding an IL-15 signal peptide-propeptide (SIG-PRO) is replaced with a nucleic acid sequence encoding a signal peptide (SIG) or a signal peptide-propeptide (SIG-PRO) from a heterologous protein. In some embodiments, the nucleic acid sequence encoding an IL-15 signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). In one embodiment, the nucleic acid sequence encoding an IL-15 signal peptide-propeptide (SIG-PRO) is replaced with a nucleic acid sequence encoding a tPA SIG-PRO having 95% sequence identity to SEQ ID NO:6, SEQ ID NO:8, SEQ ID NO:25 or SEQ ID NO:27. In some embodiments, the nucleic acid encoding the IL-15 is operably linked to a nucleic acid encoding an RNA export element, for example a CTE or RTEm26CTE.

In some embodiments, the nucleic acid sequence encoding an IL15Ra signal peptide is replaced with a nucleic acid sequence encoding a signal peptide (SIG) or a signal peptide-propeptide (SIG-PRO) from a heterologous protein. In some embodiments, the nucleic acid sequence encoding an IL15Ra signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). In some embodiments, the nucleic acid encoding the IL15Ra is operably linked to a nucleic acid encoding an RNA export element, for example a CTE or RTEm26CTE.

In another aspect, the invention provides nucleic acid sequences encoding a signal peptide-propeptide (SIG-PRO) sequence from a protein other than IL-15, for example a tPA SIG-PRO sequence, a growth hormone signal sequence (SIG), an immunoglobulin signal sequence (SIG), operably linked to a nucleic acid encoding an IL-15 protein having at least 90% sequence identity to the native mammalian IL-15 protein, wherein the nucleic acid sequence encoding IL-15 comprises at least 50% GC content. In one embodiment, the SIG-PRO sequence is from a protein selected from the group consisting of tPA, GM-CSF, growth hormone and an immunoglobulin family protein. In one embodiment, the SIG-PRO sequence encodes a tPA SIG-PRO having at least 95% amino acid sequence identity to SEQ ID NO:6 or SEQ ID NO:8. In another embodiment, the SIG-PRO sequence is a tPA SIG-PRO having at least 95% nucleic acid sequence identity to SEQ ID NO:5 or SEQ ID NO:7. Further embodiments are as described above.

In a further aspect, the invention includes expression vectors and mammalian cells comprising the nucleic acid sequences of the invention, including the embodiments described above.

In some embodiments, the nucleic acid sequences encoding the IL-15 and/or IL15Ra further include pharmaceutical excipients for use as a vaccine adjuvant. In some embodiments, the nucleic acid sequences encoding the IL-15 and/or IL15Ra further include pharmaceutical excipients for use as an immunotherapy factor, for example, in the expansion of the numbers of lymphocytes, including B-cells, T cells, NK cells, and NK T cells, in vitro or in vivo. In some embodiments, the IL-15 and/or IL15Ra nucleic acid sequences are used to expand lymphocyte populations that express the IL-2/IL-15 beta gamma receptors. In some embodiments, the IL-15 and/or IL15Ra nucleic acid sequences are used to expand CD4+ and/or CD8+ T cells. In some embodiments, the IL-15 and/or IL15Ra nucleic acid sequences are used to expand the numbers of dual secreting IL-2 and IFN-gamma multifunctional cells (e.g., multifunctional T cells) after antigenic stimulation.

In a another aspect, the invention provides methods of expressing IL-15 in a mammalian cell, the method comprising recombinantly modifying a mammalian cell to express a nucleic acid encoding an IL-15 protein having at least 90%, 91%, 92%, 93%, 94%, 95%, 96%, 97%, 98%, 99% sequence identity to a native mammalian IL-15 protein, wherein the nucleic acid sequence differs from a nucleic acid sequence encoding the native mammalian IL 15 by at least 50% of the nucleotide positions identified in FIG. 8. The embodiments for the methods are as described above for the nucleic acid sequences.

In a related aspect, the present invention is based, in part, on the discovery that the whole IL-15 Receptor alpha (IL15Ra) or the soluble form of IL15Ra (IL15sRa) comprising the entire extracellular domain of the receptor is a potent stabilizer of IL-15 in vitro and in vivo. The complex of IL-15 and IL15sRa has increased stability in circulation and also has increased IL-15 potency as determined by the expansion of multiple lymphocyte subsets including natural killer (NK) cells and T cells. The present invention provides methods, expression vectors and protein combinations that increase IL-15 potency in vitro and in vivo. These methods are useful for the increased bioavailability, stability, and potency of IL-15, and for increasing the biological effects of IL-15 upon administration to an individual (e.g., a mammal, a human).

Provided are expression vectors for the co-ordinate expression of IL-15 with its receptor IL-15 Receptor alpha (IL15Ra). The vectors generally contain one copy of an IL-15 coding sequence or/and one copy of an IL-15 Receptor alpha (IL15Ra) (whole or soluble). The expression ratios of the two proteins can be adjusted to 1:1, 1:2 or 1:3, for example, by using different plasmid DNA ratios (w/w) or by selecting promoters of different expression strengths. In some embodiments, the IL-15 cytokine and IL-15 Receptor alpha (IL15Ra) are expressed in a molar ratio of 1:3.

In one embodiment, the nucleic acid sequences for at least one of the IL-15 cytokine and IL-15 Receptor alpha (IL15Ra) are improved in accordance with the present methods described herein. Co-expression of the IL-15 cytokine and IL-15 Receptor alpha (IL15Ra), whole or soluble, increases the amount of IL-15 cytokine and IL15Ra that is expressed and secreted from a cell, by more than 10-fold, 100-fold, 10,000-fold, 100,000-fold, 1,000,000-fold or more, in comparison to expression of IL-15 alone, particularly in comparison to wt IL-15 sequences. Using such vectors increases the stability of IL-15 and IL15Ra by more than 10-fold, 20-fold, 50-fold, 100-fold, 1000-fold or more, in comparison to IL-15 alone, and increases the steady-state levels of IL-15 protein in vivo. The biological function (e.g., the activation and induction of the expansion of lymphocytes, including B cells, T cells, natural killer (NK) cells and NK T cells) of IL-15 co-expressed with IL15Ra is also dramatically increased in vivo, by more than 10-fold, 15-fold, 20-fold, or more, in comparison to IL-15 alone. These vectors are useful for the increased delivery of biologically active cytokines in specific tissues. The IL-15 and IL15Ra vectors and proteins find use in prophylactic and therapeutic vaccinations, cancer immunotherapy, or for any indication for enhanced lymphocyte numbers and function and any immune deficiency conditions.

In one aspect, the present invention provides expression vectors for the coordinate expression of IL-15 with whole IL15Ra or soluble IL15Ra. The IL-15 and whole IL15Ra or soluble IL15Ra can be contained in the same expression vector or in multiple expression vectors. In some embodiments, the coding nucleic acid sequence of at least one of the IL-15 and whole IL15Ra or soluble IL15Ra is improved according to the present methods for high efficiency expression.

One aspect of the invention is that the provided vectors expressing IL-15 and full length IL15Ra upon delivery to a mammalian cell or a mammal can rapidly generate the native form of soluble extracellular IL15sRa. Therefore, co-delivery and expression of IL-15 and IL15Ra generates IL-15/IL-15R complexes on the surface of the cell as well as IL-15/IL15sRa complexes that are released into circulation and can act at distant tissues.

In a further aspect, the invention provides improved nucleic acid sequences encoding a whole IL-15 Receptor alpha (IL15Ra) or the soluble form of IL15Ra (IL15sRa) having at least 90%, 91%, 92%, 93%, 94%, 95%, 96%, 97%, 98%, 99% sequence identity to a native mammalian IL-15 Receptor alpha (IL15Ra) or the soluble form of IL15Ra (IL15sRa) protein (see, e.g., NM_002189), wherein the nucleic acid sequence differs from a nucleic acid sequence encoding the native mammalian IL-15 by at least 50% of the changed nucleotide positions identified in FIGS. 35-38.

In some embodiments, the coding sequence for the IL15Ra (whole or soluble form) shares at least 90%, 95%, 96%, 97%, 98% or 99% sequence identity with a nucleic acid sequence depicted in any one of FIGS. 35-38. In one embodiment, the IL15Ra is encoded by the nucleic acid sequence depicted in any one of FIGS. 35-38. In one embodiment, the improved IL15Ra (whole or soluble) coding nucleic acid sequence has at least 50%, 55%, 60%, 65%, 70%, 75%, 80% or 85% GC content.

The invention further provides methods of increasing IL-15 quantity, stability and bioactivity. The methods can be carried out in vitro by co-expressing IL-15 and IL15Ra or IL15sRa in mammalian host cells. The methods can be carried out in vivo by administering to an individual a combination of IL-15 with an IL-15 receptor alpha (whole or soluble), as proteins for injection or as DNA constructs (native or improved) that are produced in vivo. One or both of the IL-15 and IL15Ra coding sequences can be improved according to the methods described herein.

The invention further provides host cells and cell lines that coordinately produce IL-15 and IL-15 soluble Receptor alpha (IL15sRa) or cell lines coordinately producing IL-15 and a mixture of soluble and full length IL15Ra.

In a further aspect, the invention provides methods of enhancing the immune response of an individual against one or more antigens by administering an improved IL-15 nucleic acid of the invention, alone or in combination with an IL15Ra. The IL15Ra can be in protein or nucleic acid form, wild-type or improved.

In a further aspect, the invention provides methods of expanding the numbers of lymphocytes, for example, for decreasing immunodeficiency conditions, in vivo or in vitro, by administering an improved IL-15 nucleic acid of the invention, alone or in combination with an IL15Ra. The IL15Ra can be in protein or nucleic acid form, wild-type or improved. In some embodiments, the lymphocytes are selected from the group consisting of B-cells, T cells, NK cells, and NK T cells. In some embodiments, the IL-15 and/or IL15Ra nucleic acid sequences promote the expansion of lymphocyte populations that express the IL-2/IL-15 beta gamma receptors. In some embodiments, the IL-15 and/or IL15Ra nucleic acid sequences stimulate the expansion of CD4+ and/or CD8+ T cells. In some embodiments, the IL-15 and/or IL15Ra nucleic acid sequences induce the expansion of the numbers of dual secreting IL-2 and IFN-gamma multifunctional cells (e.g., multifunctional T cells) upon antigen stimulation.

In some embodiments, one or both of the DNA constructs are administered by injection and/or electroporation. Administration by dual routes of injection and electroporation can be done concurrently or sequentially, at the same or different sites.

DEFINITIONS

The term "native mammalian interleukin-15 (IL-15)" refers to any naturally occurring interleukin-15 nucleic acid and amino acid sequences of the IL-15 from a mammalian species. Those of skill in the art will appreciate that interleukin-15 nucleic acid and amino acid sequences are publicly available in gene databases, for example, GenBank through the National Center for Biotechnological Information on the worldwideweb at ncbi.nlm.nih.gov. Exemplified native mammalian IL-15 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-15 nucleic acid sequences include NM_172174 (human; SEQ ID NO:1); NM_172175 (human); NM_000585 (human); U19843 (macaque; SEQ ID NO:14); DQ021912 (macaque); AB000555 (macaque); NM_214390 (porcine); DQ152967 (ovine); NM 174090 (bovine); NM 008357 (murine); NM 013129 (rattus); DQ083522 (water buffalo); XM_844053 (canine); DQ157452 (lagomorpha); and NM_001009207 (feline). Accession numbers for exemplified native mammalian IL-15 amino acid sequences include NP_751914 (human; SEQ ID NO:2); CAG46804 (human); CAG46777 (human); AAB60398 (macaque; SEQ ID NO:15); AAY45895 (macaque); NP_999555 (porcine); NP_776515 (bovine); AAY83832 (water buffalo); ABB02300 (ovine); XP_849146 (canine); NP_001009207 (feline); NP_037261 (rattus); and NP_032383 (murine).

The term "interleukin-15" or "IL-15" refers to a polypeptide that has at least 90%, 91%, 92%, 93%, 94%, 95%, 96%, 97%, 98% or 99% sequence identity to a native mammalian IL-15 amino acid sequence, or a nucleotide encoding such a polypeptide, is biologically active, meaning the mutated protein ("mutein") has functionality similar (75% or greater) to that of a native IL-15 protein in at least one functional assay. Exemplified functional assays of an IL-15 polypeptide include proliferation of T-cells (see, for example, Montes, et al., *Clin Exp Immunol* (2005) 142:292), and activation of NK cells, macrophages and neutrophils. Methods for isolation of particular immune cell subpopulations and detection of proliferation (i.e., $^3$H-thymidine incorporation) are well known in the art. Cell-mediated cellular cytotoxicity assays can be used to measure NK cell, macrophage and neutrophil activation. Cell-mediated cellular cytotoxicity assays, including release of isotopes ($^{51}$Cr), dyes (e.g., tetrazolium, neutral red) or enzymes, are also well known in the art, with commercially available kits (Oxford Biomedical Research, Oxford, M; Cambrex, Walkersville, Md.; Invitrogen, Carlsbad, Calif.). IL-15 has also been shown to inhibit Fas mediated apoptosis (see, Demirci and Li, *Cell Mol Immunol* (2004) 1:123). Apoptosis assays, including for example, TUNEL assays and annexin V assays, are well known in the art with commercially available kits (R&D Systems, Minneapolis, Minn.). See also, Coligan, et al., *Current Methods in Immunology*, 1991-2006, John Wiley & Sons.

The term "native mammalian interleukin-15 Receptor alpha (IL15Ra)" refers to any naturally occurring interleukin-15 receptor alpha nucleic acid and amino acid sequences of the IL-15 receptor alpha from a mammalian species. Those of skill in the art will appreciate that interleukin-15 receptor alpha nucleic acid and amino acid sequences are publicly available in gene databases, for example, GenBank through the National Center for Biotechnological Information on the worldwideweb at ncbi.nlm.nih.gov. Exemplified native mammalian IL-15 receptor alpha nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-15 nucleic acid sequences include NM_002189 (*Homo sapiens* interleukin 15 receptor, alpha (IL15RA), transcript variant 1, mRNA).

The term "interleukin-15 receptor alpha" or "IL15Ra" refers to a polypeptide that has at least 90%, 91%, 92%, 93%, 94%, 95%, 96%, 97%, 98% or 99% sequence identity to a native mammalian IL15Ra amino acid sequence, or a nucleotide encoding such a polypeptide, is biologically active, meaning the mutated protein ("mutein") has functionality similar (75% or greater) to that of a native IL15Ra protein in at least one functional assay. One functional assay is specific binding to a native IL-15 protein.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Degenerate codon substitutions for naturally occurring amino acids are in Table 1.

TABLE 1

| $1^{st}$ position | $2^{nd}$ position | | | | $3^{rd}$ position |
|---|---|---|---|---|---|
| (5' end) | U(T) | C | A | G | (3' end) |
| U(T) | Phe | Ser | Tyr | Cys | U(T) |
|  | Phe | Ser | Tyr | Cys | C |
|  | Leu | Ser | STOP | STOP | A |
|  | Leu | Ser | STOP | Trp | G |
| C | Leu | Pro | His | Arg | U(T) |
|  | Leu | Pro | His | Arg | C |
|  | Leu | Pro | Gln | Arg | A |
|  | Leu | Pro | Gln | Arg | G |
| A | Ile | Thr | Asn | Ser | U(T) |
|  | Ile | Thr | Asn | Ser | C |
|  | Ile | Thr | Lys | Arg | A |
|  | Met | Thr | Lys | Arg | G |
| G | Val | Ala | Asp | Gly | U(T) |
|  | Val | Ala | Asp | Gly | C |
|  | Val | Ala | Glu | Gly | A |
|  | Val | Ala | Glu | Gly | G |

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of SEQ ID NOs:1-23), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of am amino acid or nucleic acid sequences.

For sequence comparison, typically one sequence acts as a reference sequence, to which test sequences are compared (here, an entire "native mammalian" IL-15 amino acid or nucleic acid sequence). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The term "GC content" refers to the percentage of a nucleic acid sequence comprised of deoxyguanosine (G) and/or deoxycytidine (C) deoxyribonucleosides, or guanosine (G) and/or cytidine (C) ribonucleoside residues.

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

The term "operably linked" refers to a functional linkage between a first nucleic acid sequence and a second nucleic acid sequence, such that the first and second nucleic acid sequences are transcribed into a single nucleic acid sequence. Operably linked nucleic acid sequences need not be physically adjacent to each other. The term "operably linked" also refers to a functional linkage between a nucleic acid expression control sequence (such as a promoter, or array of transcription factor binding sites) and a transcribable nucleic acid sequence, wherein the expression control sequence directs transcription of the nucleic acid corresponding to the transcribable sequence.

BRIEF DESCRIPTION OF THE DRAWINGS

Figure 3:
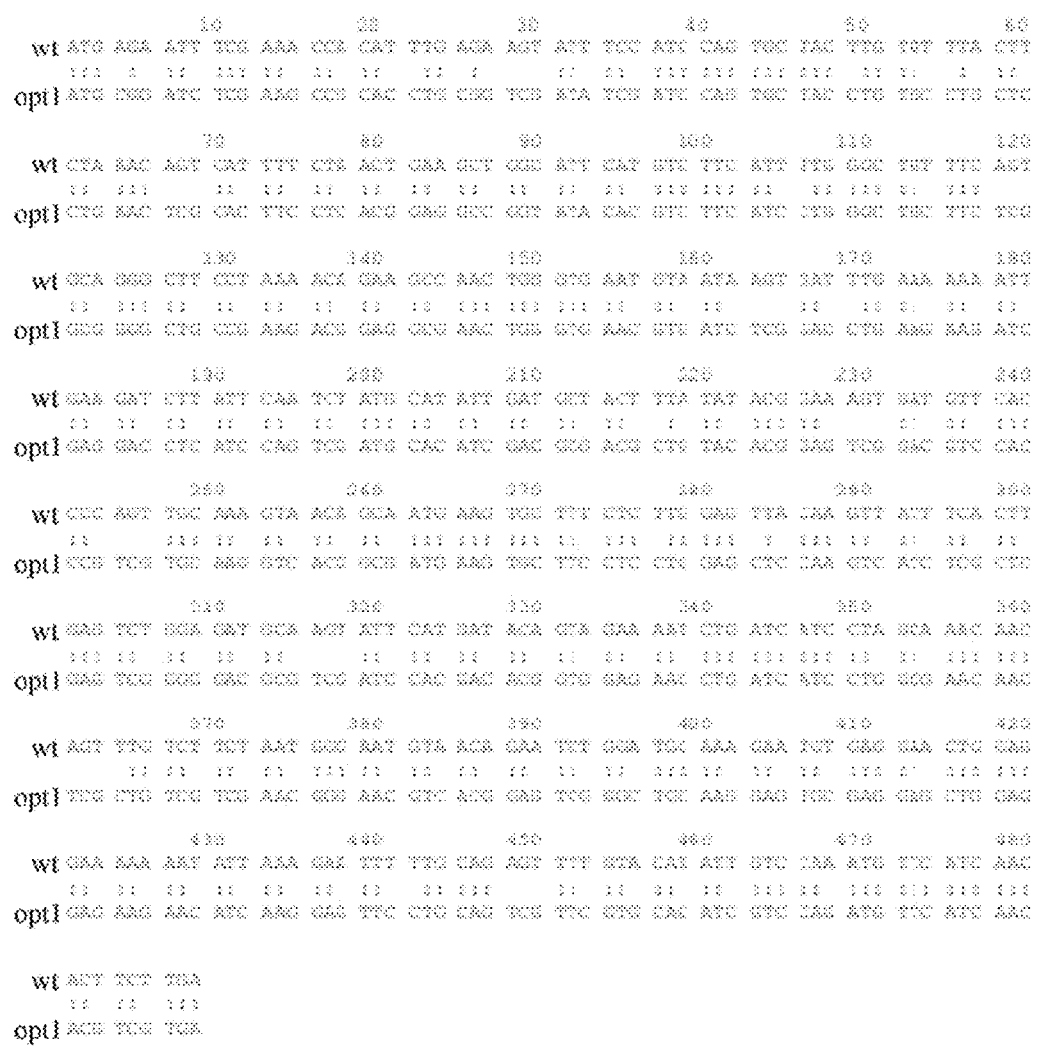

FIG. 3 illustrates a comparison of human wild-type IL-15 (SEQ ID NO:1) and improved IL-15opt1 (opt) (SEQ ID NO:3) nucleotide sequences. The sequences share 70.7% sequence identity.

FIG. 4 illustrates a comparison of the nucleotide changes between wild-type human IL-15 (top; SEQ ID NO:1) and improved human IL-15opt1 (bottom; SEQ ID NO:3) nucleotide sequences. The improved human IL-15 sequence was changed at 121 of 162 total codons (75%). Forty-one (41)

codons were left unchanged in comparison to the wild-type human IL-15 nucleotide sequence. The boxed codons indicate changes to "more preferred" codons according to the classification of Seed (U.S. Pat. No. 5,786,464) (62 codons). The underlined codons indicate codons changed to "less preferred" codons according to the classification of Seed (10 codons), in contradiction to the method of Seed. The grey highlighted codons indicate changes to "not preferred" codons (49 codons), also in contradiction to the method of Seed.

Figure 5:
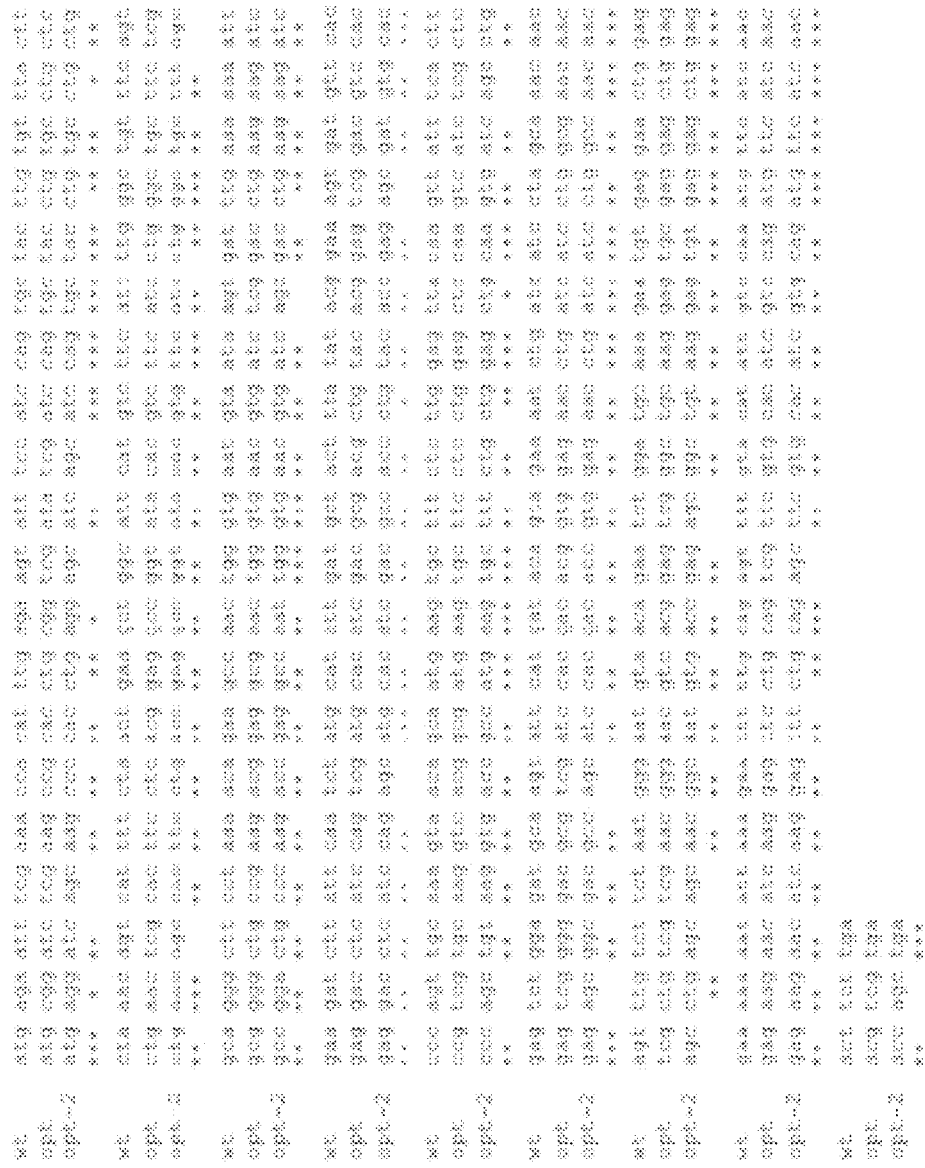

FIG. 5 illustrates a sequence alignment of the nucleic acid sequences of wild-type IL-15 (wt) (SEQ ID NO:1), IL-15opt1 (opt) (SEQ ID NO:3), and IL-15opt2 (opt-2) (SEQ ID NO:4). Wild-type IL-15 has 162 total codons. In IL-15opt1, 121 of 162 codons are changed. In IL-15opt2, 122 of 162 codons are changed.

Figure 6:
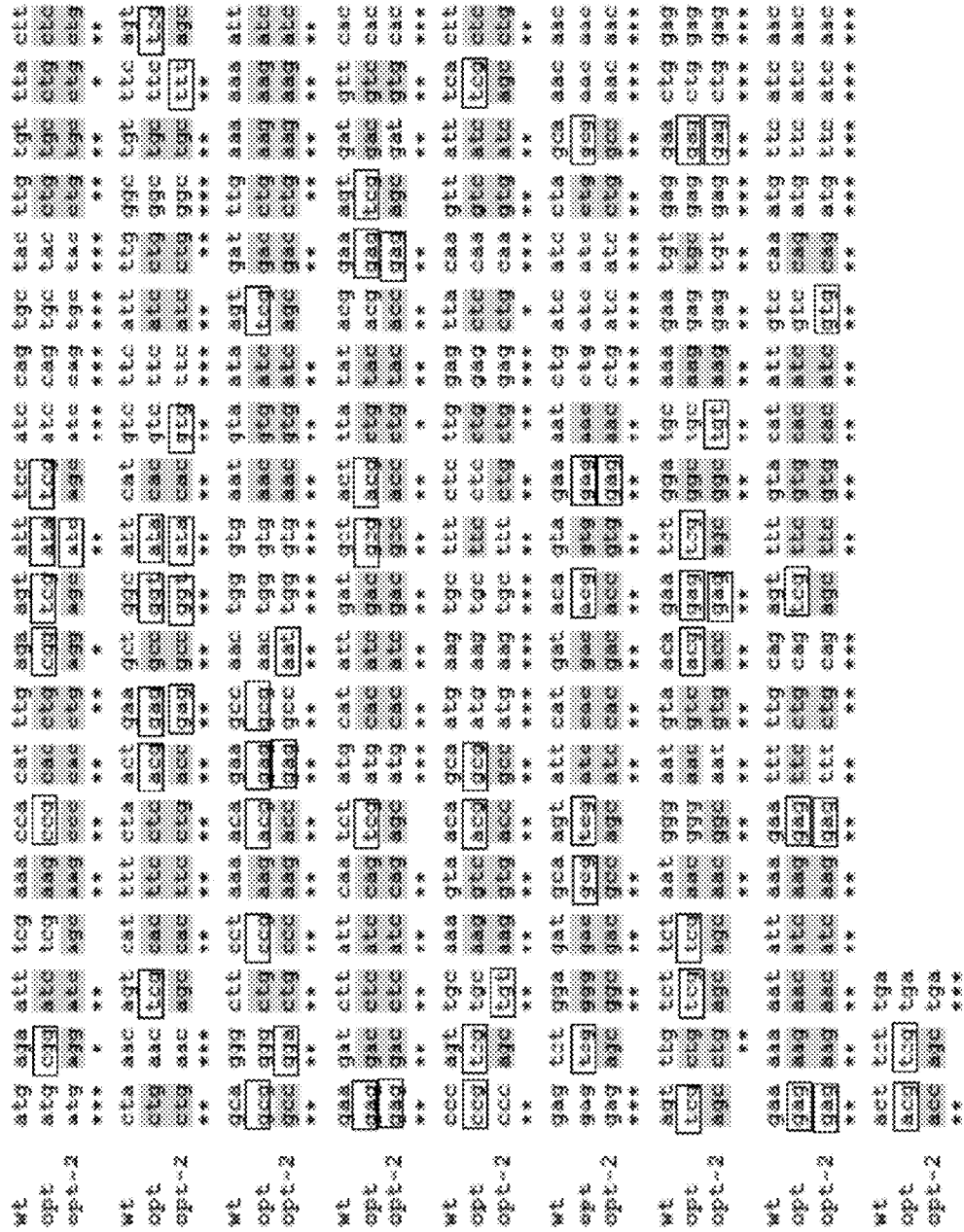

FIG. 6 illustrates a sequence alignment of the nucleic acid sequences of wild-type IL-15 (wt; SEQ ID NO:1), IL-15opt1 (opt; SEQ ID NO:3), and IL-15opt2 (opt-2; SEQ ID NO:4). Improvement of the coding sequences includes nucleotide changes that use "preferred" codons or "less preferred" codons, as defined in U.S. Pat. No. 5,786,464. IL-15opt1 has 72 preferred/less preferred codons, and IL-15opt2 has 103 preferred/less preferred codons. In addition, improvements of the IL-15 coding sequences include nucleotide changes that are in contradiction to the method defined in U.S. Pat. No. 5,786,464.

Figure 7:
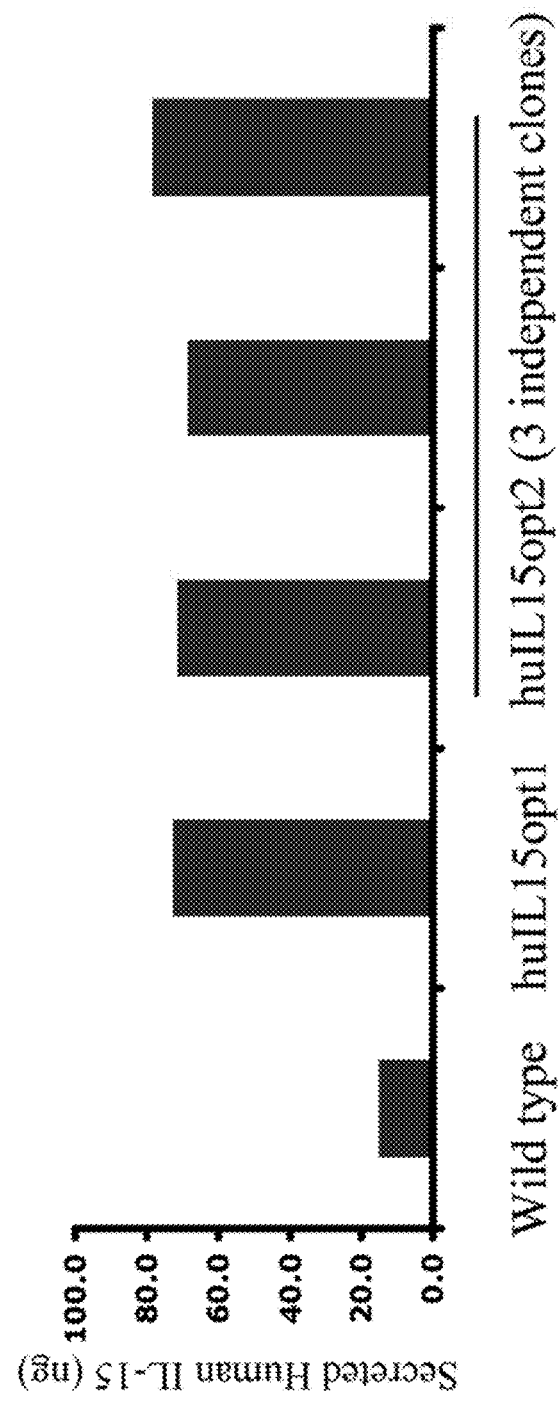

FIG. 7 illustrates that plasmids having improved human IL-15 coding sequences express increased level of human IL-15 protein in transfected mammalian cells. Depicted is a typical experiment showing a 5-fold increase using either the IL-15opt1 or IL-15opt2 nucleic acid sequences. Over an average of 7 experiments, a mean increase of 8-fold in human IL-15 protein production was achieved in comparison to expression from the wild-type human IL-15 sequence. There is no difference in IL-15 protein production between IL-15opt1 and IL-15opt2. This underscores our conclusions that it is not codon usage but rather changes of the RNA sequence that lead to improved gene expression.

Figure 8:
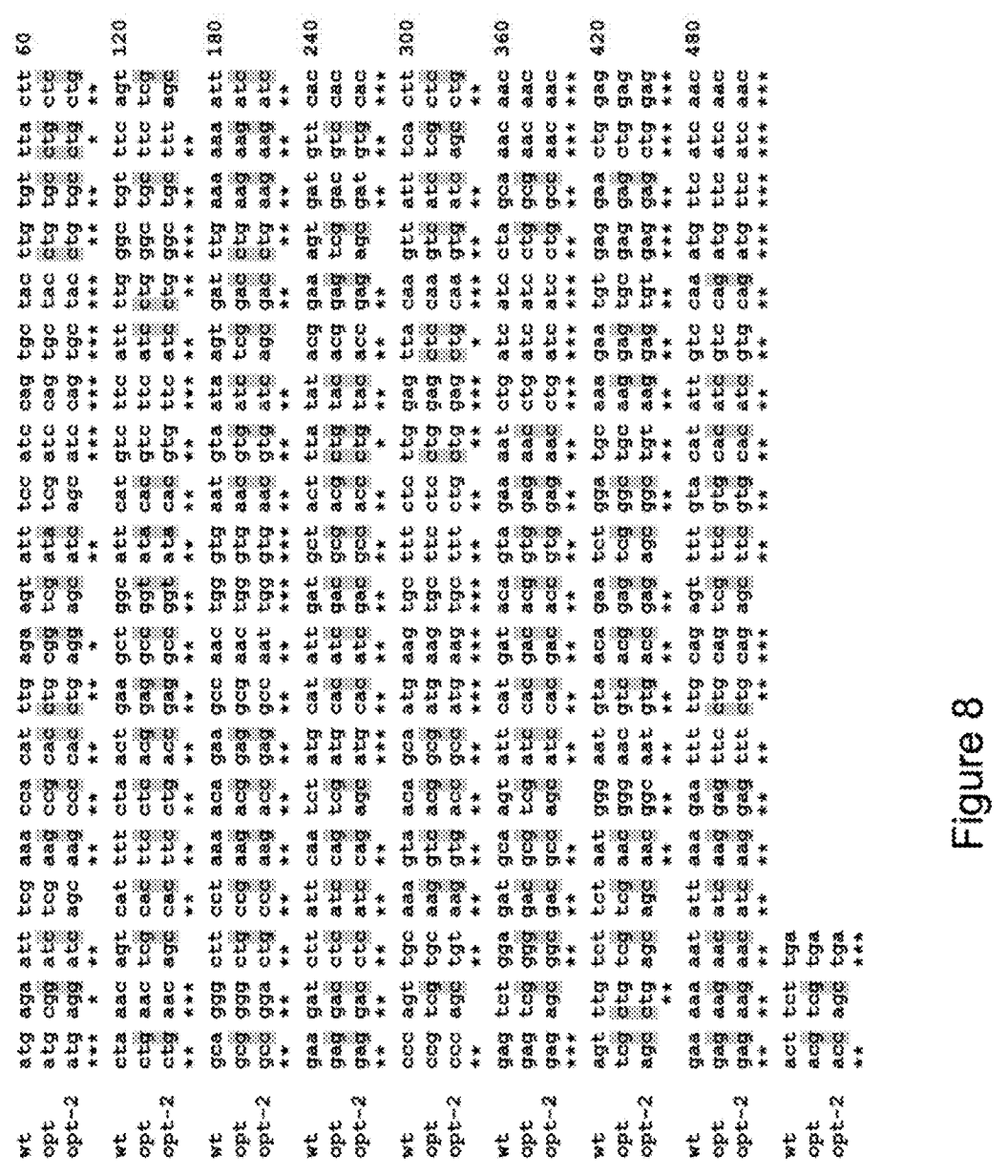

FIG. 8 illustrates the common positions of nucleotide changes (highlighted) in IL-15opt1 (SEQ ID NO:3) and IL-15opt2 (SEQ ID NO:4) sequences compared to wild type human IL-15 (SEQ ID NO:1). Changes at the positions of the indicated 115 nucleotides (highlighted) are sufficient for improved mRNA and protein expression of human IL-15 (an approximately 8-fold increase in comparison to wild-type human IL-15).

Figure 9:
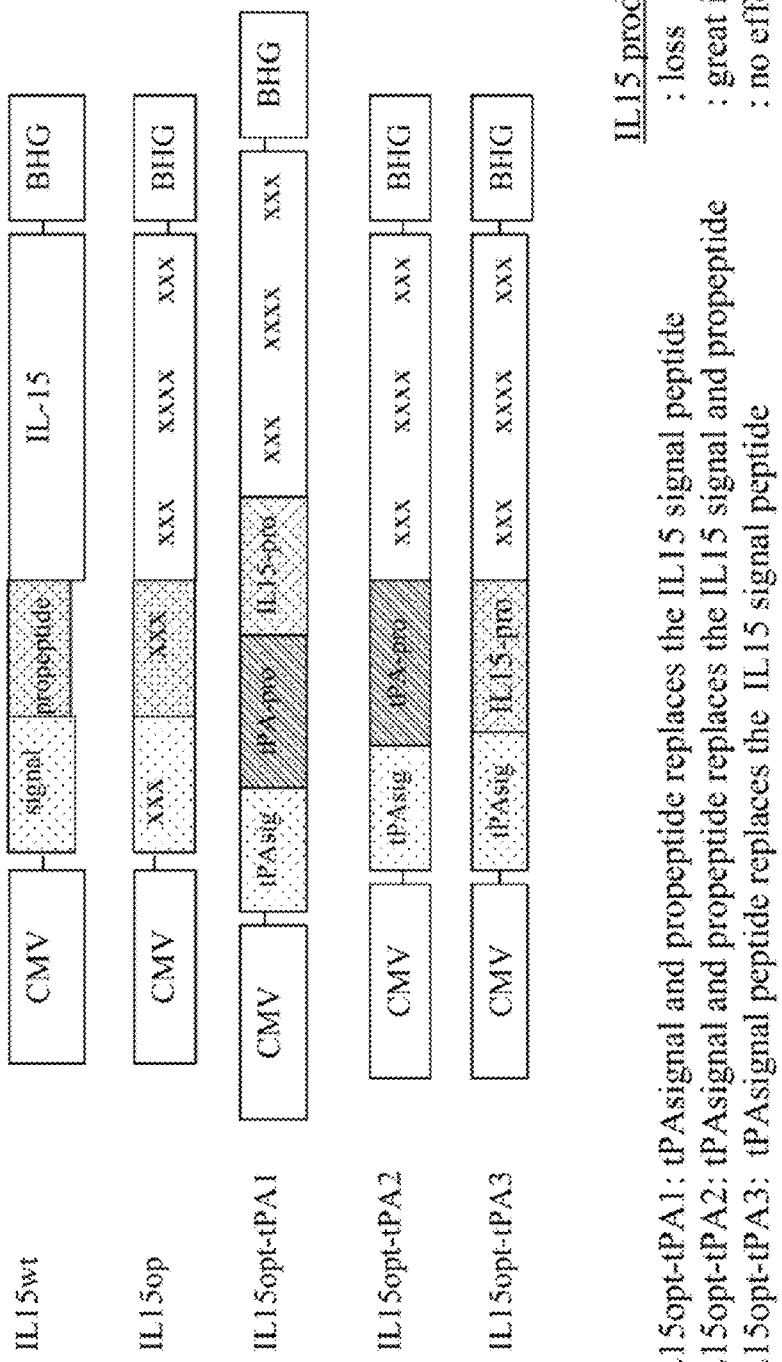

FIG. 9 illustrates that modification of signal and/or propeptide of human IL-15 leads to an increased extracellular accumulation of IL-15.

Figure 10:
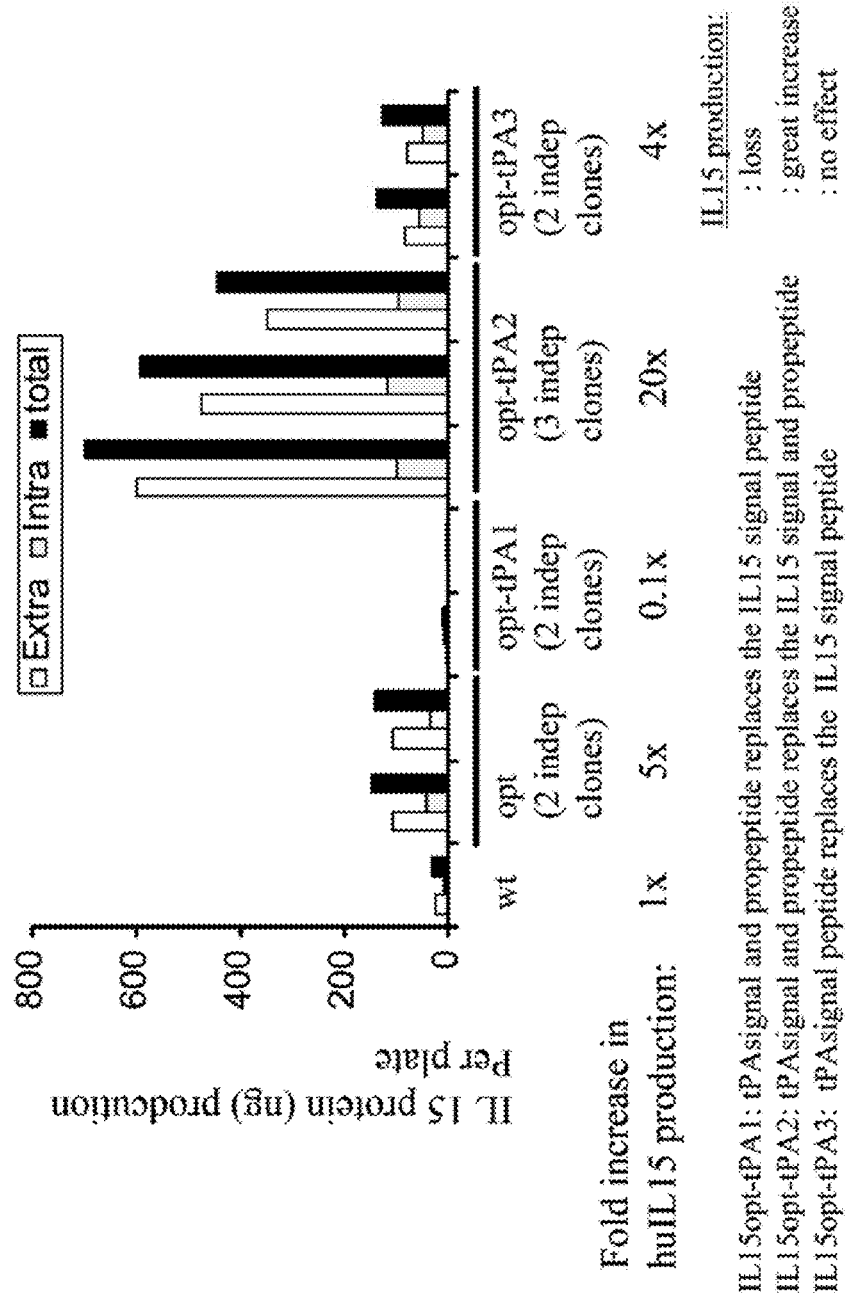

FIG. 10 illustrates that improved IL-15 coding sequences fused to the signal peptide and propeptide of tissue plasminogen activator (tPA) greatly improves IL-15 protein production in mammalian cells. Expressing IL-15 from IL-15opt-tPA2, which contains tissue plasminogen activator signal peptide and propeptide sequences, resulted in an additional 2.5 average fold increase of IL-15 protein production in mammalian cells (mean of 4 experiments using 1-3 independent clones) in comparison to improved IL-15 (opt). Other variants with differentially swapped domains, which either had the tPA signal peptide only (IL-15opt-tPA1) or a combination of the tPA signal peptide with the IL-15 propeptide (IL-15opt-tPA3) resulted in decreased IL-15 protein production or no improvement.

Figure 11:
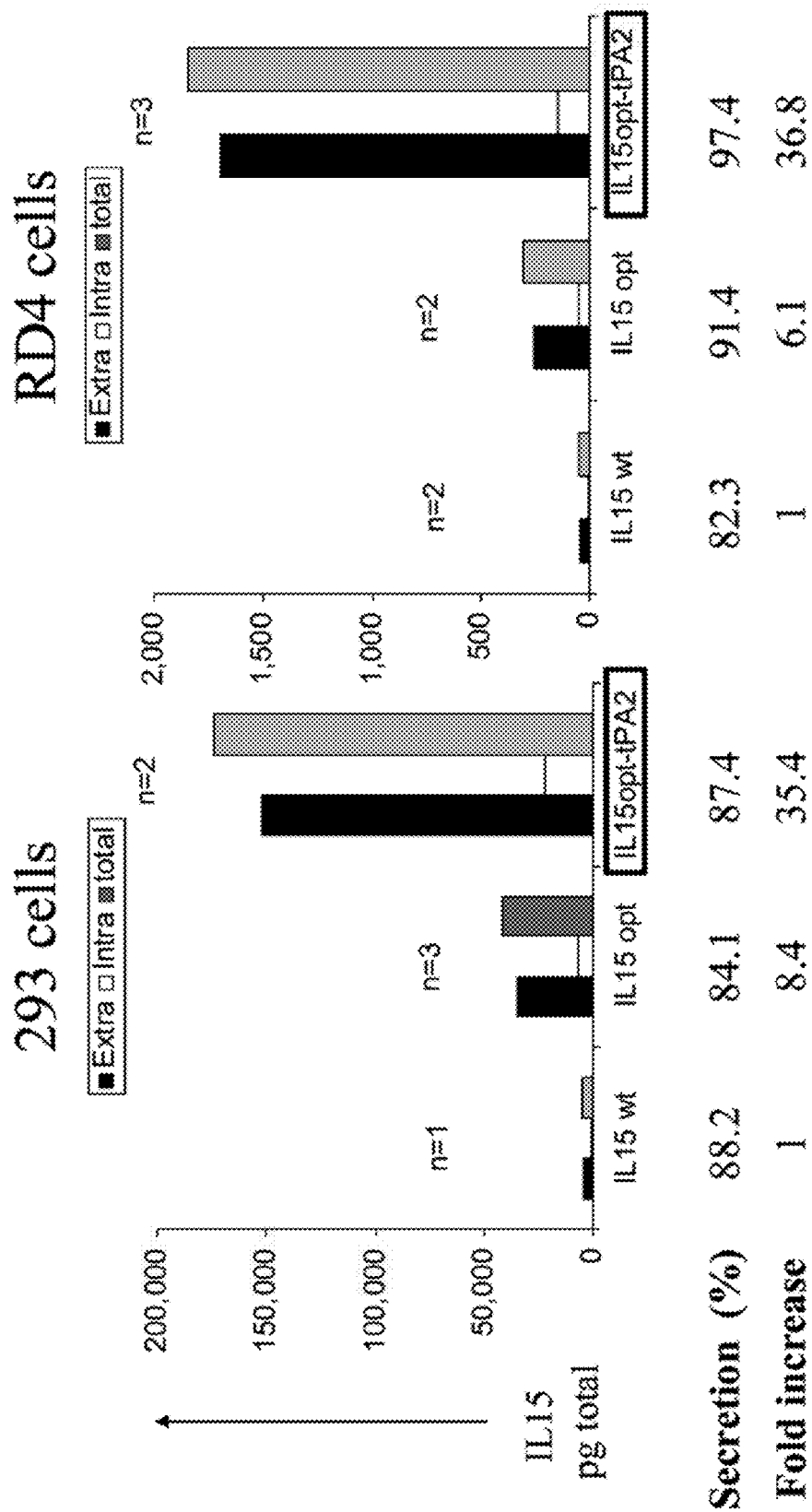

FIG. 11 illustrates the improved expression of human IL-15-tPA2, in comparison to wild-type human IL-15 (IL-15 wt) and improved IL-15 (IL-15opt), from transfected human 293 and RD4 cells.

Figure 12:
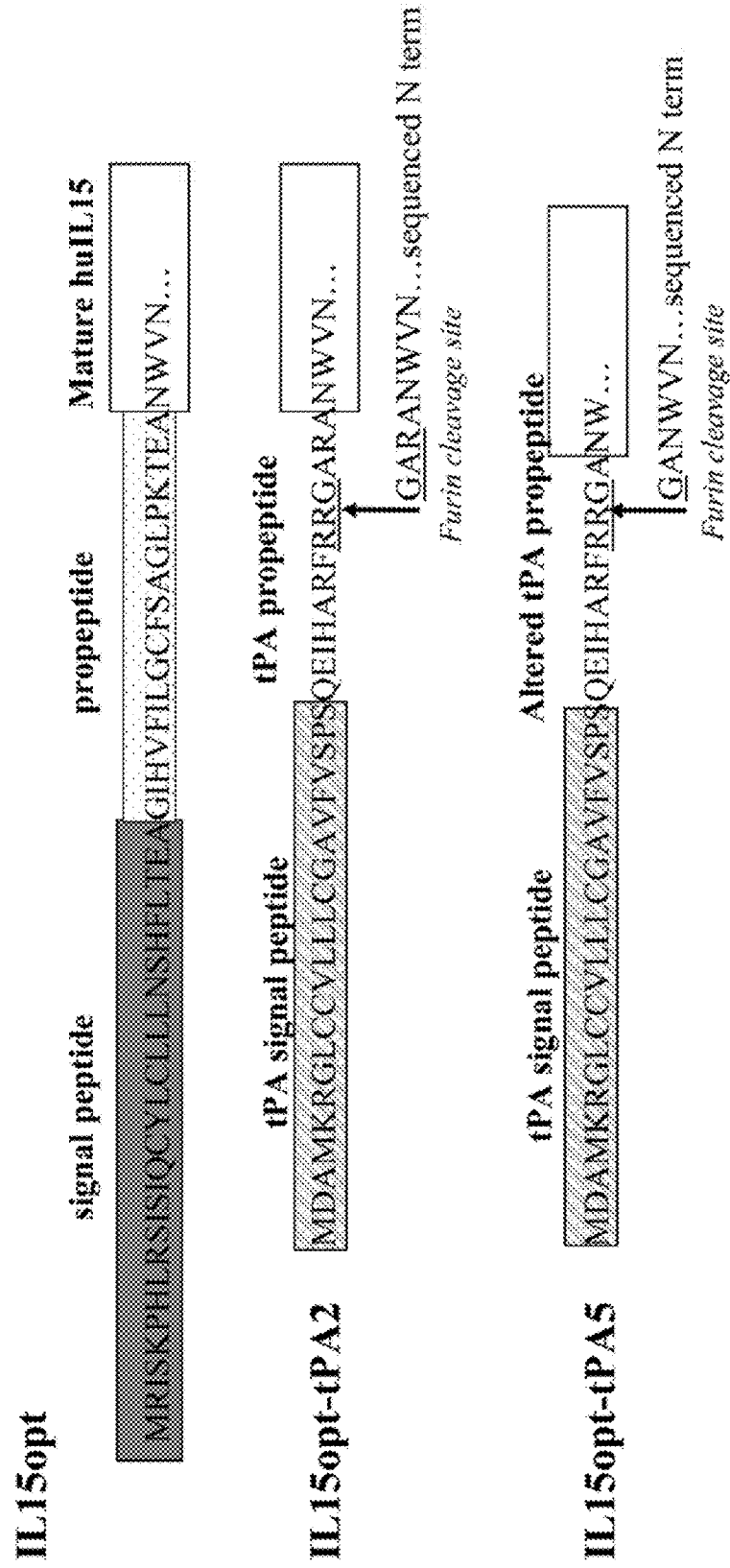

FIG. 12 illustrates alteration of the tPA signal peptide-IL-15 junction to produce the proper N-terminus for IL-15. IL-15opt-tPA2 sequence (SEQ ID NO:37) has a furin cleavage site and 4 extra amino acids (GARA; SEQ ID NO:41) at the N-terminus (SEQ ID NO:38) in comparison to wild-type human IL-15 (SEQ ID NO:5 and SEQ ID NO:6). IL-15opt-tPA5 sequence (SEQ ID NO:39) has a furin cleavage site sequence (R-X-(K/R)-R) and 2 additional amino acids (GA) immediately adjacent to the N terminus (SEQ ID NO:40) of the mature IL-15 (SEQ ID NO:7 and SEQ ID NO:8). IL15opt=SEQ ID NO:36. The resulting IL-15 proteins were sequenced from the supernatant of transfected 293 cells and were shown to have the indicated extra amino acids immediately adjacent to the N terminus of mature IL-15.

Figure 13:
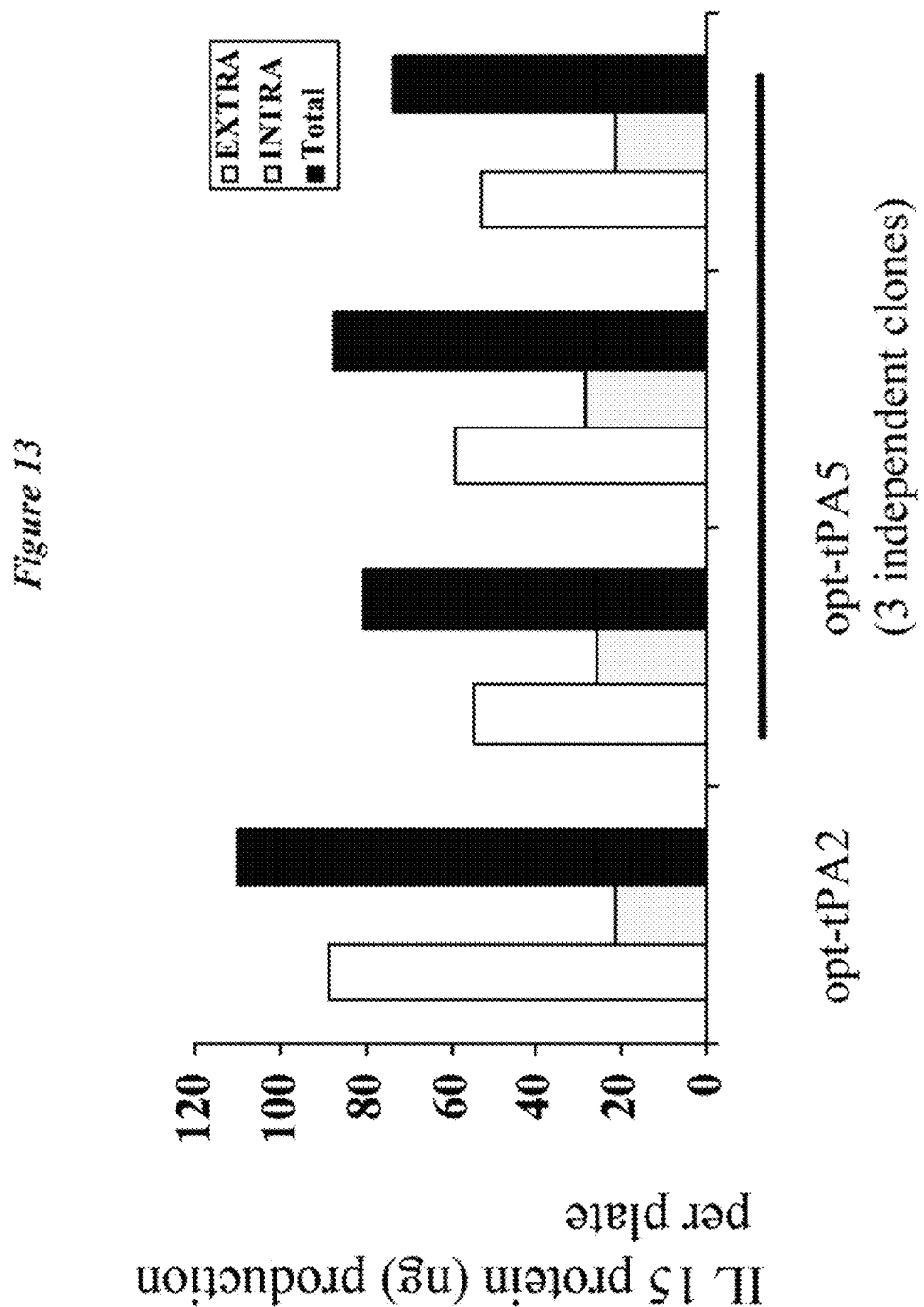

FIG. 13 illustrates similar production of IL-15 protein from modified tPA fusion proteins, IL-15opt-tPA2 (opt-tPA2) and IL-15opt-tPA5 (opt-tPA5).

FIG. 14 illustrates that human IL-15 (h-IL15) (SEQ ID NO:2) and Rhesus monkey (*Macaca mulatta*) IL-15 (rh-IL15) (SEQ ID NO:15) proteins share 96% identity, differing by 6 amino acids. Site-directed mutagenesis was used to introduce the indicated 11 nucleotide changes into the human IL-15opt1 coding nucleotide sequence, generating the Rhesus IL-15opt coding nucleotide sequence.

FIG. 15 illustrates a comparison of the nucleotide sequences of human IL-15opt1 (huIL-15opt) (SEQ ID NO:3) and Rhesus IL-15opt (rhIL-15opt) (SEQ ID NO:16). Eleven (11) nucleotide changes were introduced into the 489 nucleotide coding region of human IL-15opt1.

Figure 16:
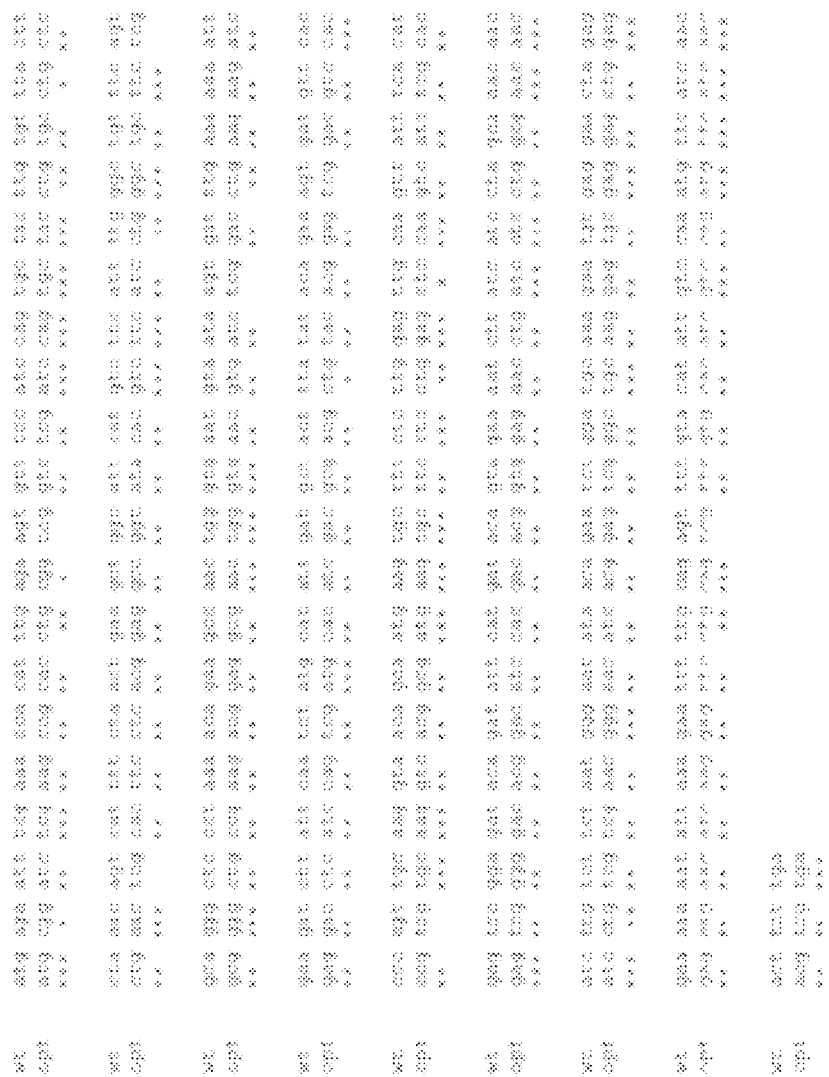

FIG. 16 illustrates a comparison of Rhesus wild-type IL-15 (wt) (SEQ ID NO:14) and Rhesus improved IL-15 (opt) (SEQ ID NO:16) nucleotide sequences. The nucleotide sequences share 71.3% identity.

Figure 17:
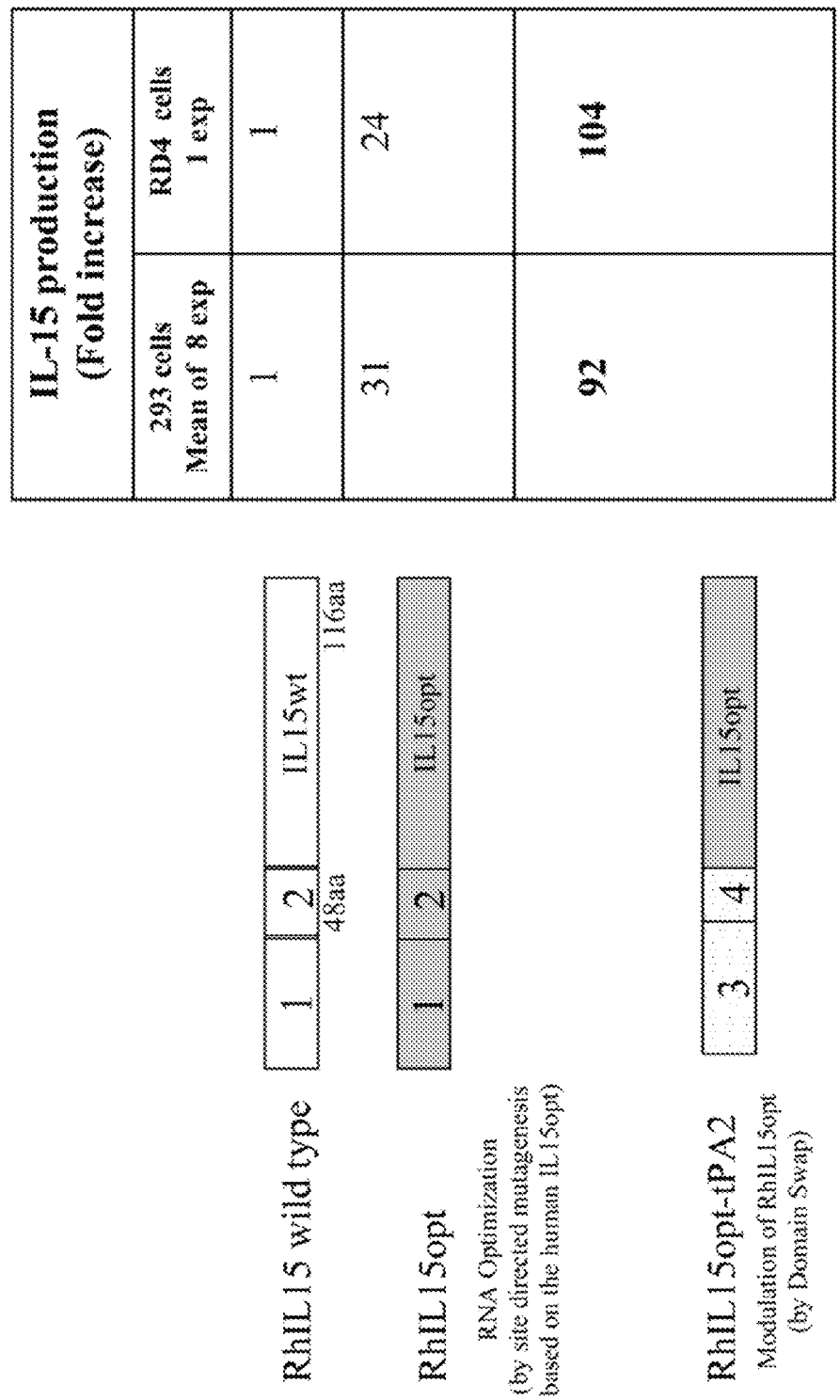

FIG. 17 illustrates that improvement of the Rhesus IL-15 coding sequence resulted in an approximately 30-fold increase in Rhesus IL-15 protein production in mammalian cells. Substitution of the IL-15 signal peptide and propeptide sequences with tPA signal peptide and propeptide sequences resulted in a further 3-fold improvement, indicating synergistic effects of the two approaches.

Figure 18:
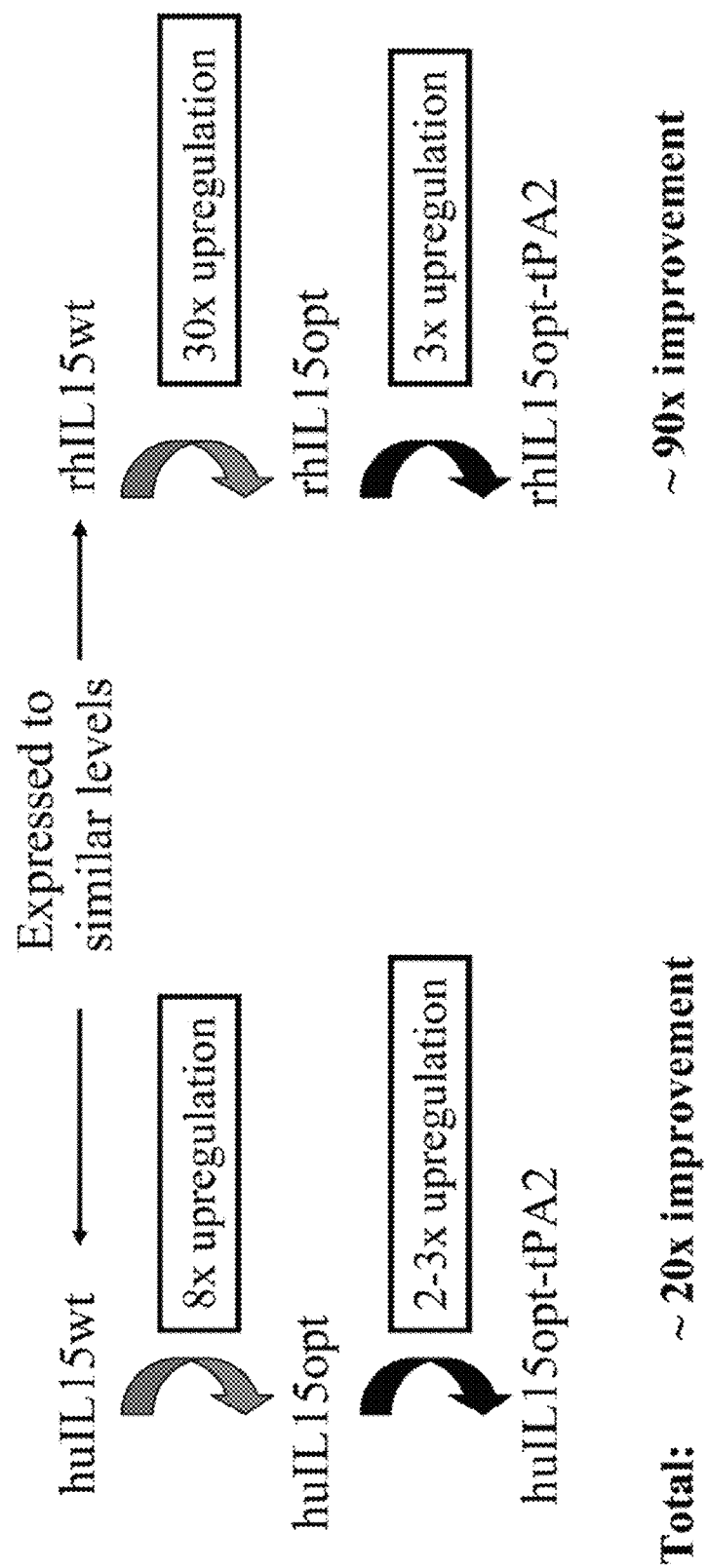

FIG. 18 illustrates that improving IL-15 coding sequences led to great increases of both human and Rhesus IL-15 protein production. The final increase in expression was approximately 20-fold for human and a 90-100 fold increase for Rhesus IL-15. In both human and Rhesus IL-15 vectors, the substitution of the IL-15 signal peptide and propeptide with tPA signal peptide and propeptide sequences led to an additional approximately 3-fold increase in IL-15 protein production from mammalian cells.

Figure 19:
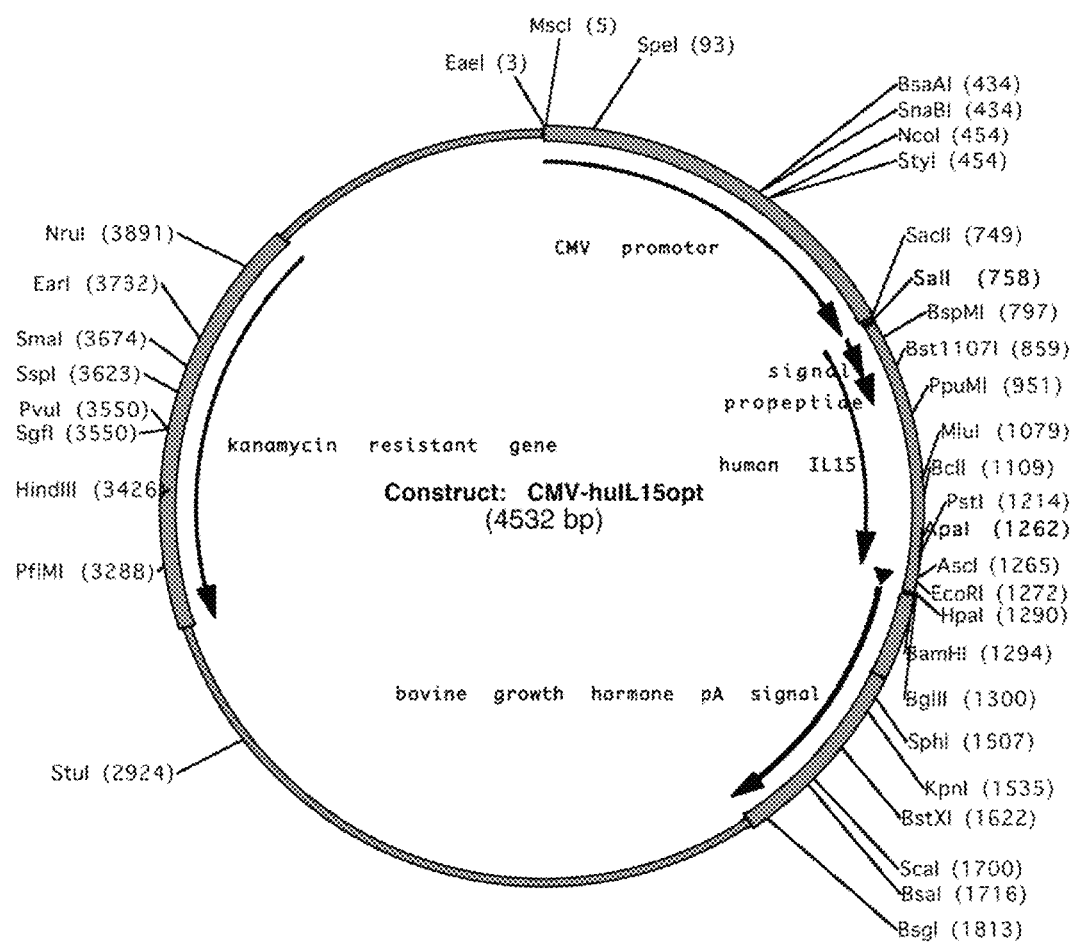

FIG. 19 illustrates a schematic representation of an expression vector for expressing optimized human IL-15 from a cytomegalovirus promoter (CMVhuIL-15opt).

Figure 20:
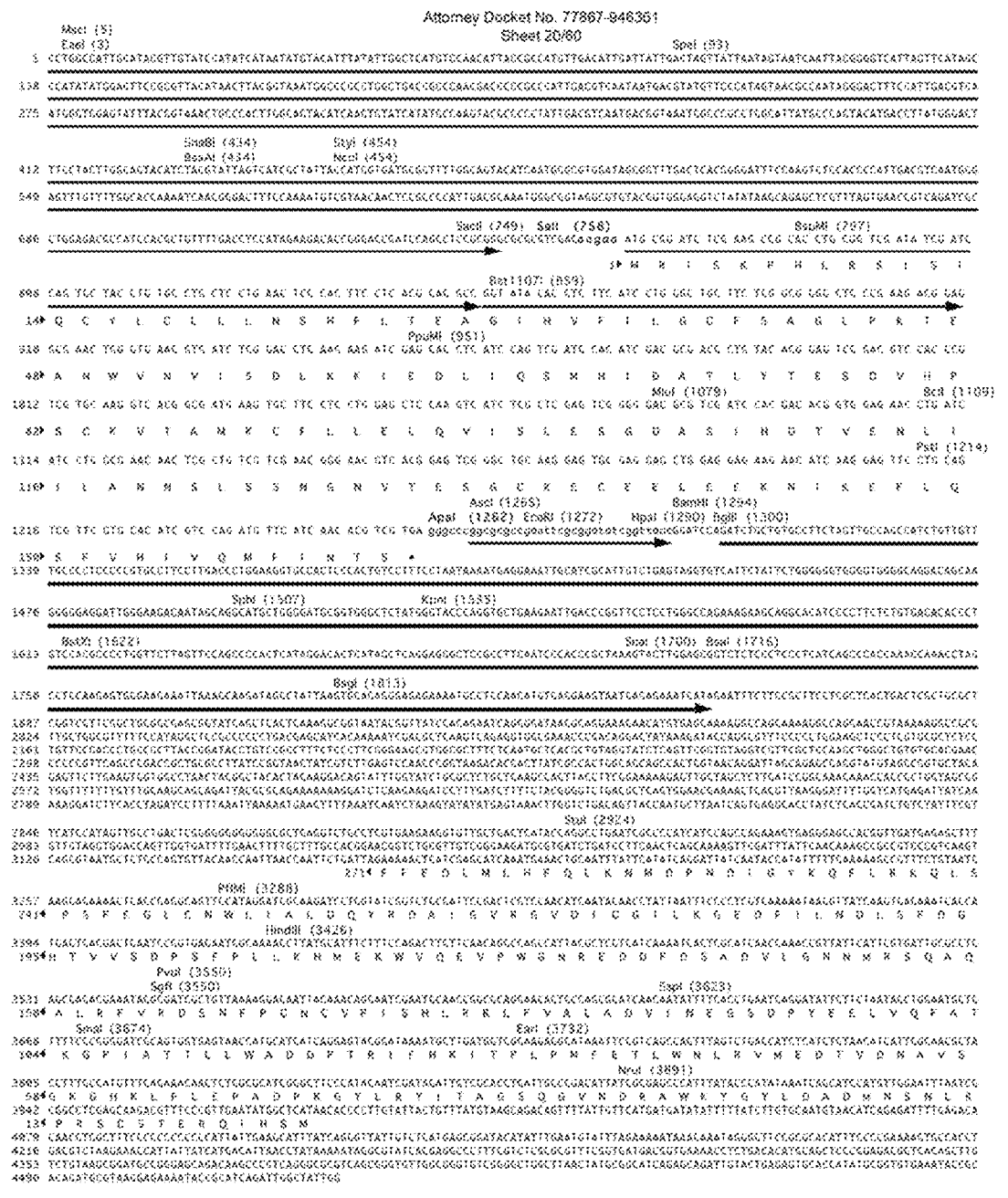

FIG. 20 illustrates a sequence map of expression vector CMVhuIL-15(opt1) (SEQ ID NO:13). See, SEQ ID NO:21 for the corresponding expression vector for expressing optimized Rhesus IL-15 from a cytomegalovirus promoter (CMVrhIL-15opt). Human IL-15=SEQ ID NO:2; kanamycin marker=SEQ ID NO:42.

Figure 21:
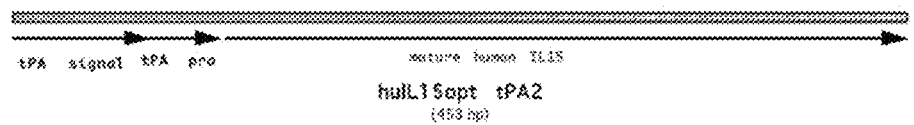

FIG. 21 illustrates a schematic representation of human optimized IL-15 with the signal peptide and propeptide sequences from tissue plasminogen activator protein (huIL-15opt-tPA2).

Figure 22:
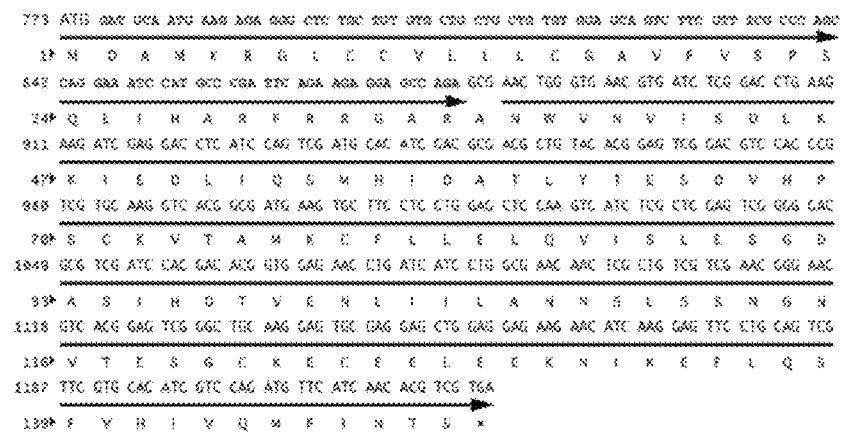

FIG. 22 illustrates the nucleic acid sequence (SEQ ID NO:9) and amino acid sequence (SEQ ID NO:10) of huIL-15opt1-tPA2. See, SEQ ID NO:17 and SEQ ID NO:18 for the corresponding nucleic acid and amino acid sequences of Rhesus optimized IL-15 with the signal peptide and propeptide sequences from tissue plasminogen activator protein (rhIL-15opt-tPA2).

Figure 23:
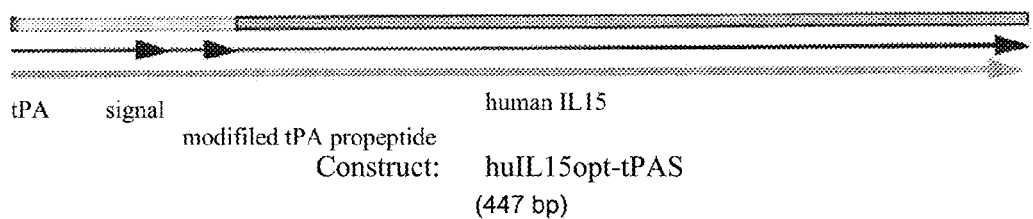

FIG. 23 illustrates a schematic representation of human optimized IL-15 with modified signal peptide and propeptide sequences from tissue plasminogen activator protein (huIL-15opt-tPA5).

Figure 24:
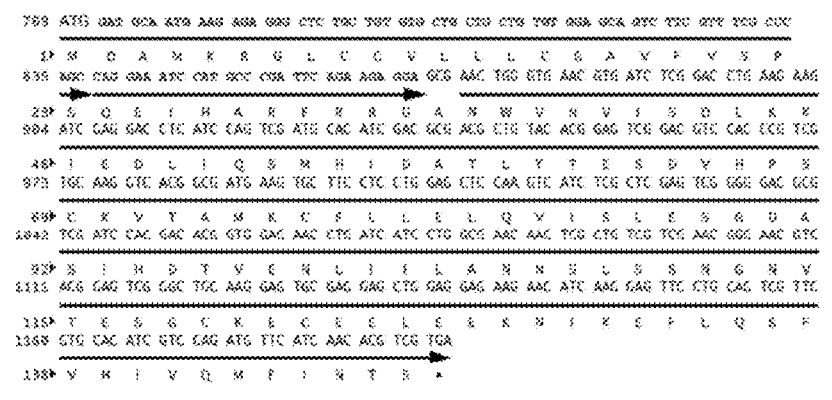

FIG. 24 illustrates the nucleic acid sequence (SEQ ID NO:11) and amino acid sequence (SEQ ID NO:12) of huIL-15opt1-tPA5. See, SEQ ID NO:19 and SEQ ID NO:20 for the corresponding nucleic acid and amino acid sequences of Rhesus optimized IL-15 with the signal peptide and propeptide sequences from tissue plasminogen activator protein (rhIL-15opt-tPA2).

Figure 25:
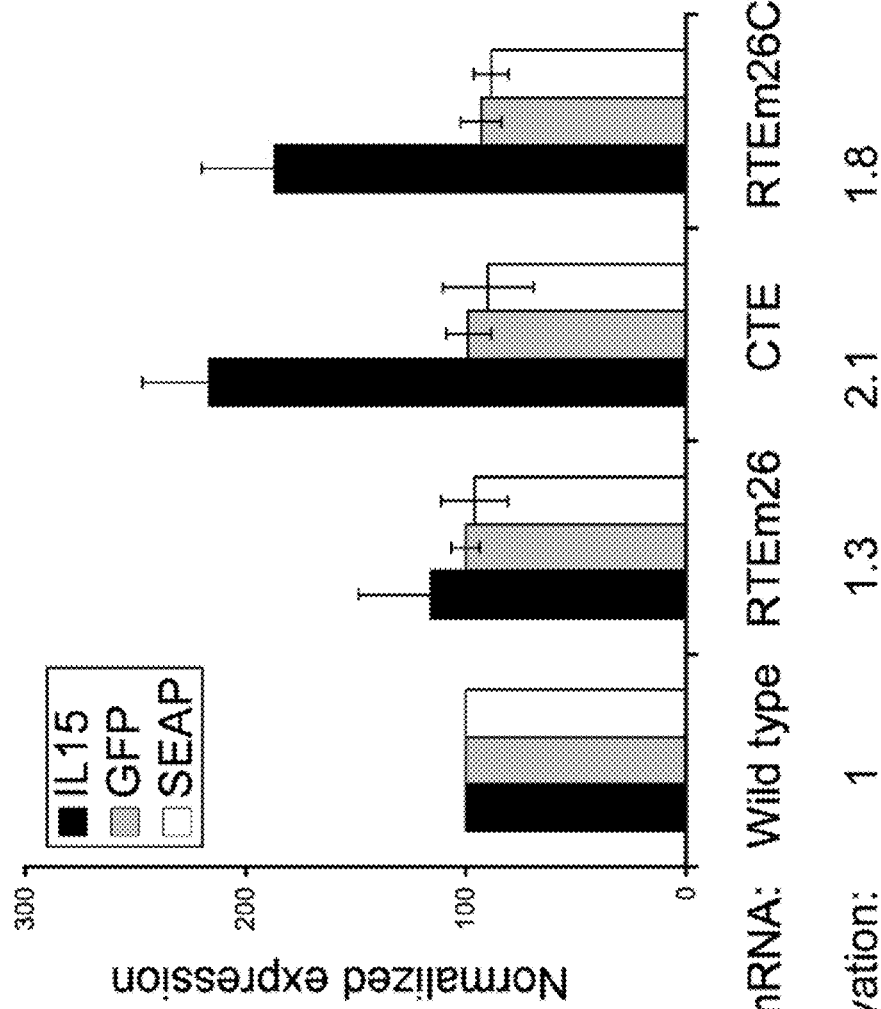

FIG. 25 illustrates that fusion of a wild-type IL-15 sequence to an RNA export element, including CTE or RTEm26CTE resulted in an approximately 2-fold increase in IL-15 protein production from mammalian cells.

Figure 26:
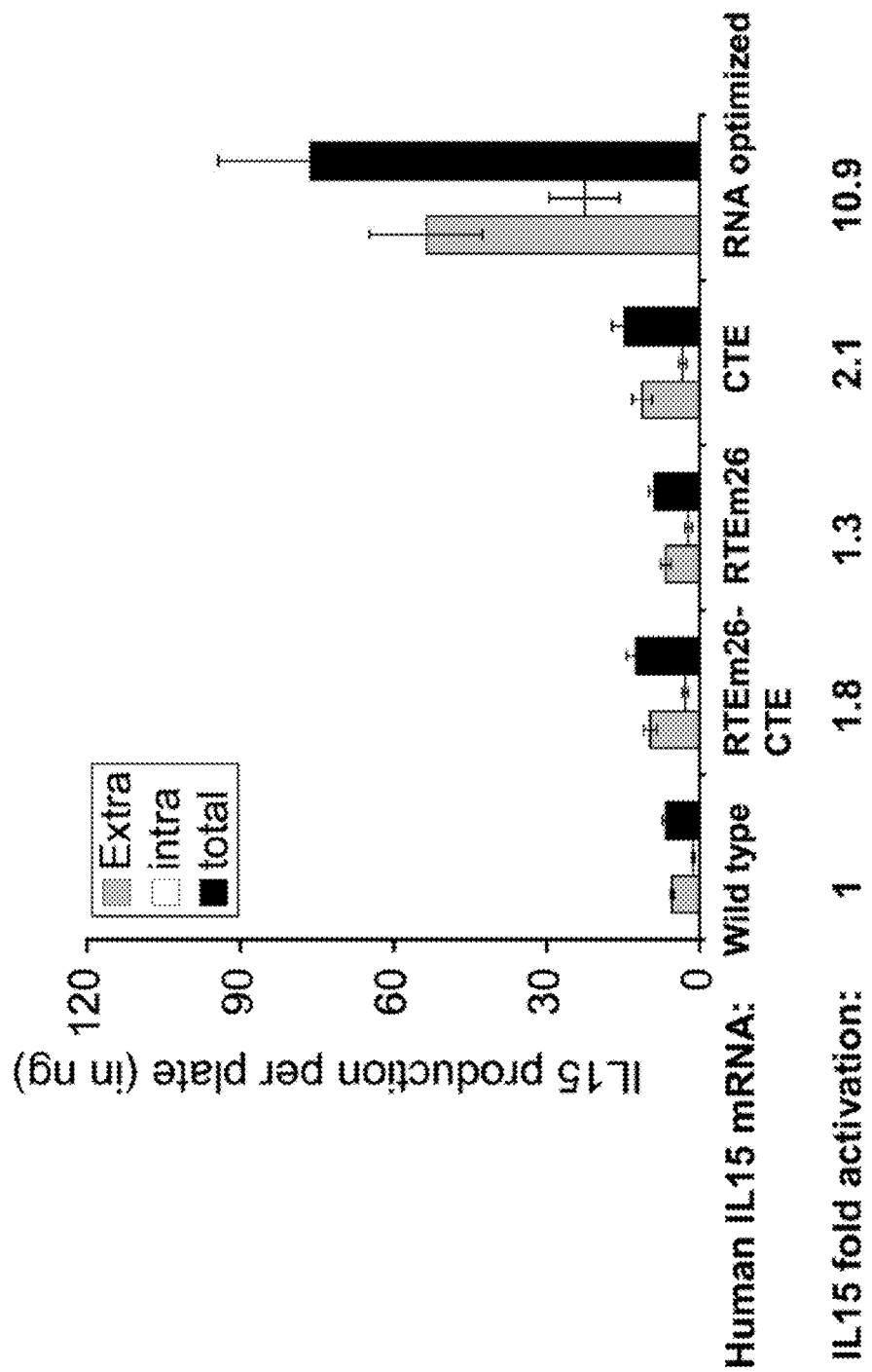

FIG. 26 illustrates that improving the human IL-15 coding sequence further increases IL-15 protein production from human 293 cells 5-fold as compared to wild-type human IL-15 operably linked to RNA export elements CTE or RTEm26CTE and 10-fold as compared to wild-type human IL-15.

Figure 27:
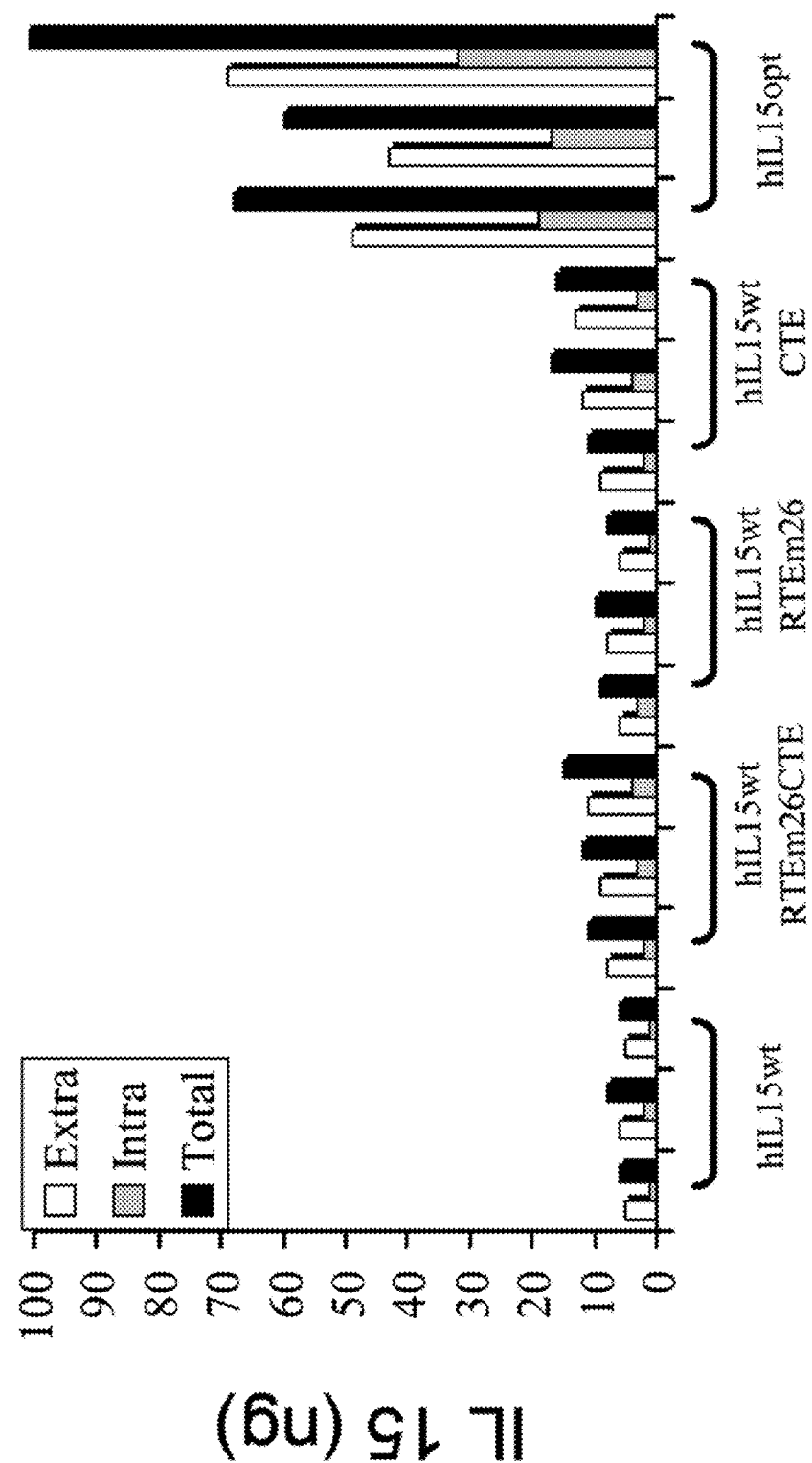

FIG. 27 illustrates that improving the human IL-15 coding sequence further increases IL-15 protein production from 293 cells at least 2-fold in comparison to wild-type human IL-15 produced from RNA export elements CTE or RTEm26CTE.

FIG. 28 illustrates changes in the tPA-IL-15 fusion as exemplified in IL-15opt-tPA6 and IL-15opt-tPA7. IL-15opt-tPA6 contains a furin cleavage site sequence (R-X-(K/R)-R) and the 3 additional amino acids (GAR) immediately adjacent to the N terminus of the mature IL-15 (see, SEQ ID NOs:24 and 25). IL-15opt-tPA7 contains a furin cleavage site sequence (R-X-(K/R)-R) and one additional amino acid (G) immediately adjacent to the N terminus of the mature IL-15 (see, SEQ ID NOs:26 and 27). The resulting IL-15 proteins were sequenced from the supernatant of transfected 293 cells and were shown to have the indicated additional amino acids immediately adjacent to the N terminus of mature IL-15. Peptides=SEQ ID NOS:43-46.

Figure 29:
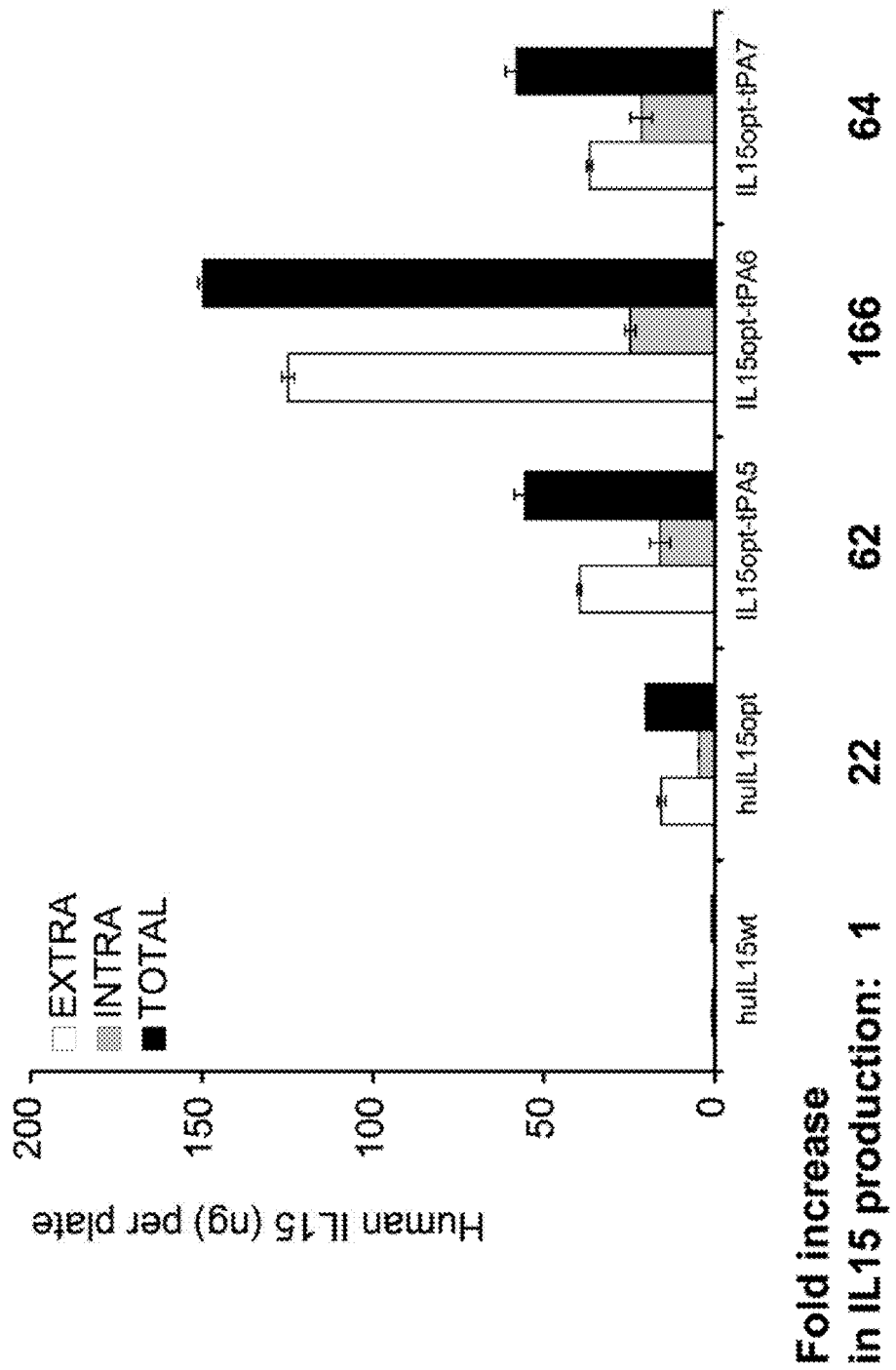

FIG. 29 illustrates that improved human IL-15 sequences human IL-15opt-tPA6 and human IL-15opt-tPA7 show similar increased levels of IL-15 production in comparison to human IL-15opt-tPA2 and human IL-15opt-tPA5. Protein levels produced from the different improved sequences were measured from transfected human 293 cells. The produced IL-15 proteins differ at the N terminus by either having GARA, GAR, GA or G immediately adjacent to the N terminus. Different plasmids expressing the tPA signal fused to N terminus of the mature IL-15 show similar levels of improved IL-15 production.

Figure 30:
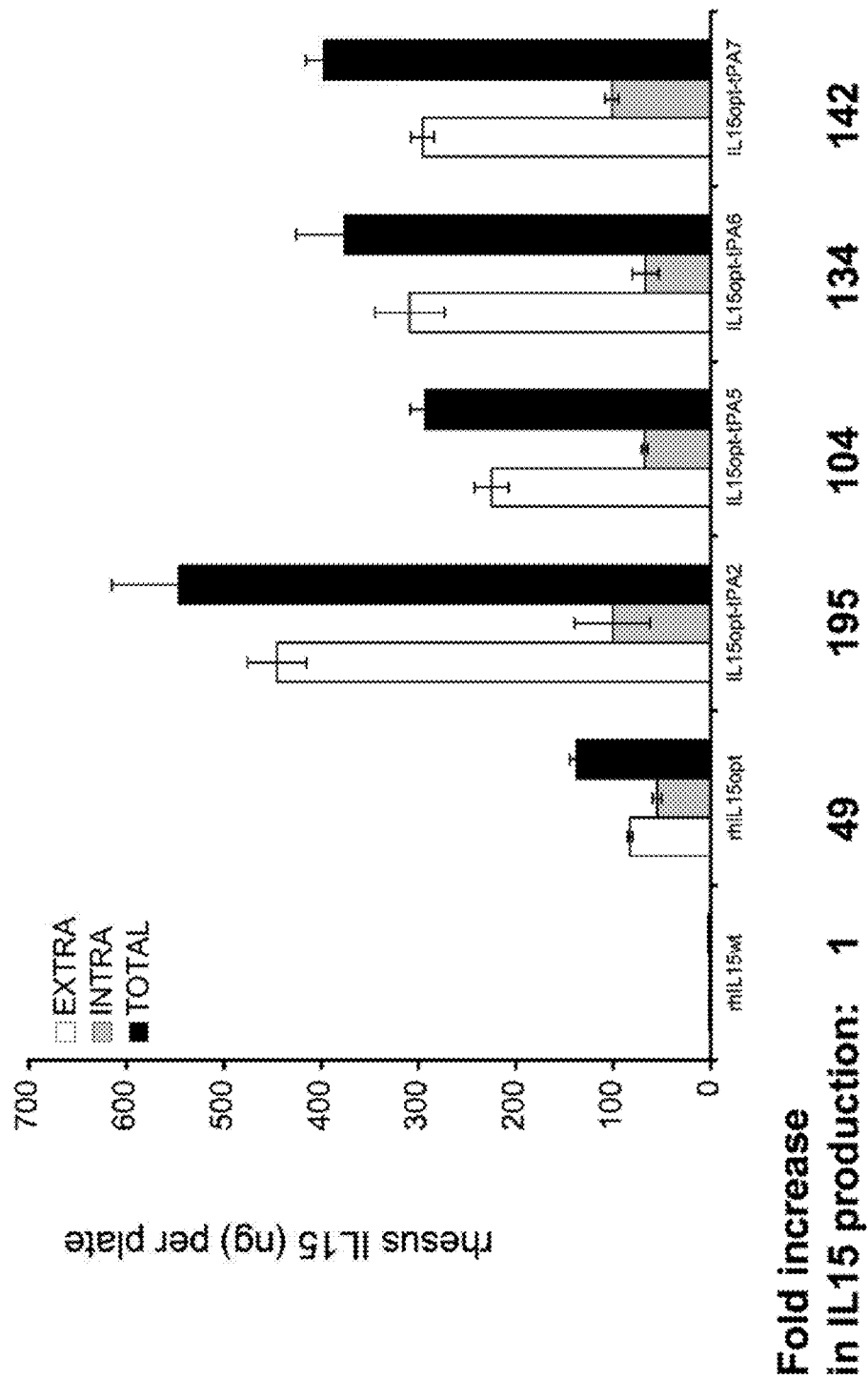

FIG. 30 illustrates that improved rhesus IL-15 sequences rhesus IL-15opt-tPA6 and rhesus IL-15opt-tPA7 show similar increased levels of IL-15 production in comparison to rhesus IL-15opt-tPA2 and rhesus IL-15opt-tPA5. Protein levels produced from the different improved sequences were measured from transfected human 293 cells. The data are analogous to those using improved human IL-15 sequences, supra.

Figure 31:
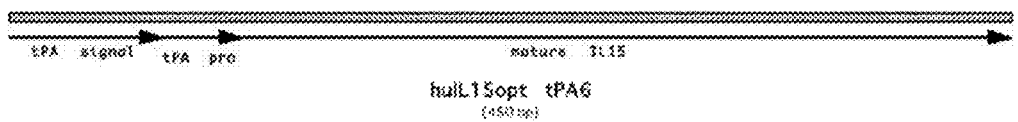

FIG. 31 illustrates a schematic of human IL-15opt-tPA6.

FIG. 32 illustrates the nucleic acid sequence (SEQ ID NO:28) and amino acid sequence (SEQ ID NO:29) of human IL-15opt1-tPA6. The nucleic acid and amino acid sequences for Rhesus IL-15opt-tPA6 are shown as SEQ ID NOs:32 and 33, respectively.

Figure 33:
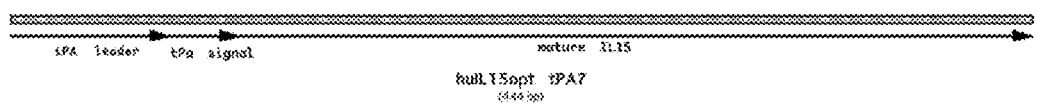

FIG. 33 illustrates a schematic of human IL-15opt-tPA7.

Figure 34:
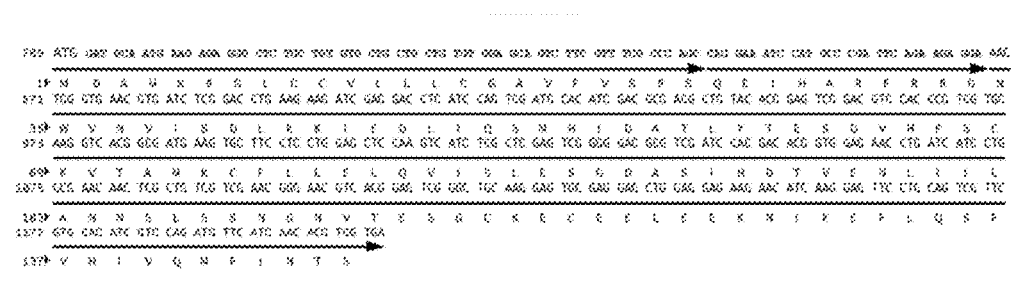

FIG. 34 illustrates the nucleic acid sequence (SEQ ID NO:30) and amino acid sequence (SEQ ID NO:31) of human IL-15opt1-tPA7. The nucleic acid and amino acid sequences for Rhesus IL-15opt-tPA7 are shown as SEQ ID NOs:34 and 35, respectively.

FIG. 35 illustrates the nucleic acid of an improved human IL-15 receptor alpha (IL15Ra) nucleic acid sequence (SEQ ID NO:47) and the encoded amino acid sequence (SEQ ID NO:48).

FIG. 36 illustrates the nucleic acid of an improved human IL15Ra nucleic acid sequence (SEQ ID NO:47) and the encoded amino acid sequence (SEQ ID NO:48).

FIG. 37 illustrates the nucleic acid of an improved human soluble IL15Ra nucleic acid sequence (SEQ ID NO:49) and the encoded amino acid sequence (SEQ ID NO:50).

Figure 38:
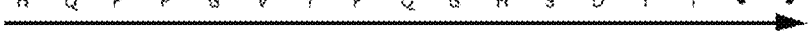

FIG. 38 illustrates the nucleic acid of an improved human soluble IL15Ra nucleic acid sequence (SEQ ID NO:49) and the encoded amino acid sequence (SEQ ID NO:50).

Figure 39:
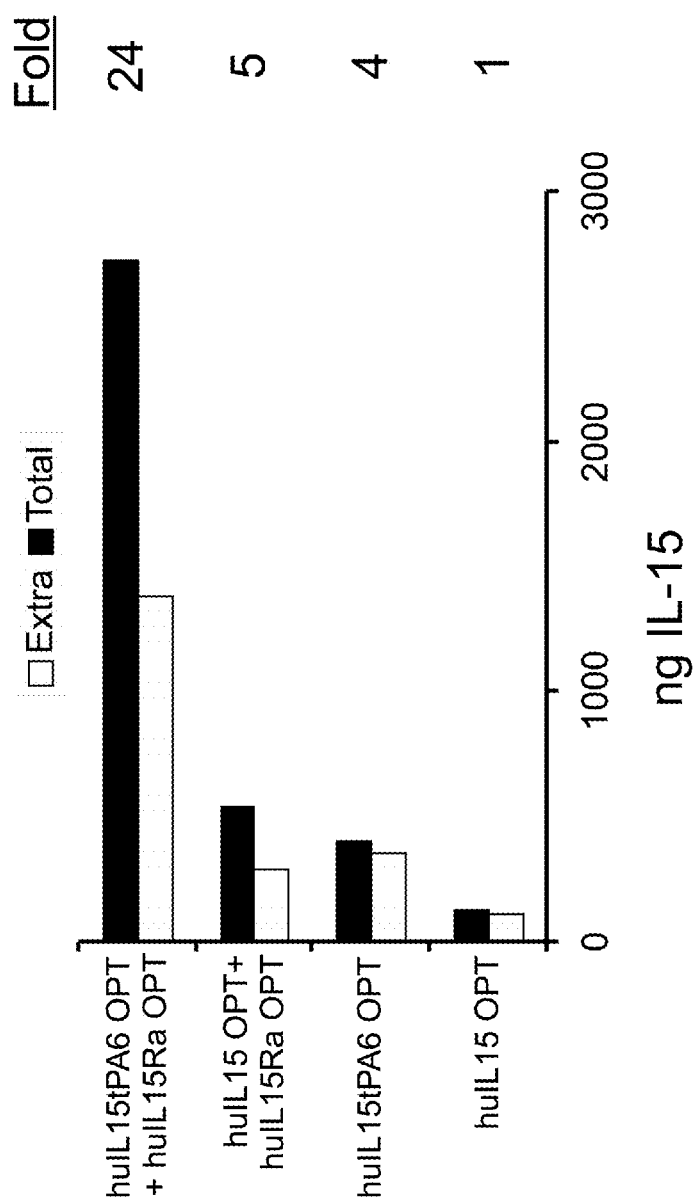

FIG. 39 illustrates that co-expression of IL-15 with IL-15 Receptor alpha improved sequences in human 293 cells in vitro using standard transfection methods led to a dramatic increase of total IL-15 levels measured. 100 ng of hIL-15 (native (plasmid AG32) or using the tPA leader (plasmid AG59)), alone or in combination with hIL15Ra (plasmid AG79) were transfected in 293 cells together 100 ng of GFP and 100 ng SEAP by the Ca—PO$_4$ co-precipitation method. After 48 hours cells were harvested and Elisa was performed using Quantikine Human IL-15, RD systems to quantify IL-15 in media (extra) and cells. Total IL-15 (extracellular and intracellular) is also indicated. Fold indicates the fold increase in IL-15.

Figure 40:
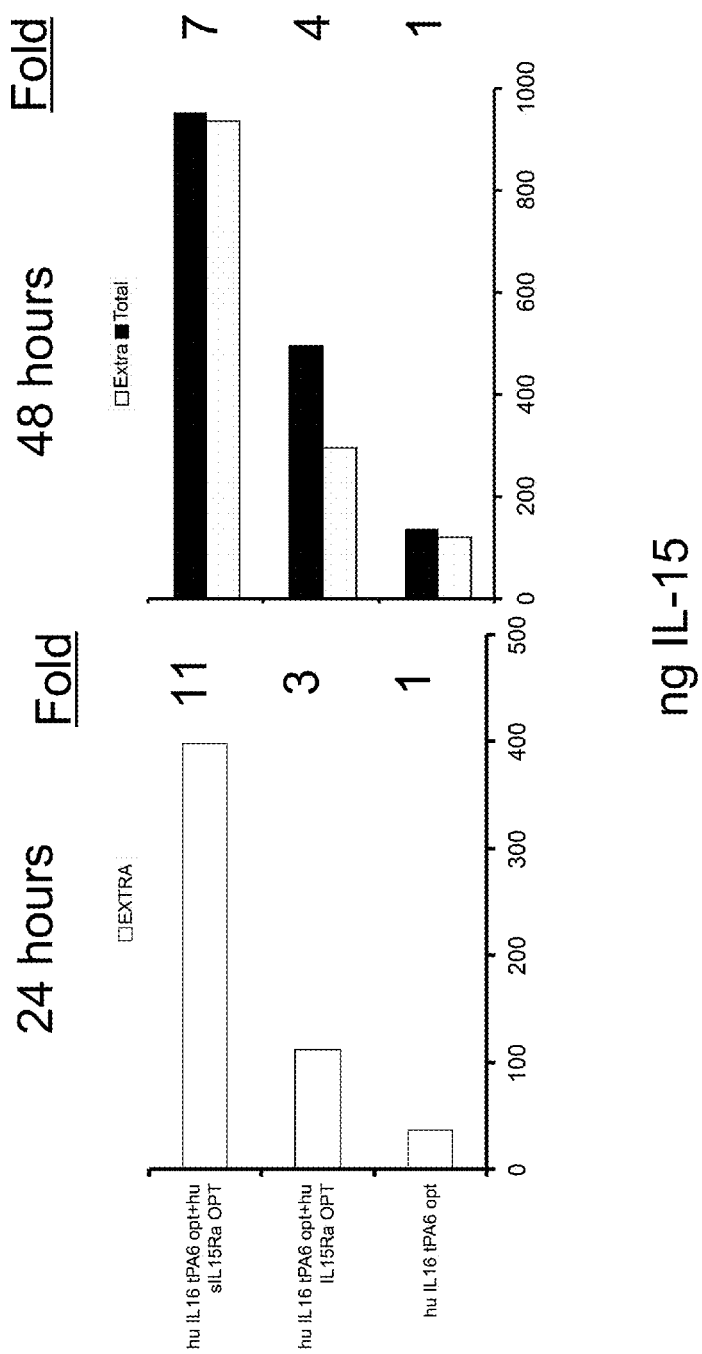

FIG. 40 illustrates that co-expression of IL-15 with IL-15 Receptor alpha improved sequences in human 293 cells in vitro using standard transfection methods led to a dramatic increase of total IL-15 levels measured. Human 293 cells were transfected with 100 ng of plasmid hIL15-tPA6 alone or in combination with either hIL15Receptor alpha (plasmid AG79) or hIL15 soluble Receptor alpha (plasmid AG98) together with 100 ng of GFP and 100 ng SEAP plasmids as transfection controls using Superfect. Medium was sampled after 24 and 48 hours. After 48 hours cells were harvested and ELISA was performed using Quantikine Human IL-15 (R&D systems) to measure IL-15 levels.

Figure 41:
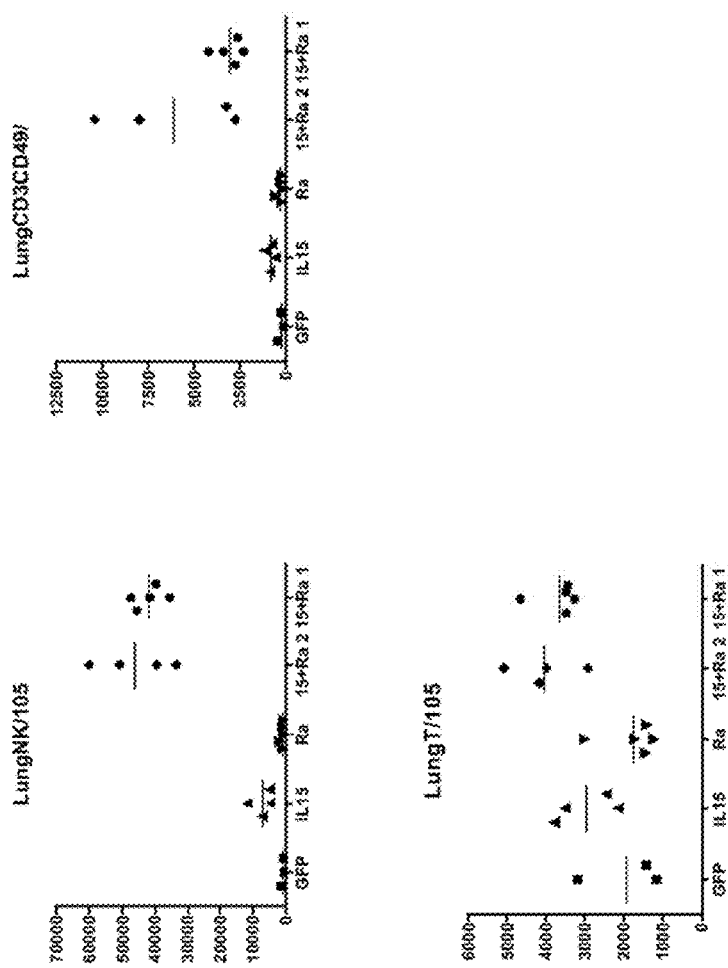

FIG. 41 illustrates the great increase in the levels of lung NK cells and also increases of lung CD3+CD49+ cells when IL-15 and IL-15 receptor DNA were delivered and expressed in mice tissues after tail vein injection. Number of cells are given per $10^5$ cells in the analysis file. Tissues were analyzed 3 days after tail vein injection. The different groups of mice were injected in the tail vein hydrodynamically with the following DNAs:

GFP, 1 µg of plasmid expressing Green Fluorescent Protein (control);

IL15, 1 µg of plasmid expressing the human IL-15 using the plasmid hIL15tPA6 described in our provisional application Ra, 1 µg of plasmid expressing human IL-15 Receptor alpha 15+Ra 2, 2 µg of plasmid expressing IL-15tPA6 and 2 µg of plasmid expressing human IL-15 Receptor alpha 15+Ra 1, 1 µg of plasmid expressing IL-15tPA6 and 1 µg of plasmid expressing human IL-15 Receptor alpha.

Figure 42:
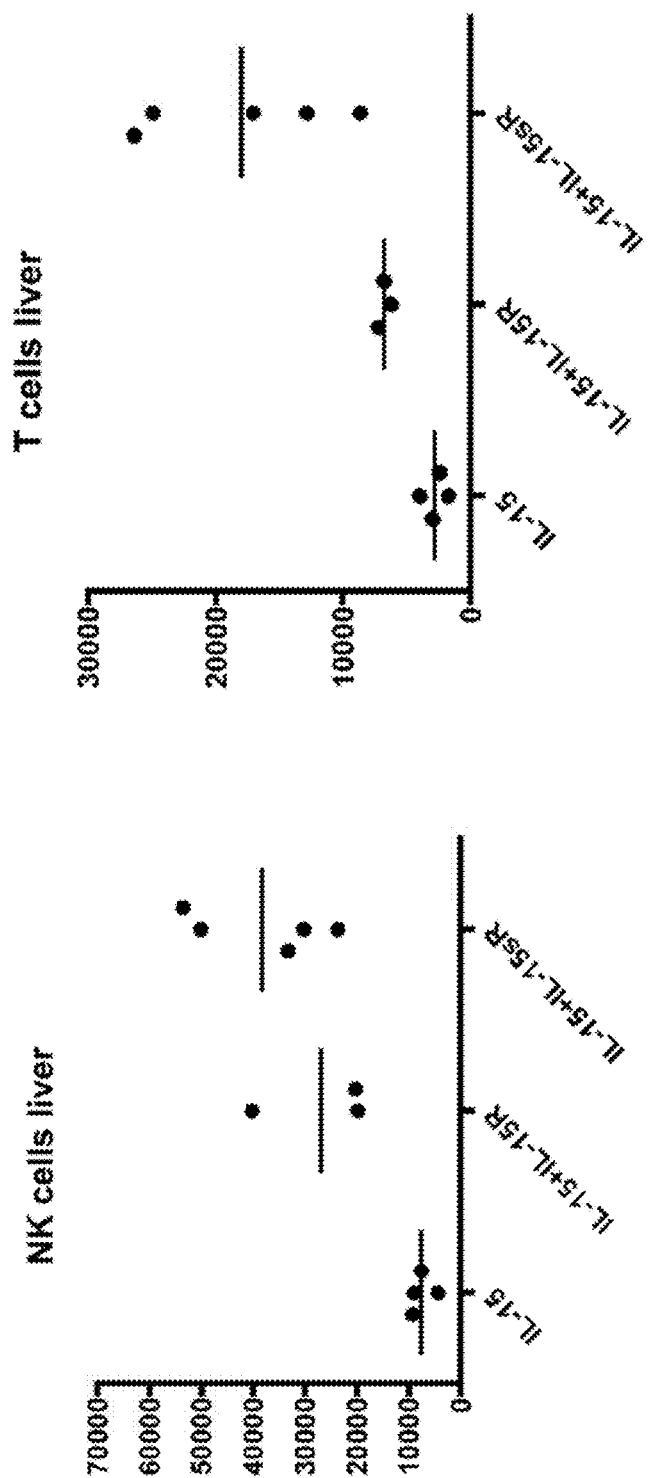

FIG. 42 illustrates the increase of NK cells and T cells in the liver of mice after DNA injection of IL-15 alone, IL-15+IL-15 Receptor alpha, or IL-15+IL-15 soluble Receptor alpha. Number of cells are given per $10^6$ cells in the analysis file. Organs from mice injected with IL-15tPA6 and IL-15 Receptor alpha plasmid DNAs as indicated were digested with collagenase to obtain single cell suspensions. The cells were stained with antibodies against CD3, CD4, CD8, CD49b, CD44 and CD62L and analyzed by flow cytometry. Murine NK cells are phenotypically identified as CD3-CD49b+. IL-15, injection with plasmid IL-15tPA6. IL-15+IL-15R, the plasmid expressing the full IL15Ra was cotransfected. IL-15+IL-15sR, the plasmid expressing the soluble IL-15 Receptor alpha was cotransfected with IL-15tPA6.

Figure 43:
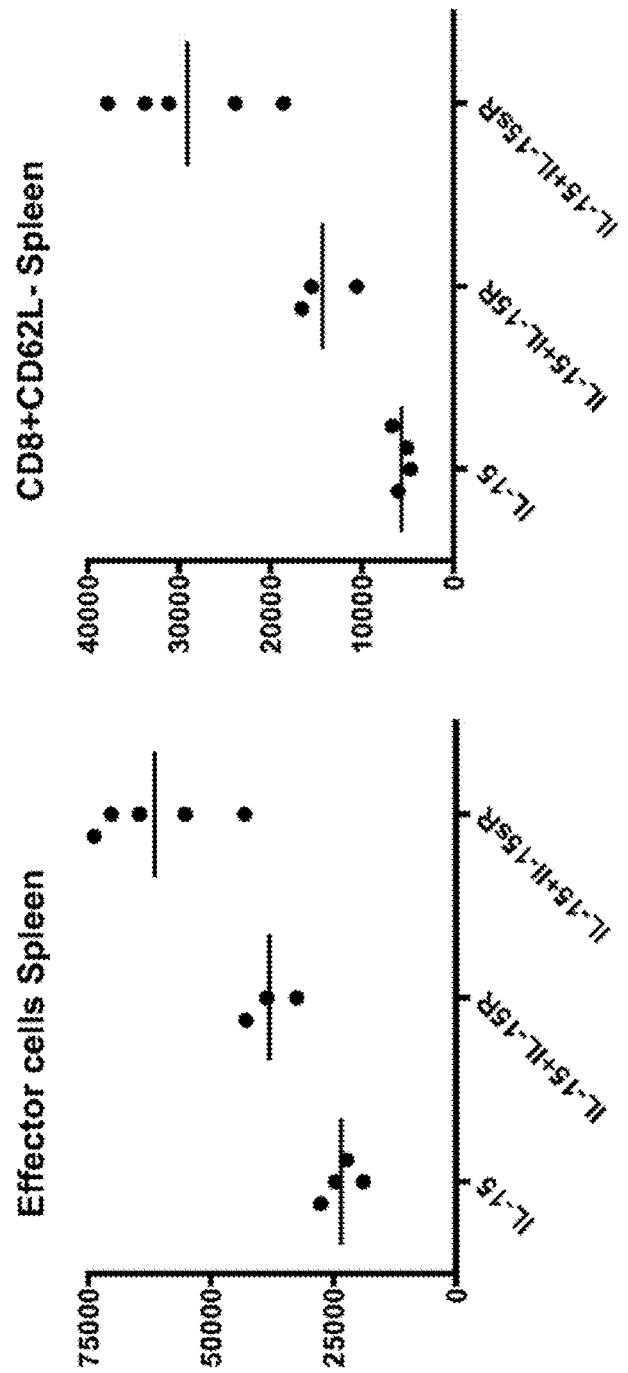

FIG. 43 illustrates the increase in the effector cells in the spleen (total effectors and CD8 effectors, left and right panels, respectively). The lack of CD62L defines a population of murine memory T cells with effector phenotype. Spleens from mice injected with IL-15 and IL-15 Receptor alpha plasmid DNAs as indicated were processed and cells were stained with antibodies against CD3, CD4, CD8, CD49b, CD44 and CD62L and analyzed by flow cytometry.

Figure 44:
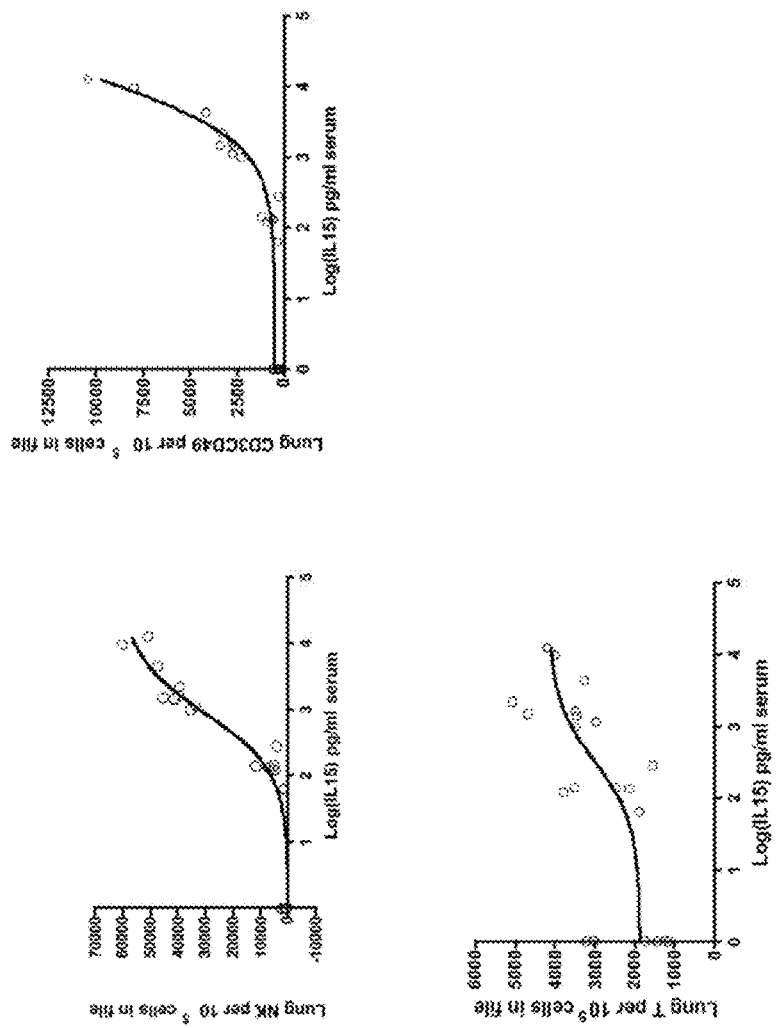

FIG. 44 illustrates that the increased IL-15 levels obtained by stabilization of IL-15 by the IL15Ra are responsible for the increased biological effects. The expression levels of IL-15 using all groups of mice of the experiment shown in FIG. 41 correlate with biological effects. The figure shows the correlation of IL-15 levels with the levels of NK cells, CD3CD49 cells, and T cells measured in the lung 3 days after DNA injection. This indicates that the increased IL-15 levels obtained by stabilization of IL-15 by the IL15Ra are responsible for the increased biological effects in a peripheral tissue such as lung.

Figure 45:
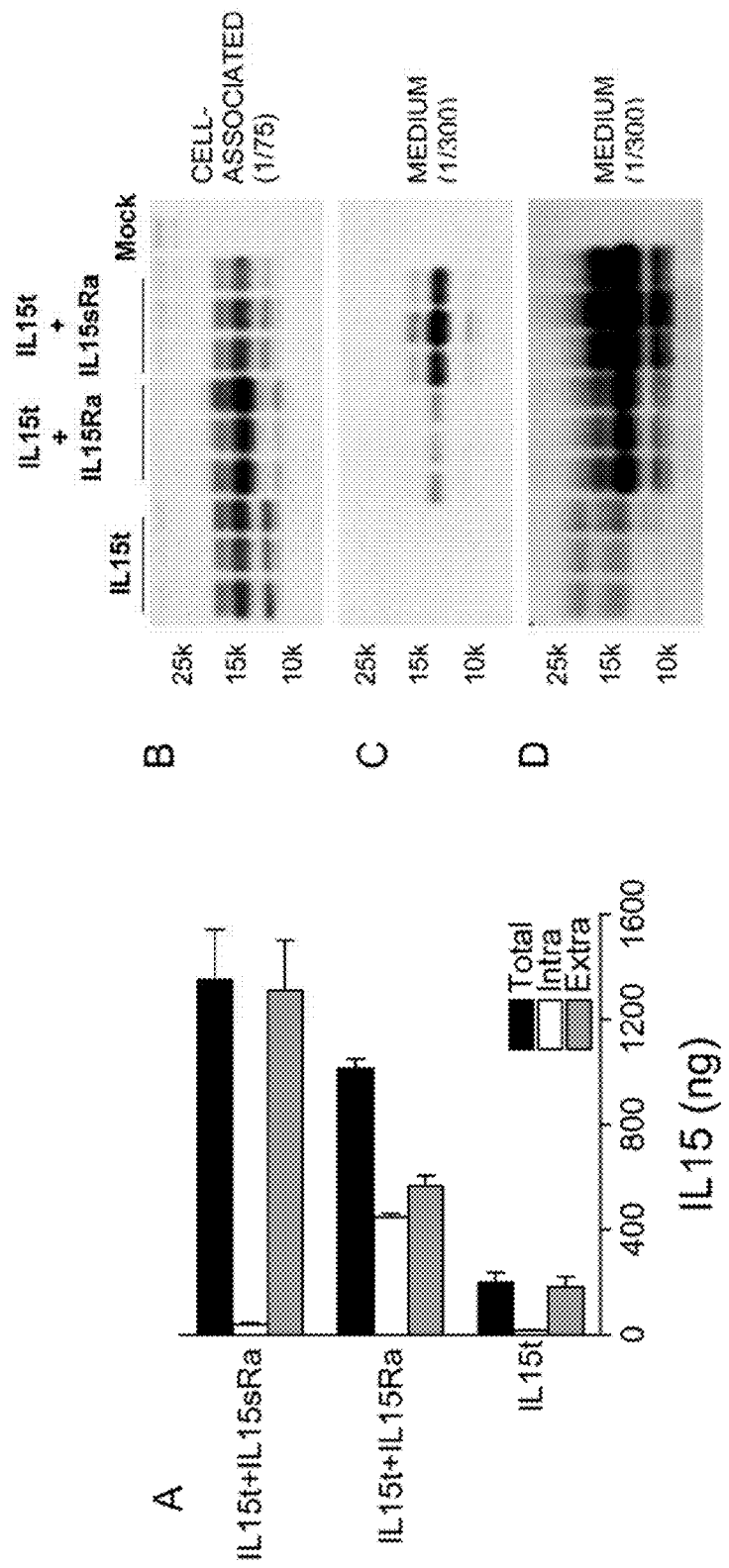

FIG. 45 illustrates that IL15Ra Stabilizes IL-15. A: IL-15 measurements (ELISA) in extracts and media of cells transfected with IL15tPA6 (IL15t) in the presence or absence of IL-15 receptor-expressing plasmids, IL15Ra or IL15sRa. Triplicate samples were measured and bars represent SD of Extracellular (Extra), Intracellular (Intra) and total IL-15 production. B, C, D: Western blot analyses of IL-15 produced after transfections. Triplicate transfections were loaded on 12% NuPage acrylamide gels. B, cell extracts; C, medium of transfected 293 cells; D is a higher exposure of C to visualize IL15t. Electrophoresed proteins were transferred to nylon membranes and IL-15 was visualized by polyclonal anti-human IL-15 antibody (AF315, R&D, 1:3000 dilution) and an enhanced chemiluminesence assay (ECL).

Figure 46:
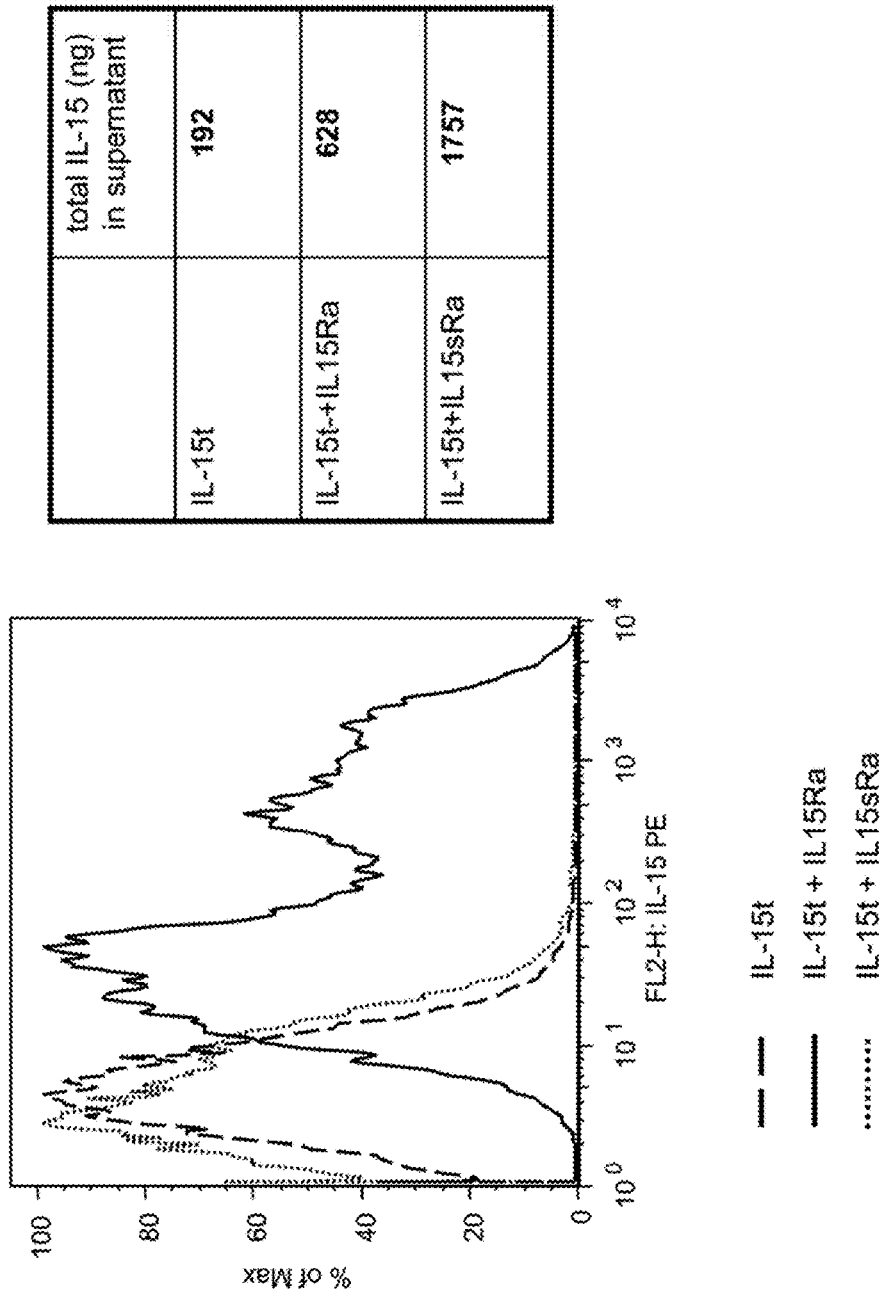

FIG. 46 illustrates that co-transfection of IL-15 with the full receptor alpha leads to large amounts of cell surface associated IL-15 (complexed with IL15Ra), whereas cotransfection with the soluble Receptor alpha does not. Transfected cells were analyzed by flow cytometry after surface staining with Phycoerythrin labelled anti-IL-15 Antibody (R&D). The corresponding levels of IL-15 in the media of the transfected 293 cells are shown at the table to the right (Quantikine Elisa, R&D).

Figure 47:
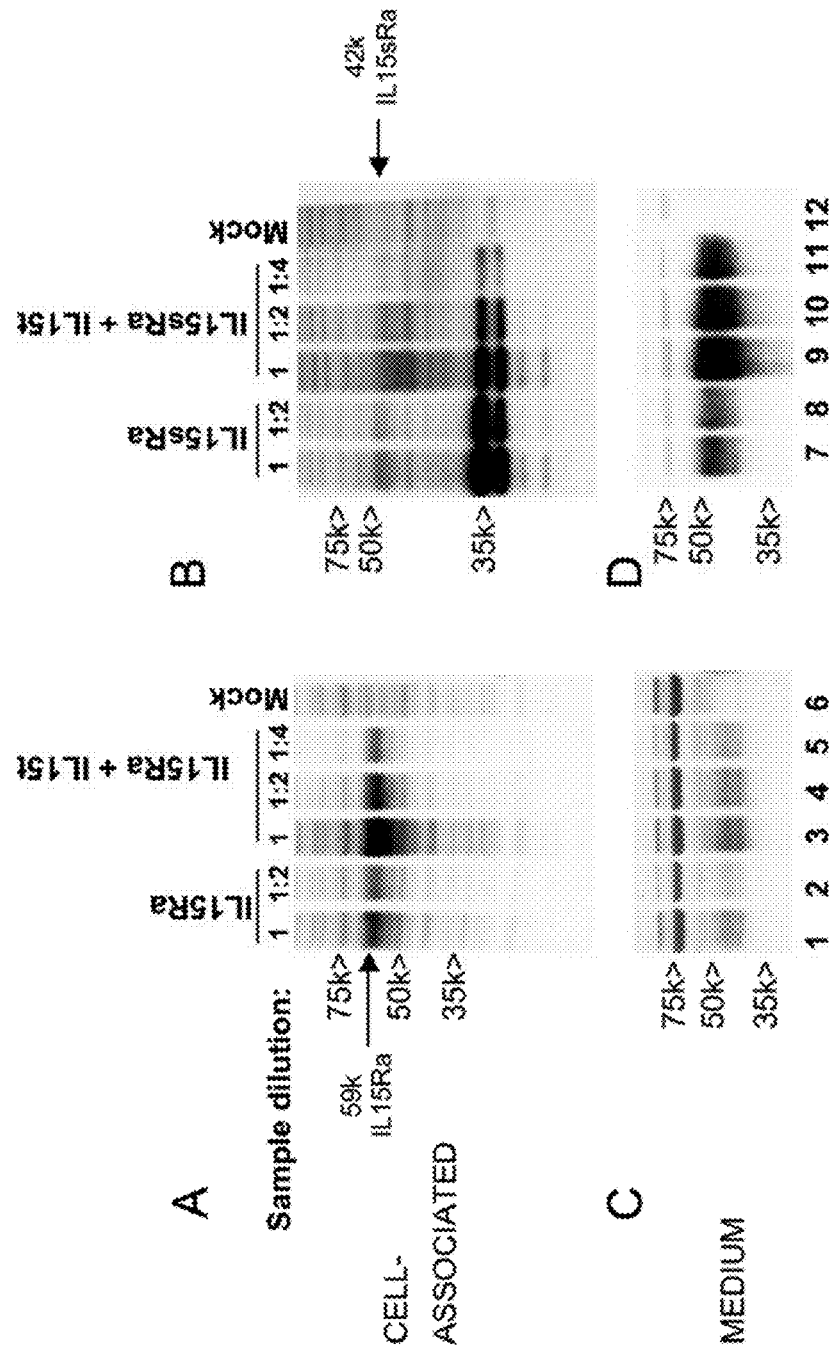

FIG. 47 illustrates that IL-15 coexpression stabilizes IL15Ra. 293 cells were transfected with 50 ng of AG79 hIL15Ra or AG98 IL15sRa alone or in combination with AG59 hIL15tPA6 using the Ca phosphate coprecipitation method. Cells were harvested after 72 hours; media and cell extracts were analyzed for IL15Ra production by gel electrophoresis (10% NuPAGE gel), and western blot using a goat anti-IL15Ra antibody (1:3000 dilution) and a peroxidase-conjugated rabbit anti-goat IgG (1:5000 dilution). Full length glycosylated Receptor alpha migrates as a 59 kDa band, whereas the soluble extracellular part of the Receptor alpha migrates as 42 kDa. Sample dilutions of 1:2 and 1:4 were loaded as indicated at the top to quantify the amounts of produced Receptor. Mock indicates 293 cells transfected with control plasmid only (GFP).

FIGS. 48A-D illustrate the N-glycosylation patterns of IL15Ra. FIG. 48A: The predicted structures of IL15Ra and IL15sRa are indicated. The different domains are indicated. Nglyc indicates potential N-glycosylation sites. FIGS. 48B-C: Coexpression leads to the production of more surface full length Receptor and more secretion of IL15sRa in the medium. Coexpression also releases from cells IL15sRa that is less glycosylated. These results are consistent with the rapid transport and cleavage of IL15Ra at the surface of the cell in the presence of IL-15. In addition, comparison of the total amounts of IL15Ra produced indicates that in the absence of IL-15 the full length Receptor may also be degraded rapidly in the endosomal pathway. In the absence of IL-15, most of the produced IL15sRa from the IL15sRa remains cell associated and migrates as an ~28 kDa band, indicating that it is not processed or degraded post-translationally as rapidly as the full length IL15Ra. Co-expression of IL-15 increased the secreted IL15sRa with concomitant decrease of the intracellular amount. Cell associated, 1/110 of extract loaded; Media, 1/450 loaded. FIG. 48D is a higher exposure of C to visualize the low levels of IL15sRa (produced by IL15Ra alone) in the medium. Lanes indicated with (+) contain material treated with N-glycosidase F (NEB) to identify the degree of N-glycosylation of the produced Receptor.

Figure 49A:
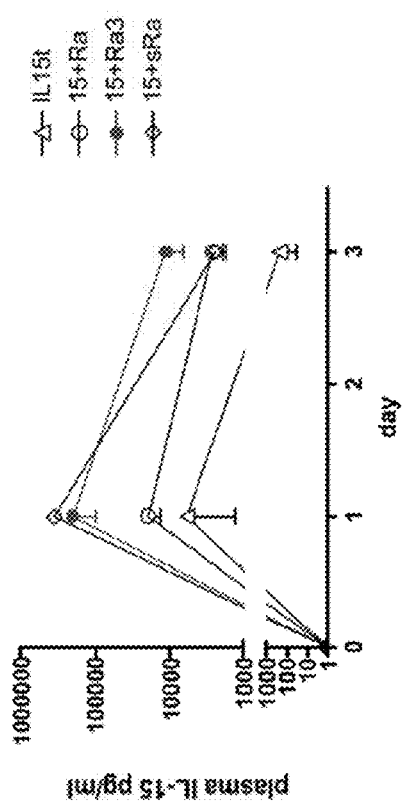

FIG. 49A illustrates IL-15 production in the plasma of mice injected with different DNA expression vectors as indicated. Injection of the wt cDNA expression vector for IL-15 (IL15 wt) leads to low level expression, compared to the optimized vector (IL15t, IL15tPA6), which gives an ~100 fold increase in plasma IL-15 in vivo. To measure IL-15 from the wt vector, 1 µg of DNA was injected per mouse in this experiment. Co-injection of mice with the IL15Ra or IL15sRa plasmids resulted in an addition ~100 fold increase in plasma IL-15 levels ($10^6$-fold total increase). Interestingly, whereas the peak production of IL-15 was highest using the construct expressing IL15sRa, plasma levels decreased more rapidly. Thus co-injection with full length IL15Ra led to more prolonged plasma levels of IL-15, consistent with more gradual cleavage and release from the cell surface. ■ IL-15 wild-type; Δ improved IL-15 with tPA6 SIGPRO peptide (IL15t, also called IL15tPA6); O IL15t and whole IL15Ra; ◇ IL15t and soluble IL15Ra.

Figure 49B:
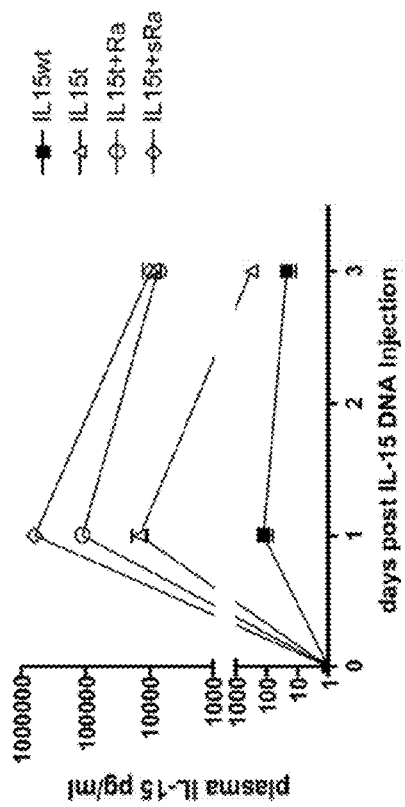

FIG. 49B illustrates improved plasma concentrations of IL-15 when administering nucleic acid vectors encoding IL-15 and ILRa at a 1:3 ratio (w/w). Mice were injected with 0.2 µg of DNA for each plasmid, except of the group 15+Ra3, which was injected with 0.2 IL-15 plasmid and 0.6 IL15Ra plasmid. Bars indicate SD. Excess of full length Receptor led to prolonged stay of IL-15 in the plasma as indicated by the high levels at day 3. Thus, coexpression with sRa leads to highest peak values of plasma IL-15, whereas coexpression with the full-length Ra leads to more prolonged IL-15 levels and possibly function. This is presumably due to more gradual release of surface IL-15 bound to the Receptor upon cleavage of and production of sRa/IL-15 complexes. Such complexes are bioactive, as indicated by the activity of coexpressed IL-15/sRa, which produced only soluble complexes. Δ improved IL-15 with tPA6 SIG- PRO peptide (IL15t); O IL15t and whole IL15Ra (15+Ra); ● IL15t and whole IL15Ra at a ratio of 1:3 (w/w) (15+Ra3); ◊ IL15t and soluble IL15Ra (15+sRa).

Figure 50:
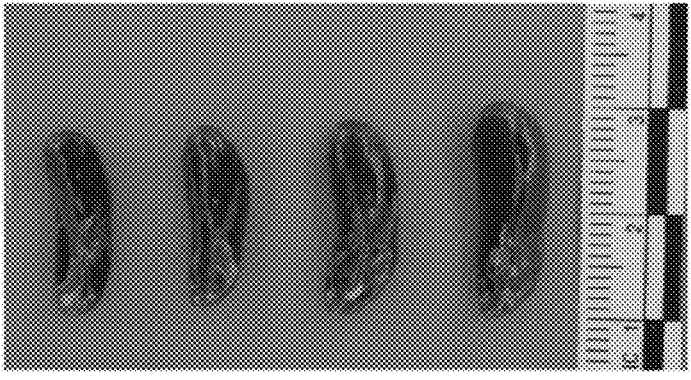

FIG. 50 illustrates the size of mesenteric lymph nodes and spleen 3 days post DNA injection with the indicated DNAs. GFP DNA expression vector was used as negative control. IL-15 expression alone (IL15t) increased more dramatically the size of mesenteric lymph nodes compared to the spleen. This may be the result of strong IL15Ra expression in the lymph nodes, which retains plasma IL-15. The levels of plasma IL-15 measured at 3 days is also indicated.

Figure 51:
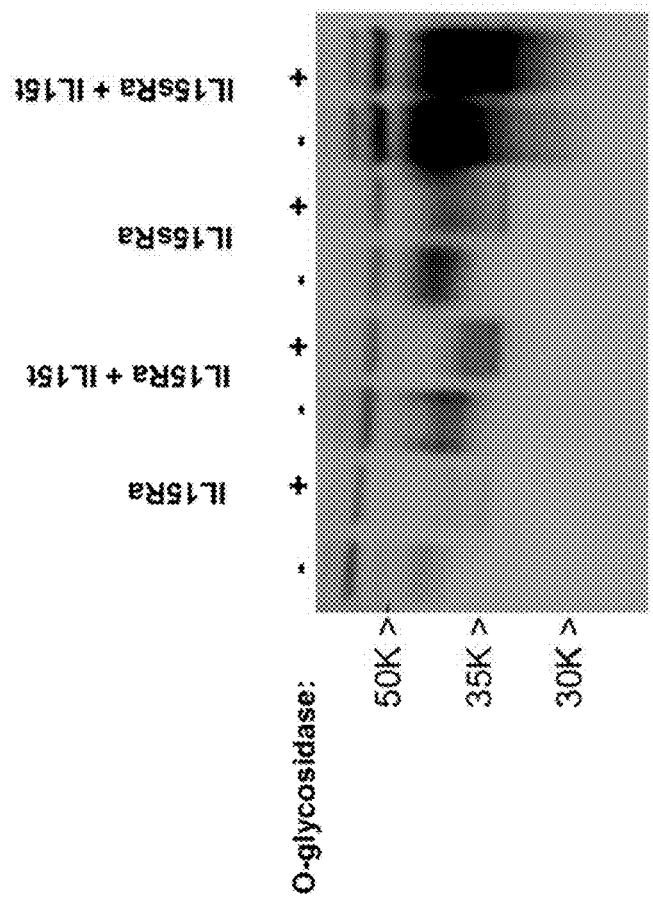

FIG. 51 illustrates that IL15Ra and IL15sRa are O-glycosylated. Treatment with O-glycosidase (Roche) indicates that the secreted forms of the Receptor alpha are O-glycosylated. Media from 293 cells transfected with the indicated constructs were treated with O-glycosidase (lanes indicated with +) and compared to the untreated material (−).

Figure 52:
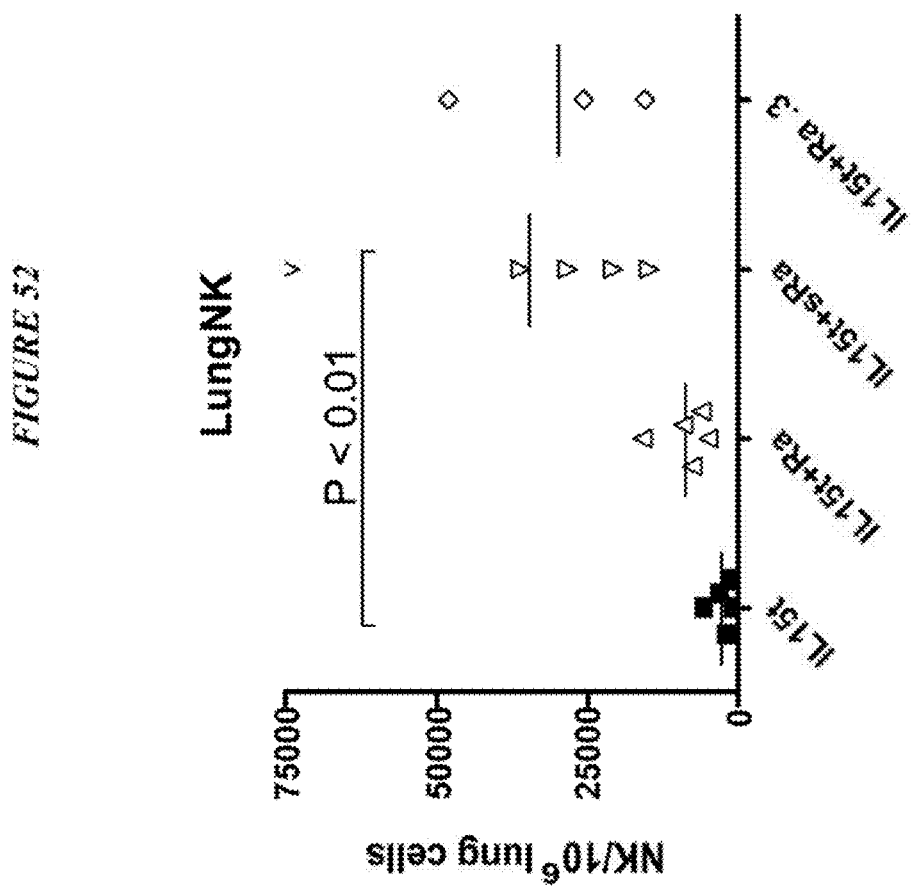

FIG. 52 illustrates increases in lung NK cells 3 days after hydrodynamic DNA delivery of the indicated plasmids in the tail vein of mice. Different groups of mice were injected with 0.1 μg of plasmids expressing IL-15tPA6, IL-15tPA6+ IL15Ra (full length Receptor alpha), IL-15tPA6+IL15sRa (soluble Receptor alpha). The group indicated with IL15t+ Ra.3 received 0.1 μg of IL-15tPA6 and 0.3 μg of IL15Ra plasmids (IL-15 and IL15Ra at a 1:3 ratio (w/w)). This ratio (approximately 1:3) of IL-15 to Receptor DNA showed a trend for more lung NK cells. The difference between IL-15 alone and IL-15+sRa is significant (P<0.01, one-way Anova, Dunnett's Multiple Comparison Test).

Figure 53:
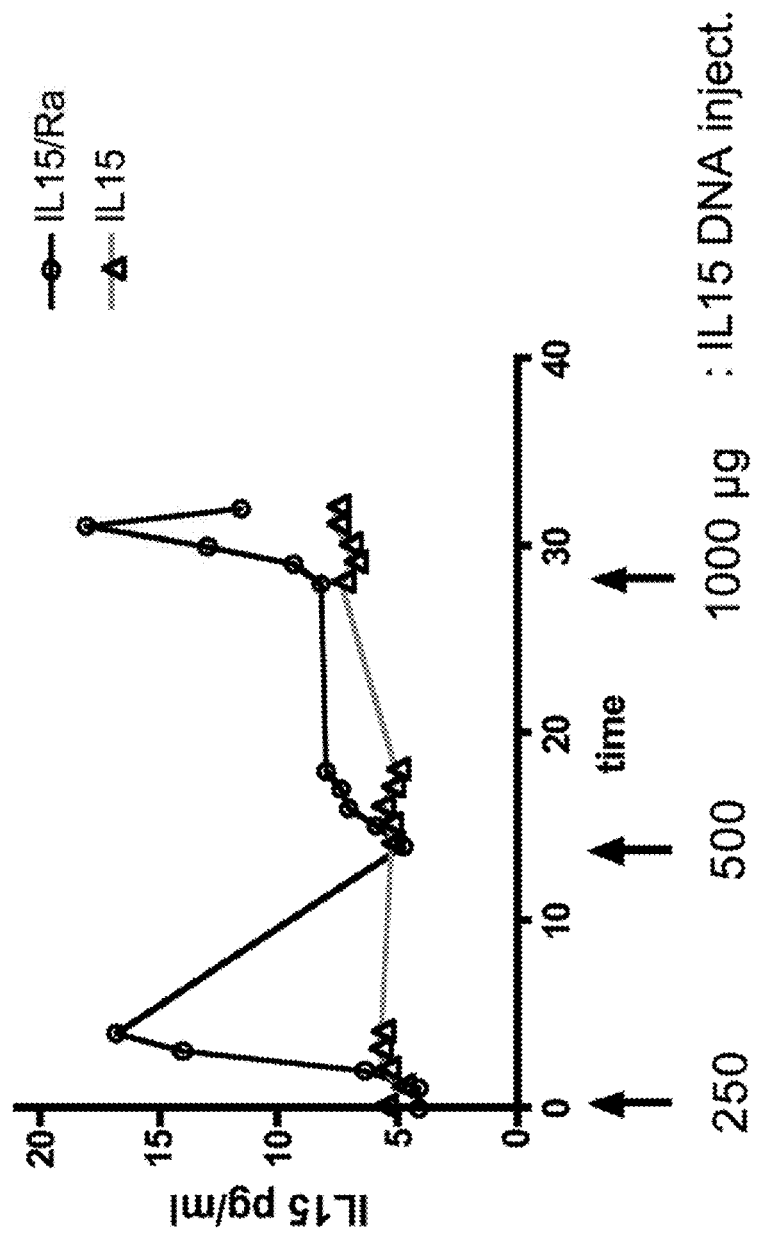

FIG. 53 illustrates plasma IL-15 concentrations (pg/ml) after injection of DNA in macaque muscle. Average plasma values of IL-15 measured in macaque plasma by Elisa (Quantiglo, R&D) at the indicated days. A single IM injection followed by electroporation using Advisys system (Woodlands, Tex., advisys.net) was performed for each macaque at days 0, 14 and 28, as indicated by arrows. Average values for 3 macaques receiving the combination of IL-15/15 Receptor alpha (IL15/Ra, circles) or the IL-15 expression vector only (IL15, triangles) are shown. The results show that IL15/IL15Ra vector combination increased dramatically the plasma levels of IL-15, whereas IL-15 vector alone did not.

Figure 54:
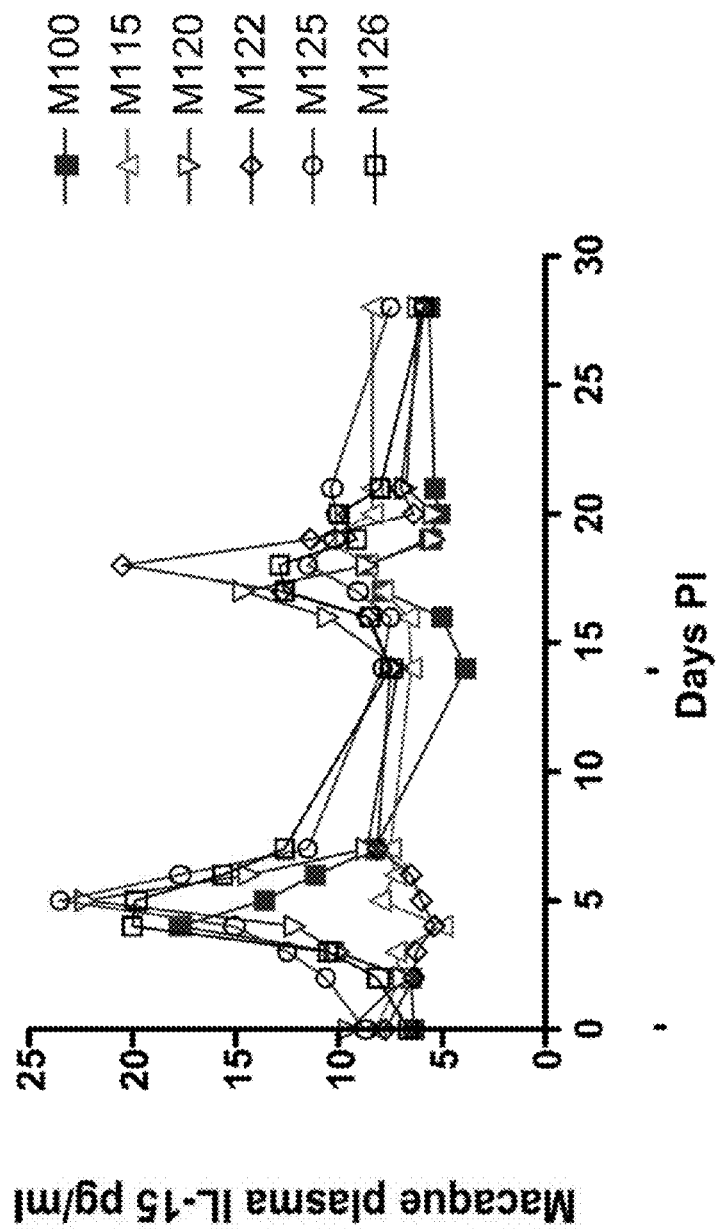

FIG. 54 illustrates that intramuscular injection of IL-15/ 15Ra DNA vectors leads to increased plasma IL-15 levels. Six Rhesus macaques were injected intramascularly in a single site with macaque IL-15/15Ra DNA expression vectors. Two injections of DNA at days 0 and 14 were performed using 100 μg (animals M100, M115, M120) or 250 μg (animals M122, M125, M126) of each plasmid. DNA (0.5 ml) was electroporated in the muscle using the Advisys electroporation system under conditions of 0.5 Amps, 52 msec pulse length, 80 sec lag time using a constant current pulse pattern. The results show elevated plasma IL-15 levels in 4/6 macaque during the first inoculation, and in 6/6 macaques during the second.

Figure 55:
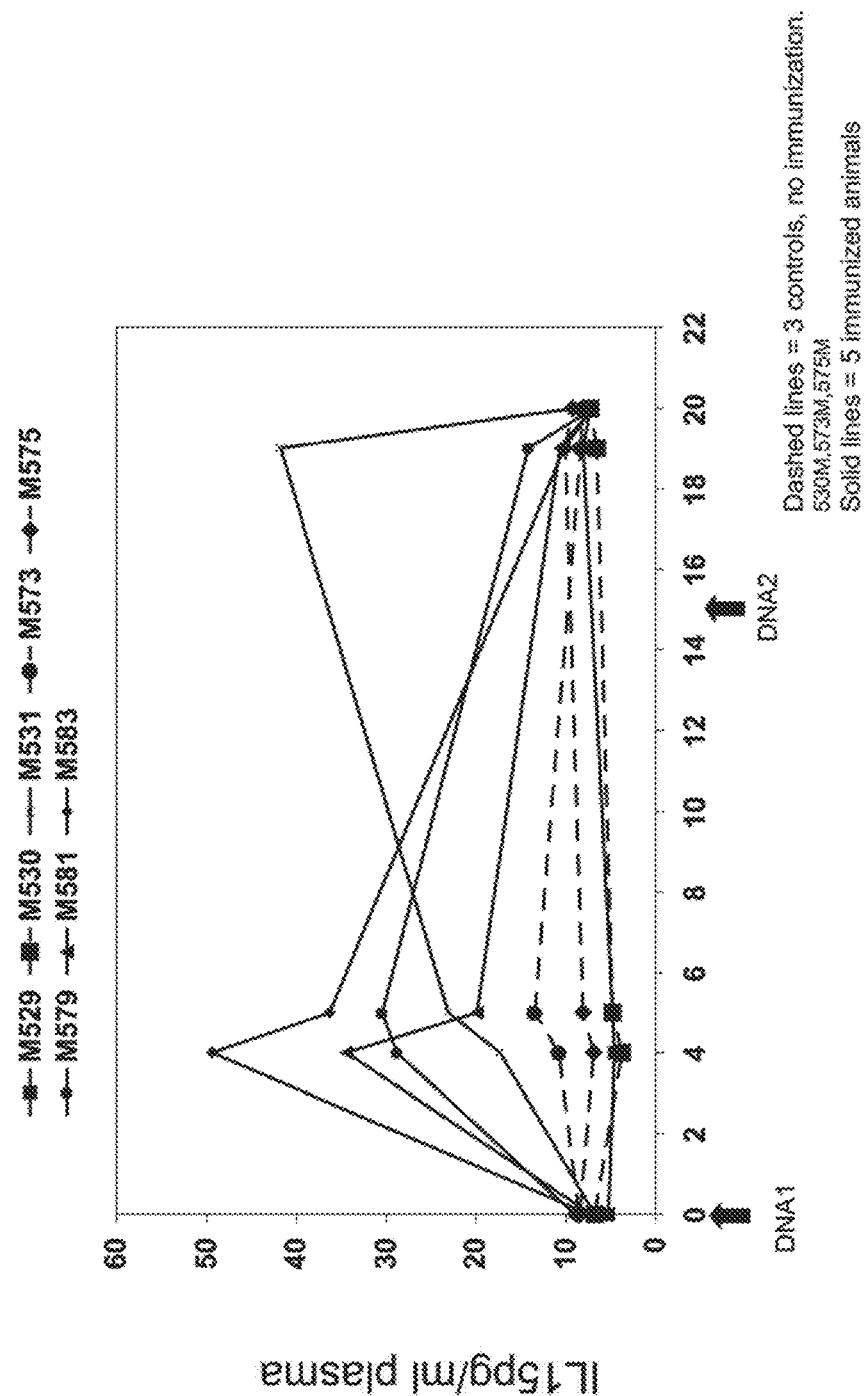

FIG. 55 illustrates IL-15 plasma ELISA at days 4, 5, 19 and 20 after two immunizations. Concentrations of IL-15 (pg/ml) were measured in macaque plasma after DNA vaccination together with IL-15/IL15Ra. Five macaques (M529, M531, M579, M581, M583) were electroporated at days 0 and 15, and plasma was obtained and analyzed by IL-15 ELISA at days 4, 5, 19 and 20. Three animals in the same study (M530, M573, M575; dashed lines) were not immunized and used as controls. Four of the five electroporated animals showed great increases in plasma IL-15, whereas one animal (529M) did not.

Figure 56:
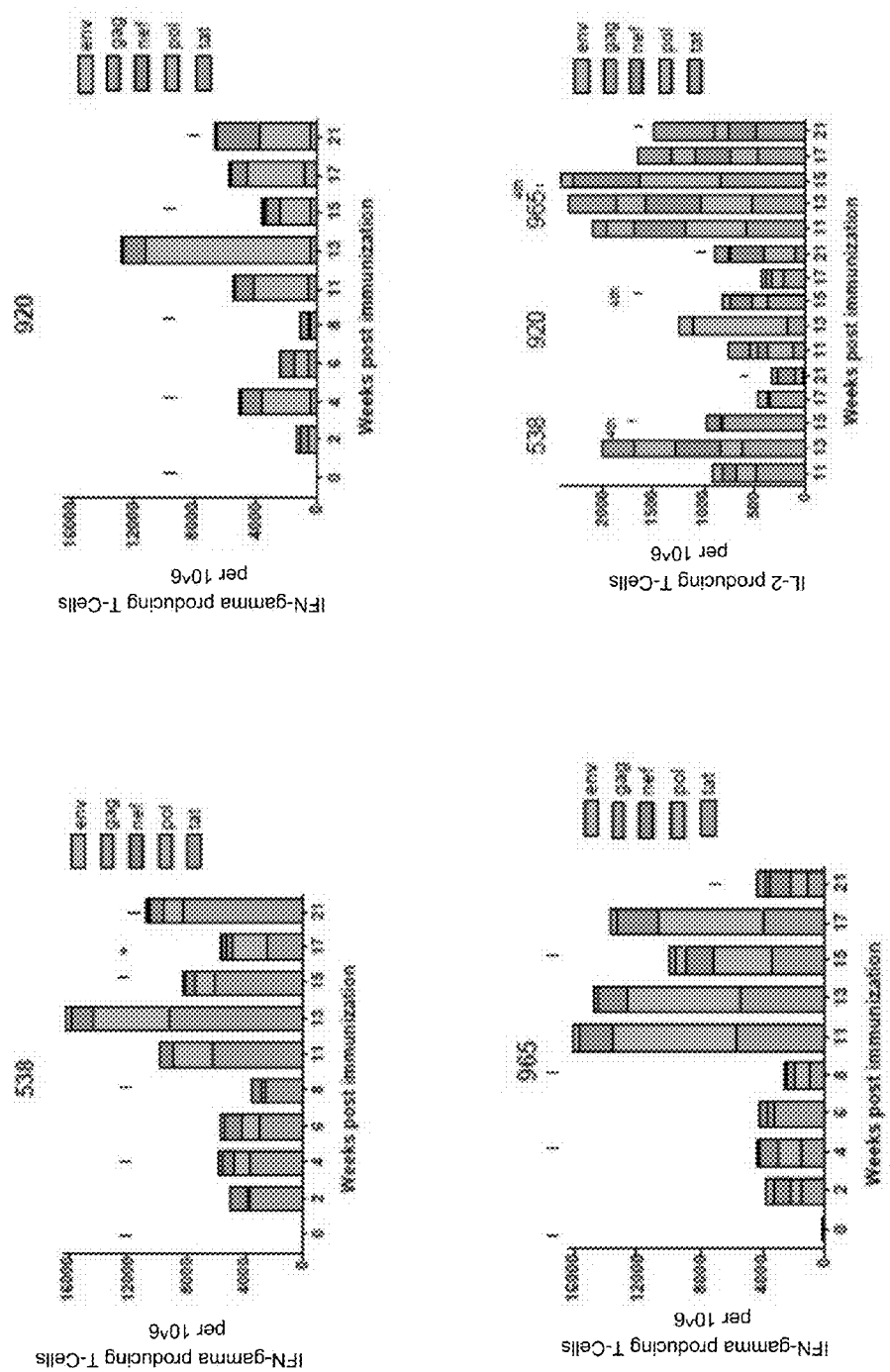

FIG. 56 illustrates IL15/15Ra augmented the specific immune responses against SIV, and assisted in the generation of multifunctional antigen-specific cytokine producing cells (IFNgamma and IL-2) and of effector cells. (Top 3 panels): IFNgamma producing cells per million lymphocytes upon in vitro stimulation with peptide pools for gag, env, nef pol and tat, respectively. The three macaques were vaccinated with a mixture of DNA vectors encoding for SIV antigens, IL-15 and IL15Ra at weeks 0, 4, 8, and PBMC were isolated and tested every 2 weeks as indicated. (Bottom panel): SIV specific IL-2 producing T cells per million lymphocytes at weeks 11-21 (two weeks after release from therapy). PBMC were isolated and stimulated in vitro with peptide pools corresponding to gag, env, nef, tat or pol proteins of SIVmac239. Week 11 was the first time that multifunctional IL-2 secreting SIV specific cells were detected in these macaques. These animal participated in a previous immunotherapy experiment, but did not previously have IL-2 producing cells.

Figure 57:
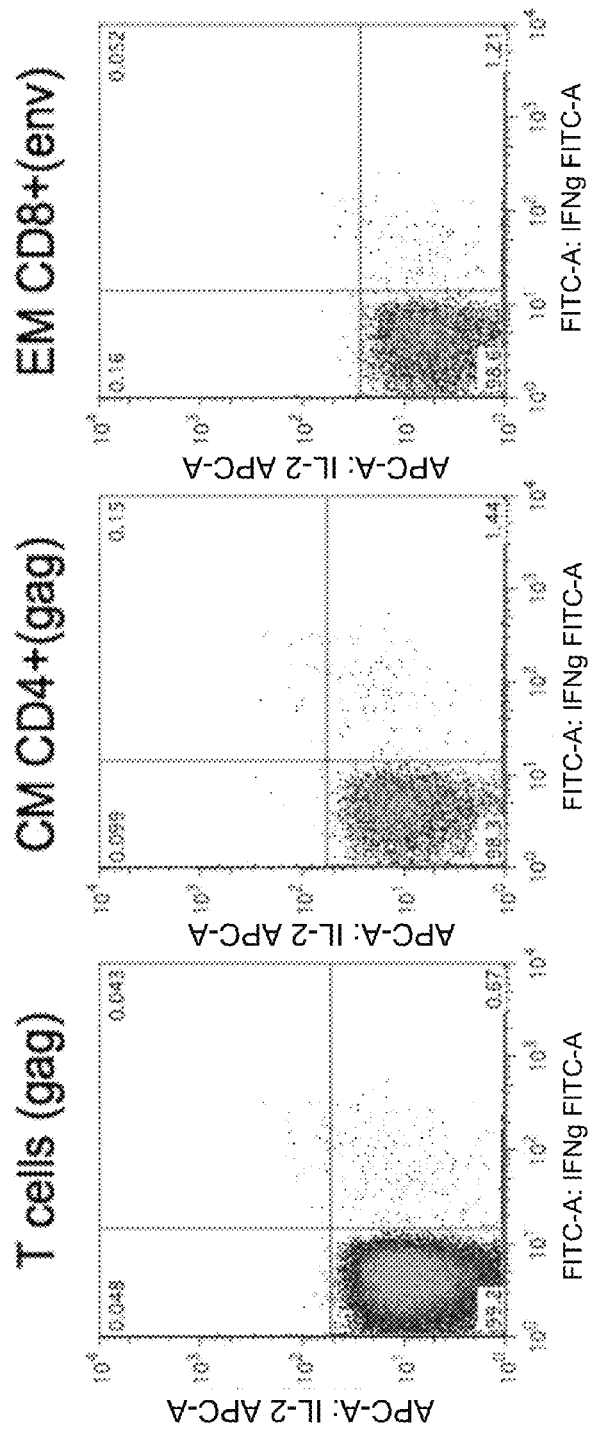

FIG. 57 illustrates the presence of circulating multifunctional central memory (CM) and effector memory (EM) cells in the DNA vaccinated macaques 2 weeks after the third vaccination. CM cells were defined as CD28+CD45RA−. EM cells were CD28-CD45RAlow/+.

Figure 58:
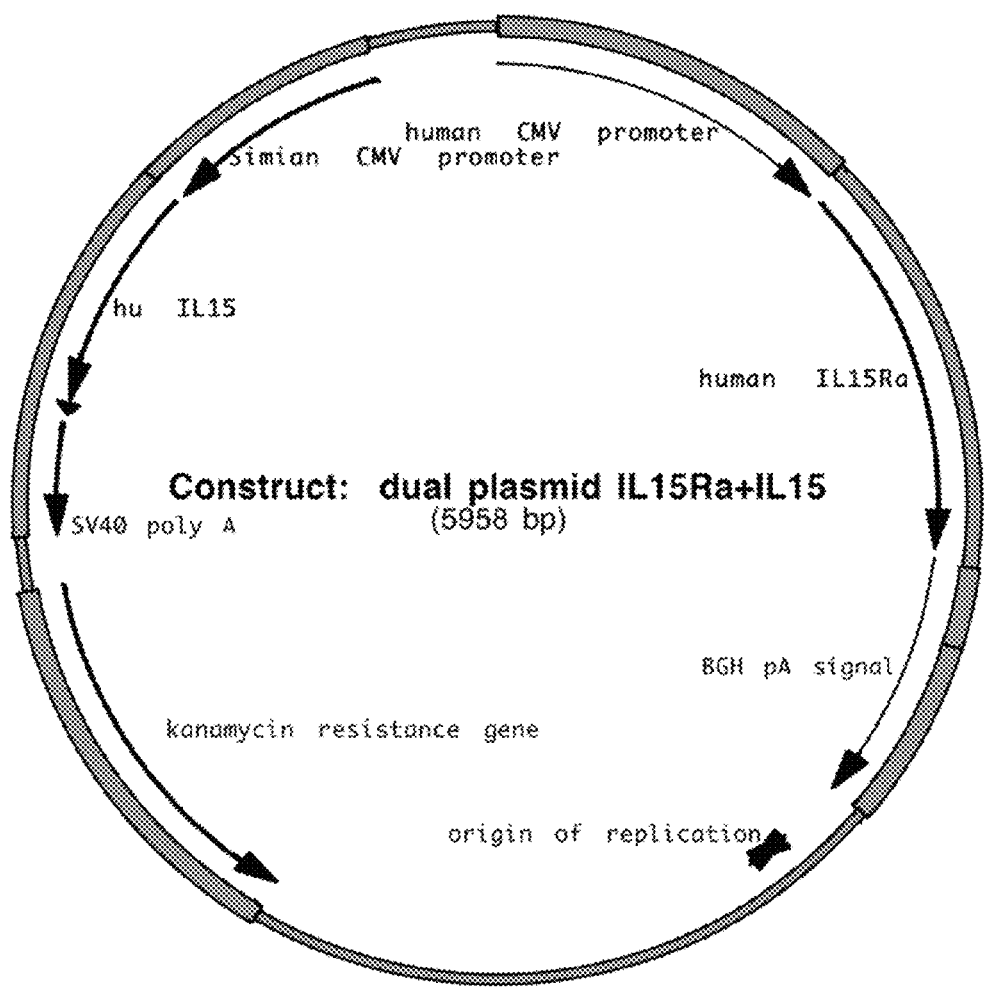

FIG. 58 illustrates a map of a construct that coordinately expresses IL-15 and IL15Ra.

Figure 59:
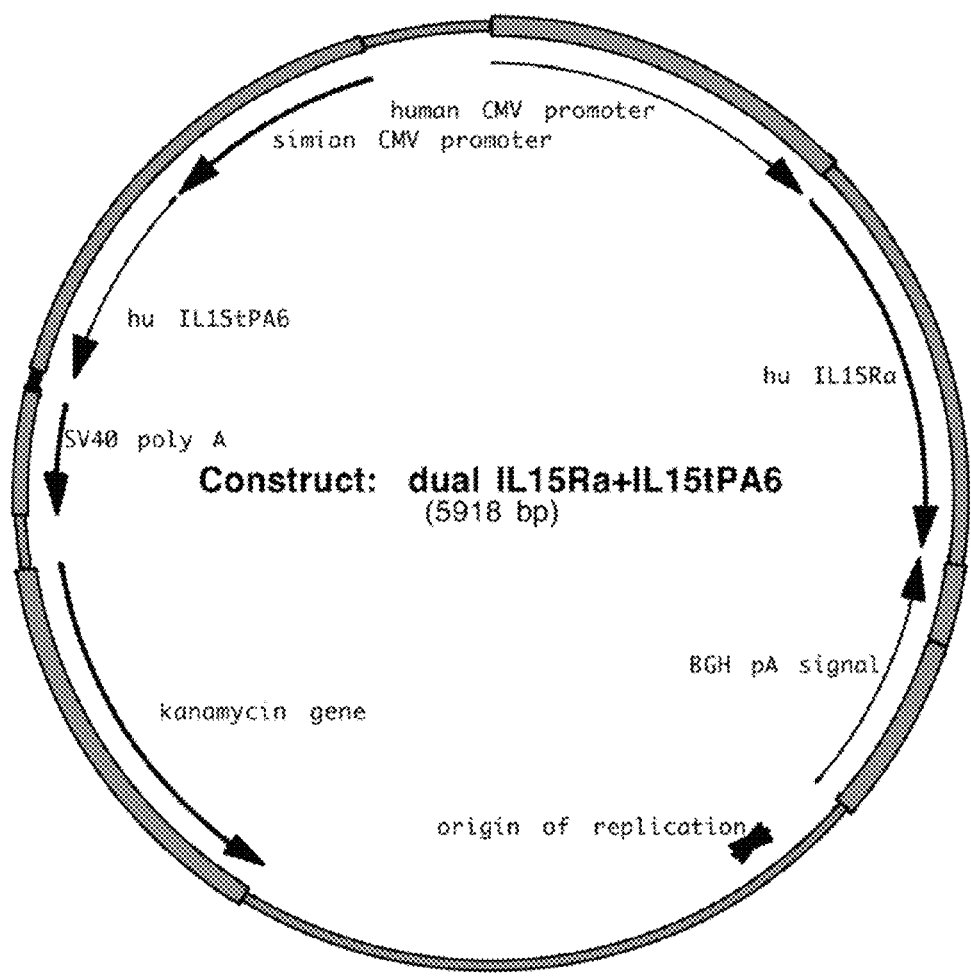

FIG. 59 illustrates a map of a construct that coordinately expresses IL-15tPA6 and IL15Ra.

Figure 60:
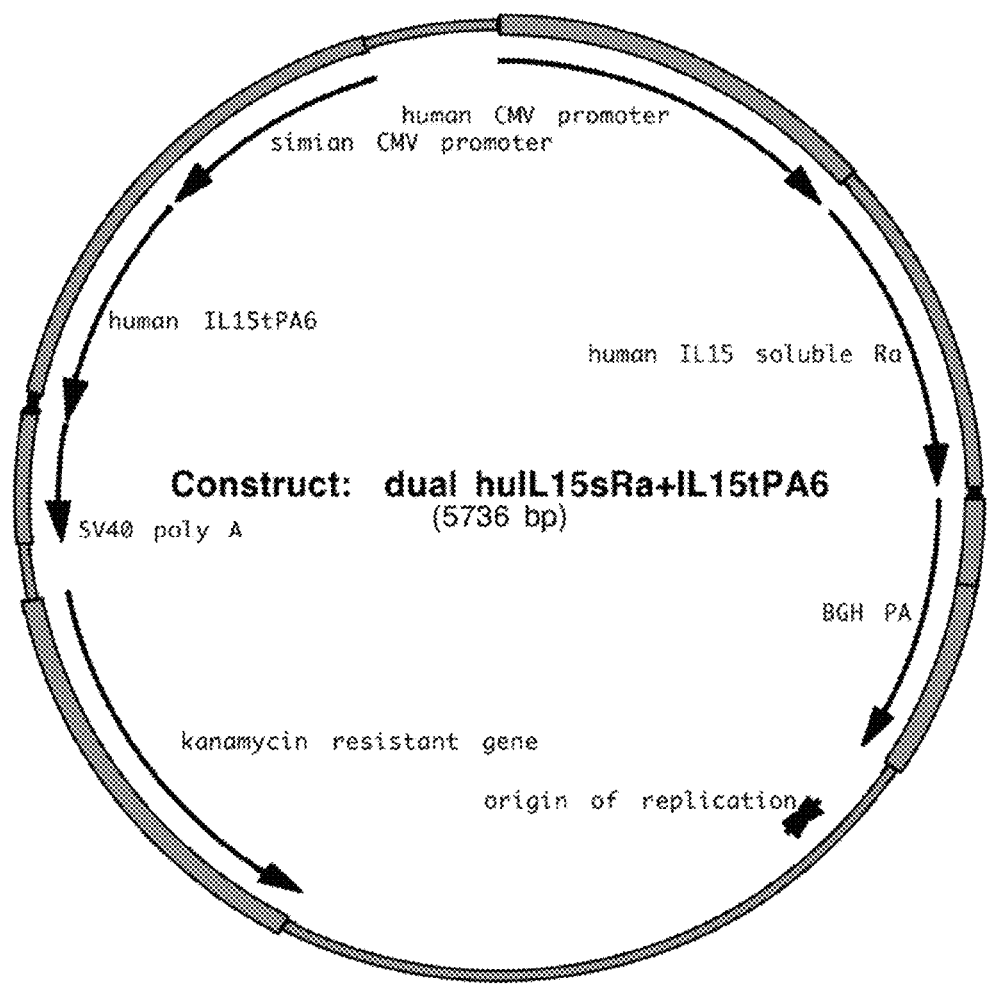

FIG. 60 illustrates a map of a construct that coordinately expresses IL-15tPA6 and IL15sRa.

DETAILED DESCRIPTION

1. Introduction

The cytokine interleukin-15, in encoding nucleic acid or protein form, finds use as an immune cell stimulant (e.g., lymphocyte expansion and activation) and vaccine adjuvant. Native IL-15 coding sequences do not express IL-15 optimally because of several different reasons, including signals within the RNA sequence such as potential splice sites and low stability determinants (oftentimes A/T or A/U rich) sequences embedded within the coding sequences. By minimizing potential splice sites and low stability sequences from IL-15 sequences, expression of IL-15 protein can be increased as much as 4-fold, 5-fold, 6-fold, 8-fold, 10-fold, 15-fold, 20-fold, 30-fold or more in comparison to expression from native mammalian IL-15 sequences. A general method has been established for this purpose, comprising changing several codons of the encoded mRNA to alternative codons encoding the same amino acid (see, e.g., 5,965, 726; 5,972,596; 6,174,666; 6,291,664; 6,414,132; and 6,794,498, the disclosures of each of which are hereby incorporated herein by reference in their entirety for all purposes). This results in the change of any negatively acting signals embedded into the RNA without altering the produced protein.

Figure 1:
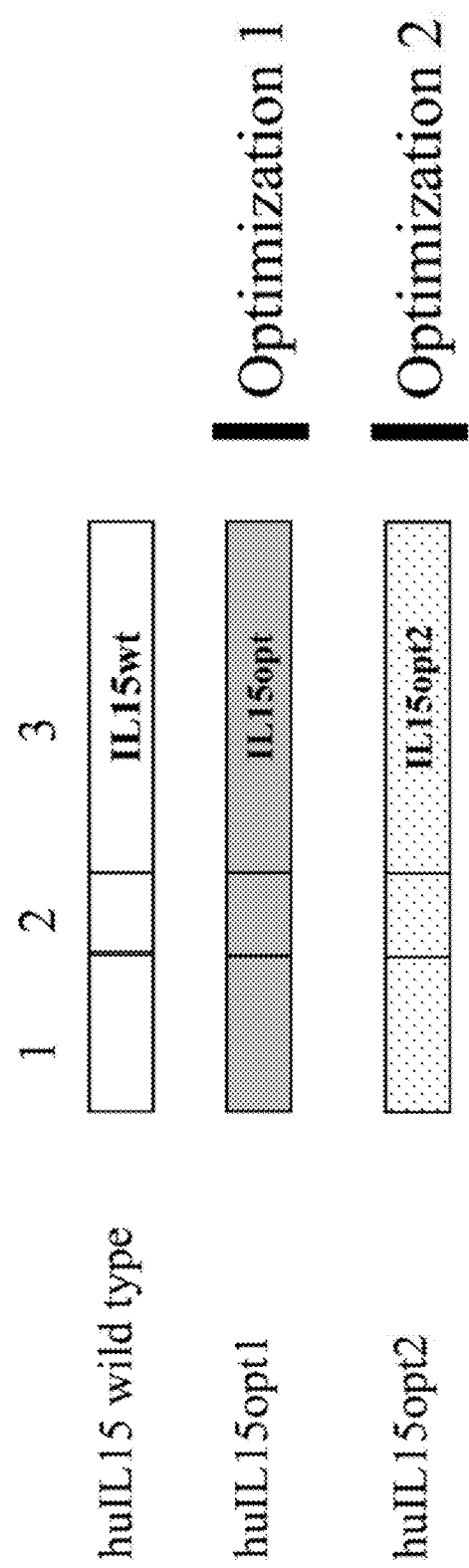
FIG. 1 illustrates strategies of improving the coding sequences of human interleukin-15 (IL-15). Section 1 of the IL-15 polypeptide refers to the signal peptide (amino acids 1-29); section 2 refers to the propeptide (amino acids 30-47); section 3 refers to mature IL-15 (amino acids 47-115). In IL-15opt1, the coding sequence for IL-15 has higher GC content, and potential splice sites are altered. The changes generally do not affect coding potential. In IL-15opt2, the coding sequence improvements are similar to IL-15opt1, but include usage of more "preferred" codons, as defined in U.S. Pat. No. 5,786,464.

Production of IL-15 protein in mammalian cells can be further increased by swapping the native IL-15 signal peptide and/or propeptide sequences with the signal peptide and/or propeptide sequences from a heterologous protein, including for example, tissue plasminogen activator, growth hormone or an immunoglobulin protein. Using an improved coding sequence for mature IL-15 fused to a heterologous signal peptide and/or propeptide, expression levels of IL-15 mammalian cells can be increased 20-fold, 40-fold, 50-fold, 70-fold, 90-fold for more in comparison to expression from a wild-type IL-15 sequence, and an additional 2-fold, 3-fold, 4-fold, 5-fold or more in comparison to expression from an improved IL-15 coding sequence having native signal peptide and/or propeptide sequences (see, FIG. 1).

2. Nucleic Acid Sequences

The improved high expressing IL-15 nucleic acid sequences of the invention are usually based on a native mammalian interleukin-15 coding sequence as a template. Nucleic acids sequences encoding native interleukin-15 can be readily found in publicly available databases including nucleotide, protein and scientific databases available on the worldwide web through the National Center for Biotechnology Information at ncbi.nlm.nih.gov. Native IL-15 nucleic acid sequences can be conveniently cloned from numerous mammalian tissues, including placenta, skeletal muscle, kidney, lung, heart and monocytes/macrophages (see, Grabstein, et al., *Science* (1994) 264:965). Protocols for isolation and stimulation of desired immune cell populations are well known in the art. See, for example, *Current Protocols in Immunology*, Coligan, et al., eds., 1991-2006, John Wiley & Sons.

The sequences are modified according to methods that simultaneously rectify several factors affecting mRNA traffic, stability and expression. Codons are altered to change the overall mRNA AT(AU)-content, to minimize or remove all potential splice sites, and to alter any other inhibitory sequences and signals affecting the stability and processing of mRNA such as runs of A or T/U nucleotides, AATAAA, ATTTA and closely related variant sequences, known to negatively affect mRNA stability. The methods applied to IL-15 coding nucleic acid sequences in the present application have been described in U.S. Pat. Nos. 6,794,498; 6,414,132; 6,291,664; 5,972,596; and 5,965,726 the disclosures of each of which are hereby incorporated herein by reference in their entirety for all purposes.

Generally, the changes to the nucleotide bases or codons of a coding IL-15 sequence do not alter the amino acid sequence comprising an IL-15 protein from the native IL-15 protein. The changes are based upon the degeneracy of the genetic code, utilizing an alternative codon for an identical amino acid, as summarized in Table 1, above. In certain embodiments, it will be desirable to alter one or more codons to encode a similar amino acid residue rather than an identical amino acid residue. Applicable conservative substitutions of coded amino acid residues are described above.

Figure 2:
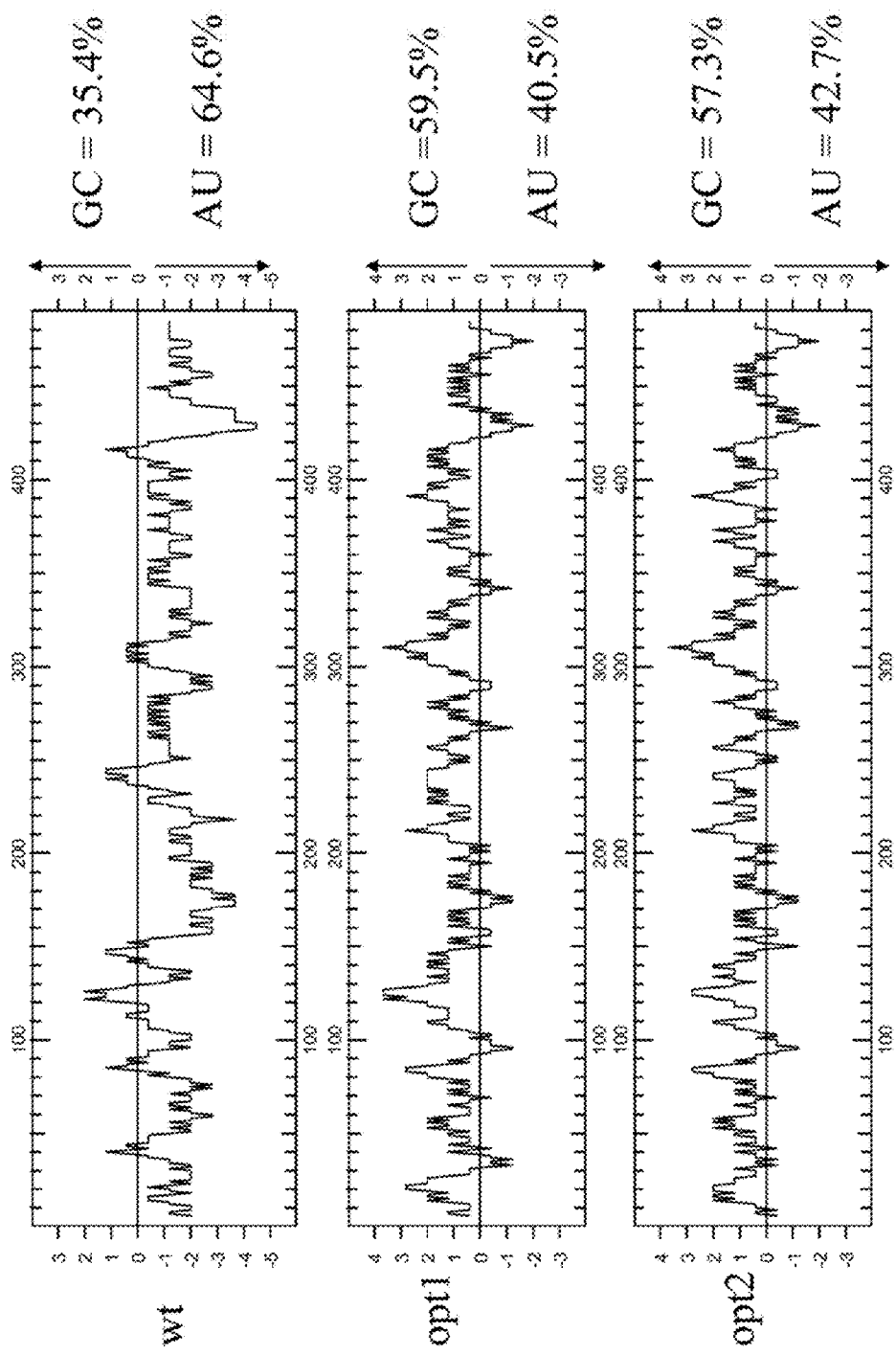
FIG. 2 illustrates a comparison of the AU-GC content profiles of wild-type IL-15 (wt), IL-15opt1 (opt1), and IL-15opt2 (opt2). Both IL-15opt1 and IL-15opt2 have a significant increase in GC content compared to wild-type IL-15 cDNA.
Figure 4:
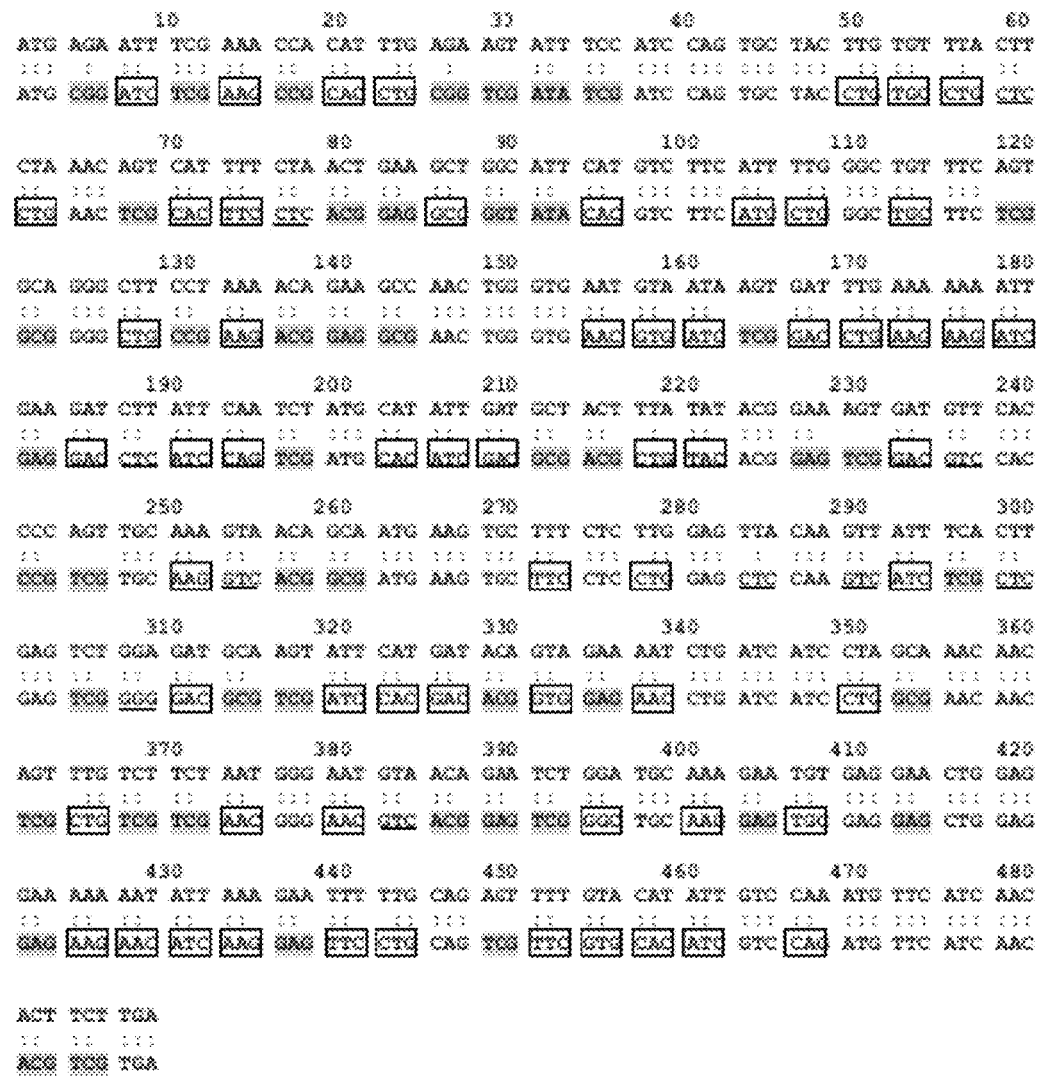

Oftentimes, in carrying out the present methods for increasing the stability of an IL-15 coding sequence, a relatively more A/T-rich codon of a particular amino acid is replaced with a relatively more G/C rich codon encoding the same amino acid (see, for example FIGS. 2 and 4). For example, amino acids encoded by relatively more A/T-rich and relatively more G/C rich codons are shown in Table 2.

TABLE 2

| Amino Acid | relatively more A/T-rich codon(s) | relatively more G/C-rich codon(s) |
| --- | --- | --- |
| Ala | GCA, GCT | GCC, GCG |
| Asn | AAT | AAC |
| Asp | GAT | GAC |
| Arg | CGA, CGT, AGA | CGC, CGG, AGG |
| Cys | TGT | TGC |
| Gln | CAA | CAG |

TABLE 2-continued

| Amino Acid | relatively more A/T-rich codon(s) | relatively more G/C-rich codon(s) |
| --- | --- | --- |
| Glu | GAA | GAG |
| Gly | GGA, GGT | GGC, GGG |
| His | CAT | CAC |
| Ile | ATA, ATT | ATC |
| Leu | TTA, CTA, CTT | TTG, CTC, CTG |
| Lys | AAA | AAG |
| Phe | TTT | TTC |
| Pro | CCA, CCT | CCC, CCG |
| Ser | TCA, TCT, AGT | TCC, TCG, AGC |
| Thr | ACA, ACT | ACC, ACG |
| Tyr | TAT | TAC |
| Val | GTA, GTT | GTC, GTG |

Depending on the number of changes introduced, the improved IL-15 and/or IL15Ra nucleic acid sequences of the present invention can be conveniently made as completely synthetic sequences. Techniques for constructing synthetic nucleic acid sequences encoding a protein or synthetic gene sequences are well known in the art. Synthetic gene sequences can be commercially purchased through any of a number of service companies, including DNA 2.0 (Menlo Park, Calif.), Geneart (Toronto, Ontario, Canada), CODA Genomics (Irvine, Calif.), and GenScript, Corporation (Piscataway, N.J.). Alternatively, codon changes can be introduced using techniques well known in the art. The modifications also can be carried out, for example, by site-specific in vitro mutagenesis or by PCR or by any other genetic engineering methods known in art which are suitable for specifically changing a nucleic acid sequence. In vitro mutagenesis protocols are described, for example, in *In Vitro Mutagenesis Protocols*, Braman, ed., 2002, Humana Press, and in Sankaranarayanan, *Protocols in Mutagenesis*, 2001, Elsevier Science Ltd.

High level expressing improved IL-15 and/or IL15Ra sequences can be constructed by altering select codons throughout a native IL-15 and/or IL15Ra nucleic acid sequence, or by altering codons at the 5'-end, the 3'-end, or within a middle subsequence. It is not necessary that every codon be altered, but that a sufficient number of codons are altered so that the expression (i.e., transcription and/or translation) of the improved IL-15 and/or IL15Ra nucleic acid sequence is at least about 10%, 25%, 50%, 75%, 1-fold, 2-fold, 4-fold, 8-fold, 20-fold, 40-fold, 80-fold or more abundant in comparison to expression from a native IL-15 and/or IL15Ra nucleic acid sequence under the same conditions. Expression can be detected over time or at a designated endpoint, using techniques known to those in the art, for example, using gel electrophoresis or anti-IL-15 or anti-IL15Ra antibodies in solution phase or solid phase binding reactions (e.g., ELISA, immunohistochemistry). Interleukin-15 ELISA detection kits are commercially available from, for example, RayBiotech, Norcross, Ga.; Antigenix America, Huntington Station, NY; eBioscience, San Diego, Calif.; Biosource (Invitrogen), Camarillo, Calif.; R & D Systems (Minneapolis, Minn.), and PeproTech, Rocky Hill, N.J.

Usually at least about 50% of the changed nucleotides or codons whose positions are identified in FIG. 8 are changed to another nucleotide or codon such that the same or a similar amino acid residue is encoded. In other embodiments, at least about 60%, 65%, 70%, 75%, 80%, 85%, 90%, 95%, 95%, 97%, 98%, 99% of the changed codons identified in FIG. 8 are changed to another nucleotide or codon such that the same or a similar amino acid residue is encoded.

The nucleotide positions that can be changed for an improved IL-15 nucleic acid sequence as identified in FIG. 8 are 6, 9, 15, 18, 21, 22, 27, 30, 33, 49, 54, 55, 57, 60, 63, 69, 72, 75, 78, 81, 84, 87, 90, 93, 96, 105, 106, 114, 120, 123, 129, 132, 135, 138, 141, 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486.

The GC-content of an improved IL-15 nucleic acid sequence is usually increased in comparison to a native IL-15 nucleic acid sequence when applying the present methods. For example, the GC-content of an improved IL-15 nucleic acid sequence can be at least about 50%, 51%, 52%, 53%, 54%, 55%, 56%, 57%, 58%, 59%, 60%, 61%, 62%, 63%, 64%, 65% or more.

In some embodiments, the native IL-15 signal peptide (SIG) sequence or signal peptide and propeptide (SIG-PRO) sequence is replaced with the secretory SIG sequence or SIG-PRO sequence from a heterologous protein (i.e., a protein other than IL-15) (see, for example, FIG. 9). Exemplified signal peptide and propeptide sequences include those from tissue plasminogen activator (tPA) protein, growth hormone, GM-CSF, and immunoglobulin proteins. Tissue plasminogen activator signal peptide and propeptide sequences are known in the art (see, Delogu, et al, *Infect Immun* (2002) 70:292; GenBank Accession No. E08757). Growth hormone signal peptide and propeptide sequences also are known in the art (see, Pecceu, et al., *Gene* (1991) 97:253; GenBank Accession Nos. M35049 and X02891). Immunoglobulin signal peptide and propeptide sequences, for example of immunoglobulin heavy chains, also are known in the art (see, Lo, et al., *Protein Eng.* (1998) 11:495 and Gen Bank Accession Nos. Z75389 and D14633). Signal peptide-IL-15 fusion proteins and SIG-PRO-IL-15 fusion proteins can have cleavage sequences recognized by site-specific proteases incorporated at one or more sites of the fusion proteins, for example, immediately before the N-terminal amino acid residue of the mature IL-15. Numerous cleavage sequences recognized by site-specific proteases are known in the art, including those for furin, thrombin, enterokinase, Factor Xa, and the like.

In one embodiment, the native IL-15 signal peptide and propeptide sequences are replaced with the signal peptide and propeptide sequences from tPA. In a further embodiment, the tPA SIG-PRO sequence is altered to remove one or more amino acid residues and/or to incorporate a protease cleavage site (e.g., thrombin, enterokinase, Factor Xa). See, FIG. 12.

In some embodiments, the native IL15Ra signal peptide (SIG) sequence or signal peptide and propeptide (SIG-PRO) sequence is replaced with the secretory SIG sequence or SIG-PRO sequence from a heterologous protein (i.e., a protein other than IL15Ra). Exemplified signal peptide and propeptide sequences include those discussed above, for example, tissue plasminogen activator (tPA) protein, GM-CSF, growth hormone, and immunoglobulin proteins. In some embodiments, the IL15Ra nucleic sequences do not encode an immunoglobulin sequence, for example, an operably linked Fc sequence.

Once a high level expressing improved IL-15 nucleic acid sequence has been constructed, it can be cloned into a cloning vector, for example a TA-cloning® vector (Invitrogen, Carlsbad, Calif.) before subjecting to further manipulations for insertion into one or more expression vectors. Manipulations of improved IL-15 nucleic acid sequences, including recombinant modifications and purification, can be carried out using procedures well known in the art. Such procedures have been published, for example, in Sambrook and Russell, *Molecular Cloning: A Laboratory Manual*, 2000, Cold Spring Harbor Laboratory Press and *Current Protocols in Molecular Biology*, Ausubel, et al., eds., 1987-2006, John Wiley & Sons.

3. Expression Vectors

IL-15 and IL15Ra sequences can be recombinantly expressed from an expression vector containing an improved IL-15 and/or IL15Ra coding sequence. One or both of the IL-15 and/or IL15Ra coding sequences can be improved. The expression vectors of the invention have an expression cassette that will express one or both of IL-15 and IL15Ra in a mammalian cell. The IL-15 and IL15Ra can be expressed from the same or multiple vectors. The IL-15 and IL15Ra can be expressed from the same vector from one or multiple expression cassettes (e.g., a single expression cassette with an internal ribosome entry site; or a double expression cassette using two promoters and two polyA sites). Within each expression cassette, sequences encoding an IL-15 and an IL15Ra will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that promote RNA export (e.g., a constitutive transport element (CTE), a RNA transport element (RTE), or combinations thereof, including RTEm26CTE); sequences that enhance translation efficiency (e.g., Kozak consensus sequence); sequences that enhance protein stability; and when desired, sequences that enhance protein secretion.

The expression vector can optionally also have a third independent expression vector for expressing a selectable marker. Selectable markers are well known in the art, and can include, for example, proteins that confer resistance to an antibiotics, fluorescent proteins, antibody epitopes, etc. Exemplified markers that confer antibiotic resistance include sequences encoding β-lactamases (against (β-lactams including penicillin, ampicillin, carbenicillin), or sequences encoding resistance to tetracylines, aminoglycosides (e.g., kanamycin, neomycin), etc. Exemplified fluorescent proteins include green fluorescent protein, yellow fluorescent protein and red fluorescent protein.

The promoter(s) included in the expression cassette(s) should promote expression of the IL-15 and/or an IL15Ra polypeptide in a mammalian cell. The promoter or promoters can be viral, oncoviral or native mammalian, constitutive or inducible, or can preferentially regulate transcription of IL-15 and/or IL15Ra in a particular tissue type or cell type (e.g., "tissue-specific").

A "constitutive" promoter is a promoter that is active under most environmental and developmental conditions. Exemplified constitutive promoters in mammalian cells include oncoviral promoters (e.g., simian cytomegalovirus (CMV), human CMV, simian virus 40 (SV40), rous sarcoma virus (RSV)), promoters for immunoglobulin elements (e.g., IgH), promoters for "housekeeping" genes (e.g., (β-actin, dihydrofolate reductase).

In another embodiment, inducible promoters may be desired. An "inducible" promoter is a promoter that is active under environmental or developmental regulation. Inducible promoters are those which are regulated by exogenously supplied compounds, including without limitation, a zinc-inducible metallothionine (MT) promoter; an isopropyl thio-galactose (IPTG)-inducible promoter, a dexamethasone (Dex)-inducible mouse mammary tumor virus (MMTV) promoter; a tetracycline-repressible system (Gossen et al, *Proc. Natl. Acad. Sci. USA*, 89: 5547-5551 (1992)); the tetracycline-inducible system (Gossen et al., *Science*, 268: 1766-1769 (1995); see also Harvey et al., *Curr. Opin. Chem. Biol.*, 2: 512-518 (1998)); the RU486-inducible system (Wang et al., *Nat. Biotech.*, 15: 239-243 (1997) and Wang et al., *Gene Ther.*, 4: 432-441 (1997)); and the rapamycin-inducible system (Magari et al. *J. Clin. Invest.*, 100: 2865-2872 (1997)). Other types of inducible promoters which can be useful in this context are those which are regulated by a specific physiological state, e.g., temperature, acute phase, or in replicating cells only.

In another embodiment, the native promoter for a mammalian IL-15 can be used. The native promoter may be preferred when it is desired that expression of improved IL-15 sequences should mimic the native expression. The native promoter can be used when expression of the improved IL-15 and/or IL15Ra must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic expression of native IL-15 and/or IL15Ra.

In another embodiment, the improved IL-15 and/or IL15Ra sequences can be operably linked to a tissue-specific promoter. For instance, if expression in lymphocytes or monocytes is desired, a promoter active in lymphocytes or monocytes, respectively, should be used. Examples of promoters that are tissue-specific are known for numerous tissues, including liver (albumin, Miyatake et al. *J. Virol.*, 71: 5124-32 (1997); hepatitis B virus core promoter, Sandig et al., *Gene Ther.*, 3: 1002-9 (1996); alpha-fetoprotein (AFP), Arbuthnot et al., *Hum. Gene Ther.* 7: 1503-14 (1996)), bone (osteocalcin, Stein et al., *Mol. Biol. Rep.*, 24: 185-96 (1997); bone sialoprotein, Chen et al., *J. Bone Miner. Res.*, 11: 654-64 (1996)), lymphocytes (CD2, Hansal et al., *J. Immunol.*, 161: 1063-8 (1998); immunoglobulin heavy chain; T cell receptor α chain), neuronal (neuron-specific enolase (NSE) promoter, Andersen et al. *Cell. Mol. Neurobiol.*, 13: 503-15 (1993); neurofilament light-chain gene, Piccioli et al., *Proc. Natl. Acad. Sci. USA*, 88: 5611-5 (1991); the neuron-specific vgf gene, Piccioli et al., *Neuron*, 15: 373-84 (1995)); among others.

In some embodiments, the improved IL-15 and/or IL15Ra sequences are operably linked to one or more mRNA export sequences. Exemplified mRNA export elements include the constitutive transport element (CTE), which is important for the nucleo-cytoplasmic export of the unspliced RNA of the simian type D retroviruses. Another exemplified RNA export element includes the RNA transport element (RTE), which is present in a subset of rodent intracisternal A particle retroelements. The CTE and RTE elements can be used individually or in combination. In one embodiment, the RTE is an RTEm26 (e.g., SEQ ID NO:22). In one embodiment, the RTEM26 and the CTE are positioned in the 3'-untranslated region of a transcript encoded by the expression cassette. Often, the RTE and the CTE are separated by 100 nucleotides or less. In some embodiments, the RTE and the CTE are separated by 30 nucleotides or less. In one embodiment, the RTE and the CTE are comprised by the sequence set forth in SEQ ID NO:23 (RTEm26CTE). RNA transport elements for use in further increasing the expression of improved IL-15 sequences are described, for example, in International Patent Publication No. WO 04/113547, the disclosure of which is hereby incorporated herein by reference in its entirety for all purposes.

4. Mammalian Cells

The expression vectors of the invention can be expressed in mammalian host cells. The host cells can be in vivo in a host or in vitro. For example, expression vectors containing high-level expressing IL-15 and/or IL15Ra nucleic acid sequences can be transfected into cultured mammalian host cells in vitro, or delivered to a mammalian host cell in a mammalian host in vivo.

Exemplary host cells that can be used to express improved IL-15 and/or IL15Ra nucleic acid sequences include mammalian primary cells and established mammalian cell lines, including COS, CHO, HeLa, NIH3T3, HEK 293-T, RD and PC12 cells. Mammalian host cells for expression of IL-15 and/or IL15Ra proteins from high level expressing improved IL-15 and/or IL15Ra nucleic acid sequences are commercially available from, for example, the American Type Tissue Collection (ATCC), Manassas, Va. Protocols for in vitro culture of mammalian cells is also well known in the art. See, for example, *Handbook of Industrial Cell Culture: Mammalian, Microbial, and Plant Cells*, Vinci, et al., eds., 2003, Humana Press; and *Mammalian Cell Culture: Essential Techniques*, Doyle and Griffiths, eds., 1997, John Wiley & Sons.

Protocols for transfecting mammalian host cells in vitro and expressing recombinant nucleic acid sequences are well known in the art. See, for example, Sambrook and Russell, and Ausubel, et al, supra; *Gene Delivery to Mammalian Cells: Nonviral Gene Transfer Techniques*, Methods in Molecular Biology series, Heiser, ed., 2003, Humana Press; and Makrides, *Gene Transfer and Expression in Mammalian Cells*, New Comprehensive Biochemistry series, 2003, Elsevier Science. Mammalian host cells modified to express the improved IL-15 nucleic acid sequences can be transiently or stably transfected with a recombinant vector. The improved IL-15 and/or IL15Ra sequences can remain epigenetic or become chromosomally integrated.

5. Administration of Improved IL-15 and/or IL15Ra Sequences

The high level expression improved IL-15 and/or IL15Ra nucleic acid sequences are suitable for administration to an individual alone, for example to treat immunodeficiency (e.g., promote the expansion of lymphocytes, including B cells, T cells, NK cells and NK T cells), or as an adjuvant co-delivered with one or more vaccine antigens. The use of IL-15 and/or IL15Ra for the treatment of immune deficiency and as an adjuvant is known in the art (see, for example, Diab, et al., supra; Ahmad, et al, supra; and Alpdogan and van den Brink, supra).

In one embodiment, high level expressing improved IL-15 and/or IL15Ra nucleic acid sequences are co-administered with one or more vaccine antigens, with at least the improved IL-15 and/or IL15Ra nucleic acid sequences delivered as naked DNA. The one or more antigen can be delivered as one or more polypeptide antigens or a nucleic acid encoding one or more antigens. Naked DNA vaccines are generally known in the art; see, Wolff, et al., *Science* (1990) 247:1465; Brower, *Nature Biotechnology* (1998) 16:1304; and Wolff, et al., *Adv Genet* (2005) 54:3. Methods for the use of nucleic acids as DNA vaccines are well known to one of ordinary skill in the art. See, *DNA Vaccines, Ertl, ed.,* 2003, Kluwer Academic Pub and *DNA Vaccines: Methods and Protocols*, Lowrie and Whalen, eds., 1999, Humana Press. The methods include placing a nucleic acid encoding one or more antigens under the control of a promoter for expression in a patient. Co-administering high level expressing improved IL-15 and/or IL15Ra nucleic acid sequences further enhances the immune response against the one or more antigens. Without being bound by theory, following expression of the polypeptide encoded by the DNA vaccine, cytotoxic T-cells, helper T-cells and antibodies are induced which recognize and destroy or eliminate cells or pathogens expressing the antigen.

In one embodiment, one or both of the IL-15 and/or IL15Ra sequences are co-administered as proteins.

The invention contemplates compositions comprising improved IL-15 and/or IL15Ra amino acid and nucleic acid sequences in a physiologically acceptable carrier. While any suitable carrier known to those of ordinary skill in the art may be employed in the pharmaceutical compositions of this invention, the type of carrier will vary depending on the mode of administration. For parenteral administration, including intranasal, intradermal, subcutaneous or intramuscular injection or electroporation, the carrier preferably comprises water, saline, and optionally an alcohol, a fat, a polymer, a wax, one or more stabilizing amino acids or a buffer. General formulation technologies are known to those of skill in the art (see, for example, *Remington: The Science and Practice of Pharmacy* (20th edition), Gennaro, ed., 2000, Lippincott Williams & Wilkins; *Injectable Dispersed Systems: Formulation, Processing And Performance*, Burgess, ed., 2005, CRC Press; and *Pharmaceutical Formulation Development of Peptides and Proteins*, Frkjr et al., eds., 2000, Taylor & Francis).

Naked DNA can be delivered in solution (e.g., a phosphate-buffered saline solution) by injection, usually by an intra-arterial, intravenous, subcutaneous or intramuscular route. In general, the dose of a naked nucleic acid composition is from about 10 µg to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA vaccinations can be administered once or multiple times. In some embodiments, the improved IL-15 and/or IL15Ra nucleic acid sequences are administered more than once, for example, 2, 3, 4, 5, 6, 7, 8, 10, 15, 20 or more times as needed to induce the desired response (e.g., specific antigenic response or proliferation of immune cells). Multiple administrations can be administered, for example, bi-weekly, weekly, bi-monthly, monthly, or more or less often, as needed, for a time period sufficient to achieve the desired response.

In some embodiments, the improved IL-15 and/or IL15Ra nucleic acid compositions are administered by liposome-based methods, electroporation or biolistic particle acceleration. A delivery apparatus (e.g., a "gene gun") for delivering DNA into cells in vivo can be used. Such an apparatus is commercially available (e.g., BioRad, Hercules, Calif., Chiron Vaccines, Emeryville, Calif.). Naked DNA can also be introduced into cells by complexing the DNA to a cation, such as polylysine, which is coupled to a ligand for a cell-surface receptor (see, for example, Wu, G. and Wu, C. H. (1988) *J. Biol. Chem.* 263:14621; Wilson et al. (1992)*J. Biol. Chem.* 267:963-967; and U.S. Pat. Nos. 5,166,320; 6,846,809; 6,733,777; 6,720,001; 6,290,987). Liposome formulations for delivery of naked DNA to mammalian host cells are commercially available from, for example, Encapsula NanoSciences, Nashville, Tenn. An electroporation apparatus for use in delivery of naked DNA to mammalian host cells is commercially available from, for example, Inovio Biomedical Corporation, San Diego, Calif.

The improved IL-15 and/or IL15Ra nucleic acid vaccine compositions are administered to a mammalian host. The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

6. Methods of Expressing IL-15 and/or IL15Ra in Mammalian Cells

The methods of the present invention provide for expressing IL-15 and/or IL15Ra in a mammalian cell by introducing a recombinant vector into the cell to express the high level improved IL-15 and/or IL15Ra nucleic acid sequences described herein. The modified mammalian cell can be in vitro or in vivo in a mammalian host.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples are offered to illustrate, but not to limit the claimed invention.

Example 1

The strategy for introducing nucleotide changes into IL-15 sequences is to simultaneously rectify several factors affecting mRNA traffic, stability and expression. Codons are altered to change the overall mRNA AT(AU)-content or to remove any other inhibitory signals within the RNA such as all potential splice sites (computer programs predicting potential splice sites can be found for example at web sites such as fruitfly.org/seq_tools/splice.html, or sun1.softberry.com/berry.phtml) and also to alter sequences such as runs of A or T/U nucleotides, AATAAA, ATTTA and closely related variant sequences, known to negatively affect mRNA. By substituting codons with a different codon encoding the identical amino acid, the chosen codon can be more GC-rich, or can have a different sequence that is sufficient to alter the RNA structure. This approach has been described in several patents, each of which is hereby incorporated herein by reference in their entirety: U.S. Pat. Nos. 5,965,726; 5,972,596; 6,174,666; 6,291,664; 6,414,132; and 6,794,498.

Procedures

Standard lab techniques are used to generate, purify and sequence plasmid DNAs. One microgram (1 μg) of the plasmids containing the indicated IL-15 coding sequence were transfected into human 293 or RD cells seeded into 60 mm plates the day before with $10^6$ cells using calcium coprecipitation technique (293 cells) and the SuperFect Reagent protocol (Qiagen) for RD4 cells. 2-3 days later, intracellular and extracellular and total IL-15 protein was measured using commercial kits (R&D system). Due to the high homology of the human and Rhesus IL-15 proteins, their protein levels were determined by the same commercial ELISA kit. The results of different experiments are shown in FIGS. 7, 10, 11, 13, 25, 26 and 27.

Example 2

This example demonstrates the improved expression sequences for IL-15 Receptor alpha and the soluble (extracellular) part of IL-15 Receptor alpha (IL15sRa). These improved sequences increased protein expression of the IL-15 Receptor alpha and provide a method to further optimize the activity of IL-15 in vivo and in vitro.

Results

FIGS. 39 and 40 show that co-expression of IL-15 with IL-15 Receptor alpha optimized sequences in human 293 cells in vitro using standard transfection methods led to a dramatic increase of total IL-15 levels measured. This increase is the result of stabilization of the IL-15 molecule by binding to the whole IL-15 receptor alpha or to the extracellular part of the IL-15 receptor alpha. The results were similar if the IL-15 and the receptor were expressed by two different plasmids or expressed by a single plasmid from two different promoters.

FIG. 41 shows a great increase in the levels of lung NK cells and also increases of Lung CD3+CD49+ cells when IL-15 and IL-15 receptor DNA were delivered and expressed in mice tissues after tail vein injection. The number of cells is given per $10^5$ cells in the analysis file.

FIG. 42 shows the increase of NK cells and T cells in the liver of mice after DNA injection of IL-15 alone, IL-15+ IL-15 Receptor alpha, or IL-15+IL-15 soluble Receptor alpha. The number of cells is given per $10^6$ cells in the analysis file.

FIG. 43 shows the increase in the effector cells in the spleen (total effectors and CD8 effectors, respectively). The lack of CD62L defines a population of murine memory T cells with effector phenotype.

FIG. 44 indicates that the increased IL-15 levels obtained by stabilization of IL-15 by the IL15Ra are responsible for the increased biological effects.

Methods:

Expression in Cultured Cells

Human 293 cells were transfected with 0.1 μg of the human IL15tPA6OPT plasmid either alone or together with 0.1 μg of a plasmid expressing the RNA optimized versions of the human IL-15 receptor alpha using either the full length form (huIL15RaOPT) or the soluble form (hu sIL15RaOPT). Medium was taken at 24 and at 48 hours posttransfection and cells were harvested at 48 hrs. IL-15 levels were measured using Quantikine Human IL-15 immunoassay (R&D systems) prior to release from the cell.

Expression in Mouse

Six week old Balb/c mice were either injected with DNA via the intramuscular route into both of the quadriceps or hydrodynamically via the tail vein. For the hydrodynamic DNA delivery, the mice were injected with 1 μg of human IL15-tPA6OPT plasmid either alone or together with 1 μg the plasmid expressing the human IL-15 Receptor alpha using either the intact form (huIL15RaOPT) or the soluble form (hu sIL15RaOPT) in 1.6 ml of sterile 0.9% NaCl via the tail vein. Three days later, mice were sacrificed and the levels of IL-15 were measured in the plasma using a commercial chemiluminescent immunoassay (Quantiglo, R&D). The bioactivity of IL-15 was measured in liver, spleen and lung using multicolor FACS. Briefly, cells were staining ex-vivo with the following panel of conjugated rat anti-mouse antibodies: APCCy7-CD3, PerCP-CD4, PECy7-CD8, APC-CD44, FITC-CD49b and PE-CD62L, BD-Pharmingen and analyzed by flow cytometry. Murine NK cells are phenotypically identified as CD3-CD49b+.

Example 3

This example demonstrates the mutual stabilization of IL-15 and IL-15 Receptor alpha. The data demonstrate that combined production of IL-15 and IL15Ra endogenously allows the two molecules to efficiently combine in a functional secreted form.

In the presence of IL-15, the IL-15 Receptor alpha is rapidly delivered to the surface of the cell (see, FIG. 46) and it is also rapidly cleaved (see, FIG. 47). Thus, expression of the full receptor leads rapidly to the soluble receptor/IL-15 complex, which is released in the circulation and can act at distant tissues.

This example follows the in vivo production of IL-15 by measuring the plasma levels over time (see, FIG. 49). The soluble receptor/IL-15 gene combination gives a sharp peak of plasma IL-15, which is rapidly decreased, whereas the complete receptor/IL-15 combination gives a lower peak but decays less rapidly. This allows the delivery of different formulations having more or less prolonged action in vivo.

Results

Cells transfected with IL-15 alone express and secrete IL-15 inefficiently. In addition, like many cytokine mRNAs, the IL-15 mRNA is unstable and can be improved by RNA/codon optimization. RNA/codon optimization can be used to increase IL-15 and IL15Ra mRNA levels and expression. In addition, the secretory pre-peptide of IL-15 can be exchanged with the tissue Plasminogen Activator (tPA) secretory leader peptide, or with other secretory peptides such as IgE or GM-CSF. These improvements have resulted in a 100-fold increase of expression using the human CMV promoter and Bovine Growth Hormone polyadenylation signal in standard expression vectors.

FIG. 45 shows the in vitro expression of IL-15 after transfection in human 293 cells. The use of optimized expression vector (IL15t, which indicates IL15tPA6OPT) having the tissue Plasminogen Activator (tPA) prepro leader sequence produced easily detectable levels of IL-15 in the media (i.e., extracellularly and intracellularly). Furthermore, co-expression of IL-15 together with IL15Ra resulted in a dramatic increase of IL-15 production, both intracellularly and extracellularly. This expression level was approximately 20-fold higher compared to the expression from the wild type cDNA.

Coexpression of IL-15 with the full length (i.e., whole) IL15Ra resulted in high levels of the IL-15 and IL15Ra molecules localized in the cell surface of expressing cells (FIG. 46), whereas coexpression of IL-15 with the soluble, extracellular portion of IL15Ra (i.e., soluble IL-15) resulted in rapid secretion of the complex in the medium. The total increase in IL-15 steady-state levels was 4-fold in the presence of IL15Ra and 7-fold in the presence of IL15sRa, as measured by ELISA (FIG. 45A).

Conversely, the presence of co-expressed IL-15 also increased the levels of IL15Ra and IL15sRa (FIG. 47). Western blot analysis using different dilutions of media and cell extracts after transfections of 293 cells with IL15Ra or IL15sRa in the presence or absence of IL-15 showed a 3- to 8-fold increase in receptor steady-state levels in the presence of IL-15. The receptor increase is in general similar to the IL-15 increase upon coexpression, measured above.

After expression of the membrane associated full IL15Ra, large quantities of the soluble extracellular portion were detected in the medium, consistent with rapid cleavage of the receptor and generation of the soluble form. When IL-15 was co-expressed, the levels of soluble receptor in the medium were elevated (FIG. 47C). Expression of IL15sRa resulted in high levels of a ~28 kDa intracellular form of the receptor, which is the primary transcript of the transfected cDNA, without any glycosylation, as well as an additional N-glycosylated ~30 kDa form (see below). Low levels of the fully glycosylated IL15sRa were found cell-associated, whereas most of it was secreted in the medium. In the presence of co-expressed IL-15, the intracellular non-glycosylated form was drastically reduced, whereas the glycosylated forms, especially the extracellular, were greatly increased. These results are consistent with the conclusion that an early intracellular association of IL-15 to its receptor alpha takes place during the production and secretion of these two molecules. In the absence of IL-15, IL15sRa remains to a large extent intracellular and it is not processed or secreted rapidly.

Both IL-15 and IL15Ra are glycosylated molecules and migrate as multiple bands in SDS-PAGE gels. IL15Ra is both N- and O-glycosylated (Dubois et al., 1999 *J Biol Chem* 274(38):26978-84), whereas IL-15 is N-glycosylated. It has been reported that the different IL15Ra protein products are due to alternate N- and O-glycosylations of a 39-kDa precursor (Dubois et al., 1999). Treatment with N- or O-glycosidases revealed that most of the cell associated IL15Ra receptor is rapidly glycosylated. In contrast, expression of the IL15sRa alone revealed an approximately 28 kDa band for the IL15sRa, which was only seen intracellularly. In the presence of IL15, this intracellular band decreased dramatically with coordinate increase in the extracellular glycosylated forms.

To determine whether the increased expression resulted in better biological activity, IL-15 and IL15Ra or IL15sRa DNA molecules were expressed in mice after hydrodynamic DNA delivery by tail vein injection. Mice were administered 0.1 µg to 2 µg DNA for these experiments, and IL-15 levels in the plasma were measured. Three days after a single DNA injection, mice were sacrificed and selected tissues were analyzed for the number and phenotype of T cells, NK cells, and other lymphocyte subsets by flow cytometry. FIG. 52 shows that co-expression of IL-15 and the Receptor alpha increased the number of NK cells in the lung. This increase was more prominent when the plasmid expressing the receptor was injected at a higher molar ratio (3:1, 0.1 µg of IL-15 plasmid and 0.3 µg of IL15Ra plasmid). Co-expression of the soluble part of IL-15 Receptor alpha gave a dramatic increase in lung NK cells.

Example 4

This example shows the use of IL-15/IL15Ra combination in a therapeutic vaccination of macaques. The IL-15/IL15Ra combination increased antigen specific cells, especially CD8 effectors, and also cells that express IL-2 or IL-2 and IFNgamma upon antigen stimulation (i.e., multifunctional cells, which are considered important for effective vaccination).

This example also follows expression of IL-15 in macaque plasma, and show that IL-15/15Ra co-expression achieves detectable production in macaque plasma. Control experiments show that this production is much higher compared to animals receiving only IL-15 DNA.

Three macaques were subjected to a second round of antiretroviral treatment ("ART") and DNA vaccination using plasmids expressing improved IL-15 and IL-15 Receptor alpha (IL15Ra) Immunization was done by electroporation using the following plasmid mix: Two injections of 0.5 ml were performed for each animal. Peripheral blood monocytes ("PBMC") were isolated at 2 week intervals and analyzed for numbers of SIV-specific cells using 10 parameter flow cytometry. This allowed the enumeration and phenotypic analysis of lymphocytes producing IFNg, IL-2 or TNFa in response to stimulation by peptide pools corresponding to gag, pol, env, nef, and tat proteins of SIVmac259.

The results of this analysis (FIG. 56) show a dramatic increase of average and peak responses of SIV-specific cytokine producing cells. All three animals had low levels of IFNg producing cells during ART and prior to DNA vaccination. This is expected since ART decreased SIV to undetectable levels in all three animals. Upon vaccination a persistent increase of SIV-specific cells was detected. More importantly, vaccination generated IL-2-secreting cells (FIG. 56) as well as double IFNg and IL-2 secreting cells (i.e., multifunctional cells). This occurred only after the third DNA vaccination, whereas in all previous determinations these macaques did not have any polyfunctional cytokine secreting cells in their peripheral blood.

The three vaccinated macaques showed dramatic increases in the number of SIV-specific cytokine-producing cells in PBMC with either central memory (CM) or effector memory (EM) phenotype (FIG. 57). The appearance of increased levels of effector cells in PBMC upon vaccination with the optimized mix of DNAs is in contrast to our previous experience, where DNA vaccination was able to generate SIV-specific central memory but not effector memory cells. We attribute this to the more optimal mix of DNA vaccines and to the presence of effective levels of IL15/IL15Ra cytokine.

Macaque administered DNA encoding IL-15 without co-administration of DNA encoding IL15Ra did not have IL-2 producing cells.

In summary, the optimized DNA vaccine vector mix and the inclusion of optimized levels of DNAs expressing IL-15 and IL15Ra resulted in a dramatic increase in antigen-specific cells detected in the peripheral blood. In addition to increased levels of cells, important phenotypic differences were detected by our analysis. The vaccine-generated antigen-specific cells were shown to include IL-2 producing as well as dual IFNg and IL-2 producing cells. Vaccination with IL-15 and IL15Ra generated antigen-specific cells having an effector phenotype in addition to central memory antigen-specific cells. CD8+ effector cells are expected to be active against virus-infected cells, therefore these macaques will be able to better control virus upon release from ART. Surprisingly, approximately 1-2% of circulating lymphocytes are SIV specific as a result of the dramatic response to DNA vaccination. This indicates that DNA vaccination alone under optimized conditions can generate a strong, diverse, long-lasting and multifunctional repertoire of antigen specific cells. DNA vaccination was administered successfully many times (up to a total of 8 times) without adverse effects. Moreover, repeated administrations resulted in the production of multifunctional T cells. This represents a dramatic improvement in comparison to previous vaccination protocols.

DNA injection of IL15/IL15Ra combination appears responsible for a great mobilization of effector cells, which are detected in PBMC on their way to peripheral sites. If this is the case, these results suggest the effectiveness of optimized IL15/IL15Ra combination as DNA or protein to enhance the mobilization and function of lymphocytes at optimal intervals in vivo. This immunotherapy with IL-15 can be used to enhance the effects of therapeutic vaccination and can also be used to enhance the immune response against the virus in the absence of therapeutic vaccination or for a long time after vaccination.

The DNA vaccine vectors used in this therapeutic vaccination were a mix composed of six SIV antigen-expressing plasmids and 2 rhesus IL-15/IL-15 Receptor alpha expressing plasmids. LAMP-pol and LAMP-NTV plasmids produce protein fusions of pol or NefTatVif, respectively, to human Lysosomal Associated Membrane Protein.

2 S-CATEgagDX
21S-MCP3p39gag
99S-Env
73 S-MCP3-env
103 S-LAMP-pol
147S-LAMP-NTV

Rhesus IL-15/IL-15 Receptor alpha producing plasmids:
AG65-rhIL15tPA6
AG120-rhIL15Ra

---

What is claimed is:

1. An expression vector comprising:
   an IL-15 nucleic acid sequence encoding an interleukin-15 (IL-15) polypeptide, wherein the IL-15 nucleic acid sequence has at least 85% sequence identity to nucleotides 145-489 SEQ ID NO:3; and
   an IL-15 receptor α (IL-15Rα) nucleic acid sequence encoding an IL-15Rα polypeptide;
   wherein the IL-15 nucleic acid sequence and the IL-15Rα nucleic acid sequence are each operably linked to a promoter.

2. The expression vector of claim 1, wherein the IL-15 nucleic acid sequence has non-native nucleic acid bases at 80% or more of the 80 nucleotide positions 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 of SEQ ID NO:3.

3. The expression vector of claim 1, wherein the IL-15 nucleic acid sequence has non-native nucleic acid bases at 90% or more of the 80 nucleotide positions 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486 of SEQ ID NO:3.

4. The expression vector of claim 1, wherein the IL-15 nucleic acid sequence has non-native nucleic acid bases at 95% or more of the 80 nucleotide positions 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486 of SEQ ID NO:3.

5. The expression vector of claim 1, wherein the IL-15 nucleic acid sequence comprises a guanine (g) or a cytosine (c) nucleotide at nucleotide positions 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486 of SEQ ID NO:3.

6. The expression vector of claim 1, wherein the IL-15 nucleic acid sequence comprises at least 50% GC content.

7. The expression vector of claim 1, wherein the IL-15 nucleic acid sequence has at least 95% sequence identity to nucleotides 145-489 of SEQ ID NO:3.

8. The expression vector of claim 1, wherein the IL-15 nucleic acid sequence encodes the region of SEQ ID NO:2 corresponding to mature IL-15.

9. The expression vector of claim 8, wherein the IL-15 nucleic acid sequence has at least 90% identity to SEQ ID NO:3.

10. The expression vector of claim 1, wherein the IL-15 nucleic acid sequence comprises nucleotides 145-489 of SEQ ID NO:3.

11. The expression vector of claim 1, wherein the expression vector comprises a nucleic acid sequence encoding a signal peptide-propeptide (SIG-PRO) or a signal peptide (SIG) from a heterologous protein fused to the nucleic acid sequence encoding the IL-15 polypeptide and/or a nucleic acid sequence encoding a signal peptide-propeptide (SIG-PRO) or a signal peptide (SIG) from a heterologous protein fused to the nucleic acid sequence encoding the IL-15Rα polypeptide.

12. The expression vector of claim 11, wherein the heterologous protein is selected from the group consisting of granulocyte-macrophage colony stimulating factor (GM-CSF), tissue plasminogen activator (tPA), growth hormone, and an immunoglobulin.

13. The expression vector of claim 1, wherein the IL-15 nucleic acid sequence and the IL-15Rα nucleic acid sequence are each operably linked to different promoters.

14. The expression vector of claim 1, wherein the IL-15Rα nucleic acid sequence comprises a codon optimized nucleic acid sequence encoding human IL-15Rα.

15. The expression vector of claim 1, wherein the IL-15Rα nucleic acid sequence has at least 95% sequence identity to SEQ ID NO:47 or at least 95% sequence identity to SEQ ID NO:49.

16. The expression vector of claim 15, wherein the IL-15Rα nucleic acid sequence comprises the nucleic acid sequence of SEQ ID NO:47 or SEQ ID NO:49.

17. A host cell comprising the expression vector of claim 1.

18. The host cell of claim 17, wherein the host cell is a mammalian host cell.

19. The host cell of claim 18, wherein the mammalian host cell is human.

20. The host cell of claim 18, wherein the host cell is a HEK 293-T, COS, CHO, HeLa, NIH3T3, RD or PC12 cell.

21. The host cell of claim 19, wherein the host cell is a HEK293 cell.

22. A method of producing IL-15 and IL-15Rα, the method comprising culturing the host cell of claim 17 under conditions in which IL-15 and IL-15Rα are expressed as a heterodimer.

23. The method of claim 22, wherein the IL-15 nucleic acid sequence is operably linked to a human cytomegalovirus (CMV) promoter and IL-15Rα nucleic acid sequence is operably linked to a simian virus CMV promoter.

24. The method of claim 22, further comprising isolating a complex comprising IL-15 and IL-15Rα.

25. A host cell comprising an IL-15 nucleic acid sequence encoding an interleukin-15 (IL-15) polypeptide, wherein the IL-15 nucleic acid sequence has at least 85% sequence identity to nucleotides 145-489 SEQ ID NO:3; and an IL-15receptor α(IL-15Rα) nucleic acid sequence encoding an IL-15Rα polypeptide.

26. A method of producing IL-15 and IL-15Rα, the method comprising culturing the host cell of claim 25 under conditions in which IL-15 and IL-15Rα are expressed as a heterodimer.

* * * * *